United States Patent [19]

Tilley et al.

[11] Patent Number: 4,916,145

[45] Date of Patent: Apr. 10, 1990

[54] SUBSTITUTED N-[(PYRIDYL)ALKYL]ARYL-CARBOXAMIDE

[75] Inventors: Jefferson W. Tilley, North Caldwell; Robert W. Guthrie, Saddle Brook; John W. Clader, Cranford; Ronald A. LeMahieu, North Caldwell, all of N.J.

[73] Assignee: Hoffmann-La Roche Inc., Nutley, N.J.

[21] Appl. No.: 72,386

[22] Filed: Jul. 10, 1987

[51] Int. Cl.⁴ ............ C07D 213/56; C07D 213/65; C07D 213/70; A61K 31/44
[52] U.S. Cl. .................... 514/357; 514/346; 514/352; 546/291; 546/305; 546/309; 546/331; 546/337
[58] Field of Search ............ 546/337, 291, 331, 337, 546/305, 309; 514/357, 346, 352

[56] References Cited

U.S. PATENT DOCUMENTS 4,743,610  5/1988  Wright, Jr. et al. .............. 514/357

FOREIGN PATENT DOCUMENTS

| 3330403 | 3/1984 | Fed. Rep. of Germany | 548/341 |
|---|---|---|---|
| 3406416 | 8/1984 | Fed. Rep. of Germany | 548/341 |
| 57-18973 | 1/1982 | Japan | 546/329 |
| 57-21370 | 2/1982 | Japan | 546/336 |

OTHER PUBLICATIONS

Yoshimoto, M. et al.: J. Med. Chem. 19(1), 71-98 (1976).
Baker, B. et al, J. Heterocycl. Chem. 4(3) 188-194 (1967).
Wright, W. B., J. Med. Chem., 29(4) 523-30 (1986).
Diabetologia, 30, 41-4, (1987).
Press, J. B., J. Med. Chem. (1987) 30, 1036-1040.
Berlin, A Y et al, Khim Geterotsikl Soedin, 7(9) 1280-2 (1971), CA 76 (9):46157d.

Primary Examiner—Alan L. Rotman
Attorney, Agent, or Firm—George M. Gould; Bernard S. Leon; William G. Isgro

[57] ABSTRACT

The invention relates to compounds of the formula

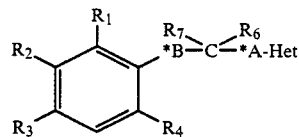

I wherein *B is

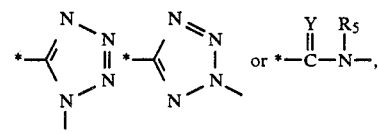

Y is O or S, *A is *—$(CH_2)_n$—$(X)_m$—$(CH_2)_r$—, n or r, independently, are integers from 0 to 3, m is an integer from 0 to 1, provided that when m is 1, then n must be at least 1, X is O or S, $R_1$ and $R_4$, independently, are hydrogen, lower alkyl, hydroxy or lower alkoxy, provided that when *B is other than

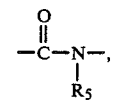

at least one of $R_1$ and $R_4$, and one of $R_6$ and $R_7$ must be hydrogen, $R_2$ and $R_3$ are independently hydrogen, lower alkyl, cycloalkyl, halogen, nitro, lower alkoxy, lower alkenyl, lower alkynyl or aryl, $R_5$ and $R_6$, independently are hydrogen or lower alkyl, $R_7$ is hydrogen, lower alkyl, cycloalkyl or aryl, Het is a monocyclic 5- or 6-membered hetero aromatic or a bicyclic heteroaromatic radical containing one or two hetero atoms selected from nitrogen oxygen and sulfur, which radical may be substituted by lower alkyl, halogen or aryl, and the asterisk denotes the point of attachment, and when $R_6$ and $R_7$ are different, their enantiomers and racemic mixtures thereof, and pharmaceutical acceptable acid addition salts thereof.

The compounds of formula I exhibit activity as Platelet Activating Factor (PAF) antagonists and are, therefore, useful as agents for the prevention and treatment of vascular diseases, pulmonary diseases, dermatological disorders, transplant rejection, immunological disorders and inflammatory conditions.

19 Claims, No Drawings

SUBSTITUTED N-[(PYRIDYL)ALKYL]ARYL-CARBOXAMIDE

BRIEF SUMMARY OF THE INVENTION

The invention relates to compounds of the formula

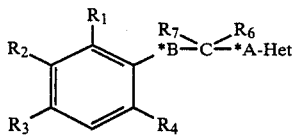

wherein *B is

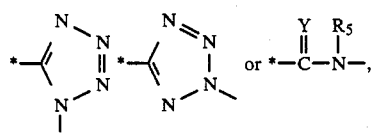

Y is O or S, *A is —(CH$_2$)$_n$—(X)$_m$—(CH$_2$)$_r$—, n or r, indep integers from 0 to 3, m is an integer from 0 to 1, provided that when m is 1, then n must be at least 1, X is O or S, R$_1$ and R$_4$, independently, are hydrogen, lower alkyl, hydroxy or lower alkoxy, provided that when *B is other than

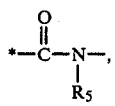

at least one of R$_1$ and R$_4$, and of R$_6$ and R$_7$ must be hydrogen, R$_2$ and R$_3$ are independently hydrogen, lower alkyl, cycloalkyl, halogen, nitro, lower alkoxy, lower alkenyl, lower akynyl or aryl R$_5$ and R$_6$, independently are hydrogen or lower alkyl, R$_7$ is hydrogen, lower alkyl, cycloalkyl or aryl, Het is a monocyclic 5- or 6-membered heteroaromatic or a bicyclic heteroaromatic radical containing one or two hetero atoms selected from nitrogen, oxygen and sulfur, which radical may be substituted by lower alkyl, halogen or aryl, and the asterisk denotes the point of attachment, and when R$_6$ and R$_7$ are different, their enantiomers and racemic mixtures thereof, and pharmaceutically acceptable acid addition salts thereof.

The compounds of formula I exhibit activity as platelet Activating Factor (PAF) antagonists and are, therefore, useful in amiliorating disease states characterized by excess platelet activating factor. For example, they are useful in the prevention and treatment of cardiovascular diseases, pulmonary diseases, immunological disorders, inflammatory diseases, dermatological disorders, shock, or transplant rejection.

DETAILED DESCRIPTION OF THE INVENTION

The invention relates to compounds of the formula

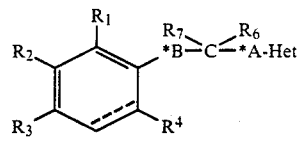

wherein *B is

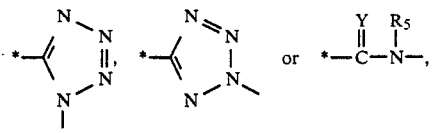

Y is O or S, A is —(CH$_2$)$_n$—(X)$_m$—(CH$_2$)$_r$—, n or r, independently, are integers from 0 to 3, m is an integer from 0 to 1, provided that when m is 1, then n must be at least 1, X is O or S, R$_1$ and R$_4$, independently, are hydrogen, lower alkyl, hydroxy or lower alkoxy, provided that when *B is other than

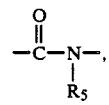

at least one of R$_1$ and R$_4$, and one of R$_6$ and R$_7$ must be hydrogen, R$_2$ and R$_3$ are independently hydrogen, lower alkyl, cycloalkyl, halogen, nitro, lower alkoxy, lower alkenyl, lower alkynyl or aryl, R$_5$ and R$_6$, independently, are hydrogen or lower alkyl, R$_7$ is hydrogen, lower alkyl, cycloalkyl or aryl, Het is a monocyclic 5- or 6-membered heteroaromatic or a bicyclic heteroaromatic radical containing one or two hetero atoms selected from nitrogen, oxygen and sulfur, which radical may be substituted by lower alkyl, halogen or aryl, and the asterisk denotes the point of attachment, and, when R$_6$ and R$_7$ are different, their enantiomers and racemic mixtures thereof, and pharmaceutically acceptable acid addition salts thereof.

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "cycloalkyl" denotes a cyclic alkyl group of 3 to 6 carbon atoms, for example, cyclopropyl, cyclohexyl, and the like. The term "lower alkoxy" denotes an alkyl ether group in which the lower alkyl group is as described above, for example, methoxy, ethoxy, propoxy, pentoxy, and the like. The term "lower alkenyl" denotes a straight or branched chain unsaturated hydrocarbon containing 2 to 7 carbon atoms, for example, propenyl, butenyl and the like. The term "lower alkynyl" denotes a straight or branched chain unsaturated hydrocarbon containing 2 to 7 carbon atoms, for example, ethynyl, propynyl, butynyl and the like.

The term "halogen" denotes all the halogens, i.e., bromine, chlorine, fluorine, and iodine. The term "aryl" preferably denotes phenyl or naphthalenyl, or phenyl or naphthalenyl mono-, di- or trisubstituted by halogen, trifluoromethyl, lower alkyl, lower alkoxy or nitro.

The term "Het" denotes a monocyclic 5- or 6-membered heteroaromatic or a bicyclic heteroaromatic radical containing one or two hetero atoms, selected from nitrogen, oxygen and sulfur, which radical may be substituted by lower alkyl, halogen or phenyl, for example, pyridinyl, quinolinyl, isoquinolyl, imidazolinyl, indolyl, benzimidazolinyl, thienyl, furyl, pyrimidinyl, oxazolinyl and the like. It is understood that the heteroaromatic radical can be bonded through any of its carbon atoms.

A preferred group of compounds of formula I are those wherein $R_1$ is hydrogen or lower alkyl, $R_2$ is hydrogen, lower alkyl, lower alkenyl, lower alkynyl or aryl, $R_3$ is lower alkyl or aryl, $R_4$ is hydrogen, lower alkyl or lower alkoxy, B* is a carboxamide or thiocarboxamide, *A is $-(CH_2)_n-(X)_m-(CH_2)_r$ wherein $n+r=2$ to 6, m=0, $R_6$ is hydrogen or lower alkyl, $R_5$ and $R_7$ are hydrogen. Het is a monocyclic 5 or 6 membered heteroaromatic ring containing one or two heteroatoms selected from nitrogen, oxygen and sulfur.

A more preferred group of compounds of formula I are those wherein $R_1$ and $R_4$ independently are hydrogen or lower alkyl, $R_2$ is hydrogen, lower alkyl, lower alkenyl or aryl, $R_3$ is phenyl substituted with up to three substituents selected from halogen, lower alkyl, lower alkenyl and lower alkoxy, B* is a carboxamide or thiocarboxamide, $R_5$ is hydrogen, $R_6$ is hydrogen or lower alkyl, $R_7$ is hydrogen, *A is $-(CH_2)_n(X)_m(CH_2)_r-$ wherein $n+r=3-5$, m=0, B* is a carboxamide or thiocarboxamide and Het is pyridinyl or pyrimidinyl.

A still more preferred group of compounds of formula I are those wherein $R_1$ and $R_4$ are hydrogen, $R_2$ is hydrogen, phenyl, lower alkenyl or lower alkyl, Het is 3-pyridinyl or 3-pyrimidinyl, $R_3$ is phenyl optionally substituted with one or two lower alkoxy groups, $R_5$ and $R_7$ are hydrogen, $R_6$ is hydrogen or methyl, A* is $-(CH_2)_n(X)_m-(CH_2)_r-$ wherein $n+r=3$, m=0, B* is carboxamide or thiocarboxamide.

Preferred compounds of the invention are:
rac.-3′,4′-Dimethoxy-N-[1-methyl-4-(3-pyridinyl)butyl][1,1′-biphenyl]-4-carbothioamide; and
(R)-3′,4′-Dimethoxy-N-[1-methyl-4-(3-pyridinyl)butyl][1,1′-biphenyl]-4-carboxamide.
(R)-2-Butyl-3′,4′-dimethoxy-N-[1-Methyl-4-(3-pyridinyl)butyl][1,1′-biphenyl]-4-carboxamide.
(R)-2-Ethyl-3′,4′-dimethoxy-N-[1-Methyl-4-(3-pyridinyl)butyl][1,1′-biphenyl]-4-carboxamide.
(R)-2-(2-propenyl)-3′,4′-dimethoxy-N-[1-methyl-4-(3-pyridinyl) butyl]-[1,1′-biphenyl]-4-carboxamide Exemplary compounds of formula I of the invention are:
3′,4′-Dimethoxy-N-[6-(3-pyridinyl)hexyl][1,1′-biphenyl]-4-carboxamide;
3′,4′-Dimethoxy-N-[5-(3-pyridinyl)pentyl][1,1′-biphenyl]-4-carboxamide;
rac.-3,-methoxy-N-[1-methyl-3-(3-pyridinyl)propyl][1,1′-biphenyl]-4-carboxamide;
3′-methoxy-N-[3-(3-pyridinyl)propyl][1,1′-biphenyl]-4-carboxamide;
rac.-3′,4′-Dimethoxy-N-[1-ethyl-4-(3-pyridinyl)butyl][1,1′-biphenyl]-4-carboxamide;
2′,3′,4′-Trimethyl-N-[6-(3-pyridinyl)hexyl][1,1′-biphenyl]-4-carboxamide;
3′,4′-Dimethyl-N-[6-(3-pyridinyl)hexyl][1,1′-biphenyl]-4-carboxamide
rac.-3′,4′-Dimethoxy-N-[1-methyl-4-(2-methyl-3-pyridinyl)butyl][1,1′-biphenyl]-4-carboxamide;
(R)-3′,4′-Dichloro-N-[1-methyl-4-(3-pyridinyl)butyl][1,1′-biphenyl]-4-carboxamide;
3′,4′-Dimethoxy-2-phenyl-N-[4-(3-pyridinyl)butyl][1,1′-biphenyl]-4-carboxamide;
3′,4′-Diethoxy-N-[4-(3-pyridinyl)butyl][1,1′-biphenyl]-4-carboxamide;
rac.-3′,4′-Diethoxy-N-[1-methyl-4-(3-pyridinyl)butyl][1,1′-biphenyl]-4-carbothioamide;
3′,4′-Dimethoxy-2-propyl-N-[4-(3-pyridinyl)butyl][1,1′-biphenyl]-4-carbothioamide;
3′,4′-Dimethoxy-2-pentyl-N-[4-(3-pyridinyl)butyl][1,1′-biphenyl]-4-carbothioamide;
2-propyl-N-[4-(3-pyridinyl)butyl][1,1′-biphenyl]-4-carbothioamide;
2-pentyl-N-[4-(3-pyridinyl)butyl][1,1′-biphenyl]-4-carbothioamide;
3,3′,4′,5-Tetramethyl-N-[4-(3-pyridinyl)butyl][1,1′-biphenyl]-4-carboxamide;
3′,4′-Dimethoxy-N-[4-(1H-imidazol-1-yl)butyl][1,1′-biphenyl]-4-carboxamide;
3′,4′-Dimethoxy-N-[4-(5-pyrimidinyl)butyl][1,1-biphenyl]-4-carboxamide;
3′,4′-Dimethoxy-N-[4-(4-isoquinolinyl)butyl][1,1-biphenyl]-4-carboxamide;
3′,4′-Dimethoxy-N-[4-(3-thienyl)butyl][1,1′-biphenyl]-4-carboxamide;
3′,4′-Dimethoxy-N-[4-(2-thienyl)butyl][1,1′-biphenyl]-4-carboxamide;
3′,4′-Dimethoxy-N-[4-(oxazol-5-yl)butyl][1,1′-biphenyl]-4-carboxamide;
3′,4′-Dimethoxy-N-[4-(3-quinolinyl)butyl][1,1′-biphenyl]-4-carboxamide;
rac.-3,4-Diphenyl-N-[1-ethyl-4-(3-pyridinyl)butyl]benzamide;
(R)-3,4-bis-(4-Methoxyphenyl)-N-[1-Methyl-4-(3-pyridinyl) butyl]benzamide;
(R)-3,4-bis-(4-Fluorophenyl)-N-[1-Methyl-4-(3-pyridinyl)butyl]benzamide;
(R)-3,4-bis-(3-Methoxyphenyl)-N-[1-Methyl-4-(3-pyridinyl) butyl]benzamide;
(Rac)-3,5-Diphenyl-N-[1-Methyl-4-(3-pyridinyl)butyl]-benzamide;
rac.-3,4-Diphenyl-N-[1-methyl-4-(3-pyrimidinyl)butyl]-benzamide;
rac.-3′,4′-Dimethoxy-N-[1-methyl-4-(5-methyl-3-pyridinyl)butyl][1,1′-biphenyl]-4-carboxamide;
rac.-3′,4′-Dimethoxy-N-[1-methyl-4-(5-ethyl-3-pyridinyl)butyl][1,1′-biphenyl]-4-carboxamide;
3′,4′-Dimethoxy-N-[3-[(3-pyridinyl)oxy]propyl][1,1′-biphenyl]-4-carboxamide;
3′,4′-Dimethyl-2-propyl-N-[4-(3-pyridinyl)butyl[1,1′-biphenyl]-4-carboxamide;
2-Butyl-4′-methoxy-N-[4-(3-pyridinyl)butyl[1,1′-biphenyl]-4-carboxamide;
2-nitro-2′,3′,4′-Trimethoxy-N-[4-(3-pyridinyl)butyl[1,1′-biphenyl]-4-carboxamide;
rac.-2,3′,4′-Trimethoxy-N-[1-Methyl-4-(3-pyrimidinyl)butyl][1,1′-biphenyl]-4-carboxamide;
3′,4′-Dimethoxy-2-pentyl-N-[4-(3-pyridinyl)butyl][1,1′-biphenyl]-4-carboxamide;
3′,4′-Dimethoxy-2-ethyl-N-[4-(3-pyridinyl)butyl][1,1′-biphenyl]-4-carboxamide;
2-propyl-N-[4-(3-pyridinyl)butyl][1,1′-biphenyl]-4-carboxamide;
2-Butyl-N-[4-(3-pyridinyl)butyl][1,1′-biphenyl]-4-carboxamide;
(R)-2-propyl-N-[1-Methyl-4-(3-pyridinyl)butyl][1,1,-biphenyl]-4-carboxamide;
(R)-2-Butyl-N-[1-Methyl-4-(3-pyridinyl)butyl][1,1,-biphenyl]-4-carboxamide;
3′-propyl-N-[4-(3-pyridinyl)butyl][1,1′-biphenyl]-4-carboxamide;

(R)-3'-Methyl-N-[1-Methyl-4-(3-pyridinyl)butyl][1,1'-biphenyl]-4-carboxamide;

can be prepared as hereinafter described in Reaction Schemes I, II and III.

REACTION SCHEME I

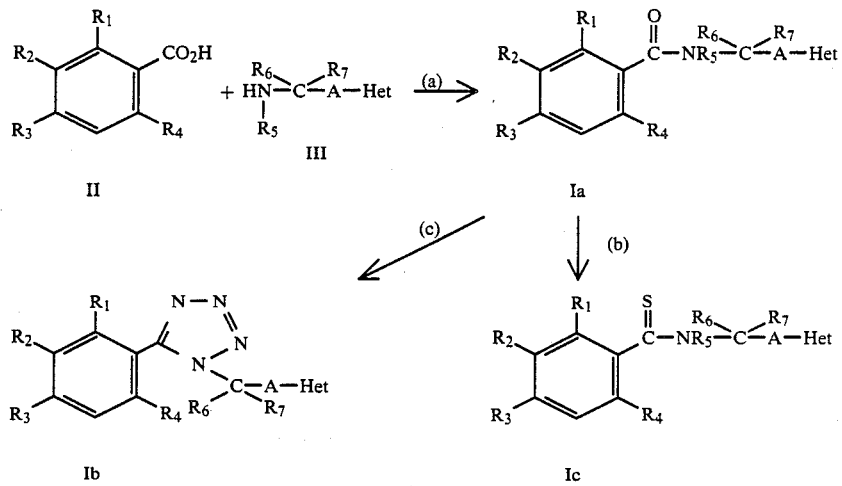

wherein $R_1$, $R_2$, $R_3$, $R_4$, $R_5$, $R_6$, $R_7$, A, and Het are as previously described.

In Reaction Scheme I, step (a), a compound of formula II, which are known compounds or can be prepared as hereinafter described, and a compound of formula III, which are known compounds or can be prepared as hereinafter described, are reacted using standard peptide coupling methodology. For example, reaction of an acid of formula II with an amine of formula III to give a compound of formula Ia can be carried out in a polar solvent such as dimethylformamide, N-methylpyrrolidinone, acetonitrile or the like, in the presence of a diimide such as dicyclohexylcarbodiimide, or the like, optimally in the presence of catalyst such as 4-dimethylaminopyridine, 1-hydroxybenzotriazole or the like, at a temperature in the range of from 0° to room temperature.

Alternatively, the reaction of an acid of formula II with an amine of formula III to give a compound of formula Ia can be carried out in a polar solvent such as dimethylformamide, N-methylpyrrolidinone, acetonitrile or the like, in the presence of diphenylphosphorylazide and a proton acceptor, that is, a base, for example, triethylamine or the like, or in the presence of an excess of the compound of formula III at a reaction temperature in the range of 0° to room temperature. Alternatively, an acid of formula II can be converted to the corresponding acid halide by reaction, for example, with thionyl chloride, oxalyl chloride or the like, optionally in the presence of an inert cosolvent such as dichloromethane or the like, and the resulting acid halide can be reacted with an amine of formula III in an inert solvent such as dichloromethane, tetrahydrofuran or the like, in the presence of a proton acceptor, for example, triethylamine or the like, or in the presence of an excess of the compound of formula III to give a compound of formula Ia. The resulting compound of formula Ia can be isolated utilizing conventional methods, for example, crystallization, chromatography or the like.

In step (b), an amide of formula Ia is reacted with phosphorous pentasulfide in pyridine solution at a temperature of from 80° C. to the reflux temperature of the (R)-4'-Methyl-N-[1-Methyl-4-(3-pyridinyl)butyl][1,1'-biphenyl]-4-carboxamide;
(R)-3'-Fluoro-N-[1-Methyl-4-(3-pyridinyl)butyl][1,1'-biphenyl]-4-carboxamide;
(R)-3',4'-Dimethoxy-2-propynyl-N-[1-methyl-4-(3-pyridinyl) butyl][1,1'-biphenyl]-4-carboxamide
3'-Chloro-N-[4-(3-pyridinyl)butyl][1,1'-biphenyl-4-carboxamide;
4'-Nitro-N-[4-(3-pyridinyl)butyl][1,1'-biphenyl]-4-carboxamide;
3,4-Dipropyl-N-[4-(3-pyridinyl)butyl]benzamide;
(R)-2-Allyl-3',4'-dimethyl-N-[1-methyl-4-(3-pyridinyl)butyl]1,1'-biphenyl]-4-carboxamide;
(R)-3,4-Dipropyl-N-[1-methyl-4-(3-pyridinyl)butyl]benzamide;
3,4-Dibutyl-N-[4-(3-pyrimidinyl)butyl]benzamide;
(R)-4-butyl-3-phenyl-N-[1-methyl-4-(3-pyridinyl)butyl]benzamide
(R)-3',4'-Dimethoxy-2-isopropyl-N-[1-methyl-4-(3-pyridinyl)butyl][1,1'-biphenyl]-4-carboxamide;
(R)-3',4'-Dimethoxy-2-isobutyl-N-[1-methyl-4-(3-pyridinyl)butyl][1,1'-biphenyl]-4-carboxamide;
(R)-3',4'-Dimethoxy-2-chloro-N-[1-methyl-4-(3-pyridinyl)butyl][1,1'-biphenyl]-4-carboxamide;
(R)-3',4'-Dimethoxy-2-methyl-N-[1-methyl-4-(3-pyridinyl)butyl][1,1'-biphenyl]-4-carboxamide;
(R)-3',4'-Dimethoxy-2-pentyl-N-[1-methyl-4-(3-pyridinyl)butyl][1,1'-biphenyl]-4-carboxamide;
rac.-3',4'-Dimethoxy-N-[1-propyl-4-(3-pyridinyl)butyl][1,1'-biphenyl]-4-carboxamide;
(R)-3',4'-Dimethyl-2-ethyl-N-[1-methyl-4-(3-pyridinyl)butyl][1,1'-biphenyl]-4-carboxamide;
rac.-3',4'-Dimethoxy-N-[1-cyclopropyl-4-(3-pyridinyl)butyl]1,1'-biphenyl]-4-carboxamide;
rac.-3',4'-Dimethoxy-N-[1-butyl-4-(3-pyridinyl)butyl][1,1'-biphenyl]-4-carboxamide;
3',4'-Dimethoxy-N-[4-(4-pyridinyl)butyl][1,1'-biphenyl]-4-carboxamide;
3',4'-Dimethoxy-N-[4-(2-pyridinyl)butyl][1,1'-biphenyl]-4-carboxamide; and the like.

The compounds of formula I, enantiomers and racemates when $R_6$ and $R_7$ are different, and salts thereof solvent to give a compound of formula Ic. The resulting compound of formula Ic can be isolated utilizing conventional methods, for example, crystallization, chromatography or the like.

In step (c), an amide of formula Ia wherein $R_5$ is hydrogen is reacted with phosphorous pentachloride in an inert solvent such as toluene, benzene, or the like, at a temperature in the range of from 10° C. to 40° C. until imidoyl chloride formation is complete. Addition of hydrazoic acid or solid sodium azide and heating the reaction mixture to a temperature in the range of from 80° C. to 120° C. completes the formation of a compound of formula Ib. The resulting compound of formula Ib can be isolated utilizing conventional methods, for example, crystallization, chromatography or the like.

Compounds of formula I in which $R_1$ or $R_4$ are hydroxy can be obtained by cleavage of a suitable hydroxy protecting group. For example, a compound of formula I in which either or both of $R_1$ and $R_4$ are benzyloxy is hydrogenated over a suitable catalyst, for example palladium on carbon or platinum oxide preferably in a solvent, for example a lower alkanol such as ethanol to give the corresponding compound of formula I, in which either or both of $R_1$ and $R_4$ are hydroxy. The resulting compound can be isolated utilizing conventional means, for example crystallization, chromatography or the like.

REACTION SCHEME II

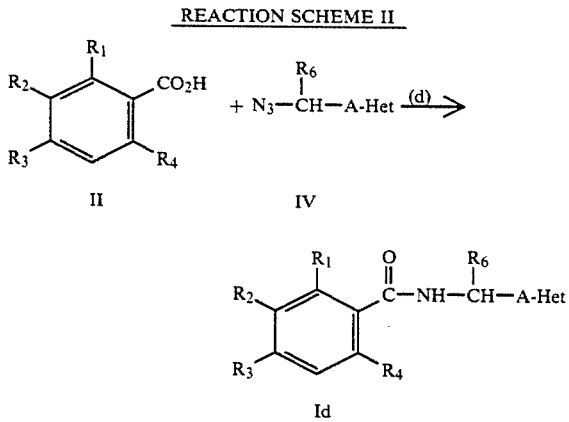

wherein $R_1$, $R_2$, $R_3$, $R_4$, $R_6$, A, and Het are as previously described.

In Reaction Scheme II, step (d), a compound of formula II is reacted with a compound of formula IV, which can be prepared as hereinafter described, in a inert solvent, for example benzene or toluene, in the presence of a phosphine, for example, triphenyl phosphine, at a temperature in the range of from about 80° to about 120° C. to give a compound of formula Id. The resulting compound of formula Id can be isolated utilizing conventional methods, for example, crystallization, chromatography or the like.

REACTION SCHEME III

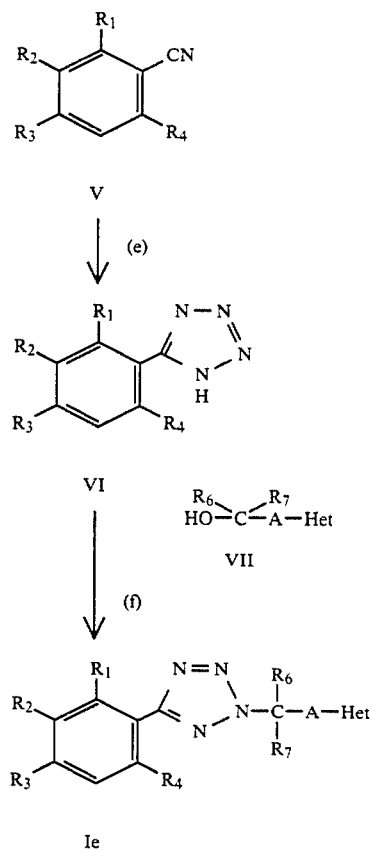

wherein $R_1$, $R_2$, $R_3$, $R_4$, $R_6$, $R_7$, A and Het are as previously described, provided that one of $R_1$ and $R_4$ is hydrogen, and one of $R_6$ and $R_7$ is hydrogen.

In Reaction Scheme III, step (e), a compound of formula V, which are known compounds or can be prepared as hereinafter described, is reacted with sodium azide and ammonium chloride in the presence of a polar aprotic solvent such as dimethylformamide, N-methylpyrrolidinone or the like, at a temperature in the range of from about 90° C. to about 125° C. until tetrazole formation is complete. The resulting compound of formula VI can be isolated utilizing conventional methods, for example, crystallization, chromatography or the like.

In step (f), a compound of formula VI and an alcohol of formula VII, which are known compounds or can be prepared as hereinafter described, are reacted in the presence of a dialkyl azodicarboxylate, for example, diethyl azodicarboxylate, and a phosphine, for example, triphenyl phosphine, in an inert solvent, for example, dichloromethane, according to the general method described by O. Mitsunobu (Synthesis 1981, 1) to give a compound of formula Ie. The resulting compound of formula Ie can be isolated utilizing conventional methods, for example, crystallization, chromatography or the like.

REACTION SCHEME IV

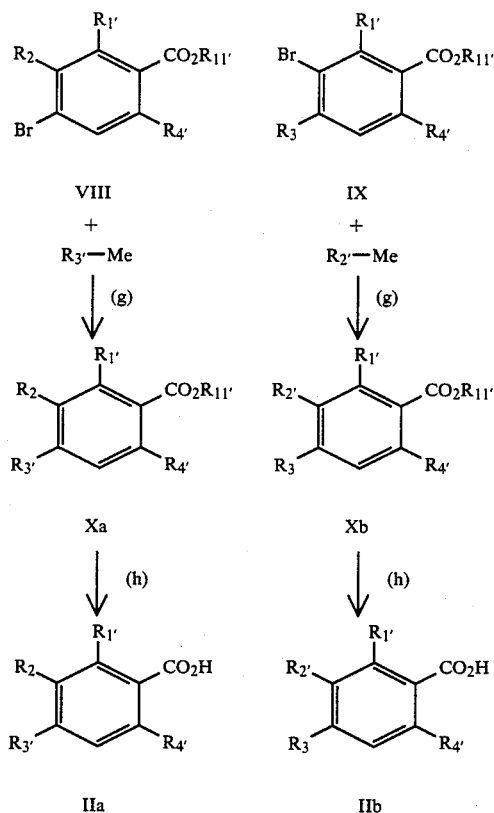

wherein $R_{1'}$ and $R_{4'}$ independently are lower alkyl, or hydrogen, $R_2$ and $R_3$ are as previously described, $R_{2'}$ and $R_{3'}$ are lower alkenyl, lower alkynyl or aryl, Me is a metal selected from zinc and tin, and $R_{11'}$ is lower alkyl or benzyl.

In Reaction Scheme IV, step (g), a radical of formula $R_{2'}$, or $R_{3'}$, displaces a bromine atom on a compound of formula VIII or IX to give a compound of formula Xa or Xb respectively. When $R_{2'}$, or $R_{3'}$, is a terminal alkyne or alkene and Me is hydrogen, coupling is effected by reaction with a compound of formula VIII or IX in an inert solvent, for example dimethyl formamide, tetrahydrofuran, dichloromethane or the like in the presence of a suitable proton acceptor, for example triethylamine and in the presence of a source of palladium zero, for example bis(triphenylphosphine)palladium dichloride until reaction is complete. This methodology has been described in H. A. Dieck and R. F. Heck, J. Am. Chem. Soc. 1974 96, 1133 for alkenyl derivatives and in J. W. Tilley, U.S. Pat. No. 4,551,460 for alkynyl derivatives. When Me represents a zinc halide, for example zinc chloride, prepared for example from reaction of the corresponding $R_{2'}$, or $R_{3'}$, lithium derivative with anhydrous zinc chloride, said zinc derivative can be reacted with a compound of formula VIII or IX in an inert solvent, for example tetrahydrofuran, in the presence of a source of palladium zero, for example, bis(triphenylphosphine)palladium dichloride at a temperature of about room temperature to give a compound of formula Xa or Xb respectively. This methodology has been described in A. O. King and E-i. Negishi, J. Org. Chem., 1978, 43, 358 for alkynyl derivatives and in E.-i. Negishi, A. O. King, and N. Okukado, J. Org. Chem.

1977, 42, 1821 for aryl derivatives. In the special case where $R_{2'}$, or $R_{3'}$, are optionally substituted allyl derivatives and Me is tris(lower alkyl)tin, coupling may be effected by reaction of the tin derivative with a compound of formula VIII or IX in the presence of a suitable solvent, for example dimethylformamide or the like, and a suitable catalyst, for example, a source of palladium zero, for example bis(triphenylphosphine)palladium dichloride at a temperature of from 50° to 100° C. until reaction is complete. The resulting compound of formula Xa or Xb can be isolated utilizing conventional methods, for example, crystallization, chromatography or the like.

In Reaction Scheme IV, step (h), a compound of formula Xa or Xb is dissolved in a suitable solvent, for example, a lower alkanol, and is treated with a source of hydroxide ion, for example an alkali metal hydroxide at a temperature of from 0° C. to the reflux temperature of the solvent, preferably at room temperature, until hydrolysis is complete. The resulting compound of formula IIa or IIb can be isolated utilizing conventional methods, for example, by acid base extraction followed by crystallization or chromatography.

REACTION SCHEME V

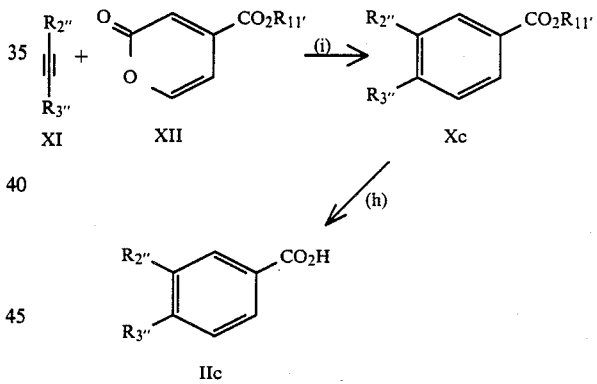

wherein $R_{2''}$ and $R_{3''}$ independently are lower alkyl or aryl and $R_{11'}$ is as previously described.

In Reaction Scheme V, step (i), an acetylene of formula XI and an ester of formula XII are reacted in an inert aromatic solvent, for example toluene as described (J. A. Reed, C. L. Schilling, R. F. Tarvin, T. A. Rettig, and J. K. Stille, J. Org. Chem. 1969, 34, 188) to give a compound of formula Xc. The resulting compound of formula Xc can be isolated utilizing conventional methods, for example, crystallization, chromatography or the like. An ester of formula Xc can be hydrolized to give an acid of formula IIc in accordance with step (h) as described for step (h) in Reaction Scheme IV.

REACTION SCHEME VI

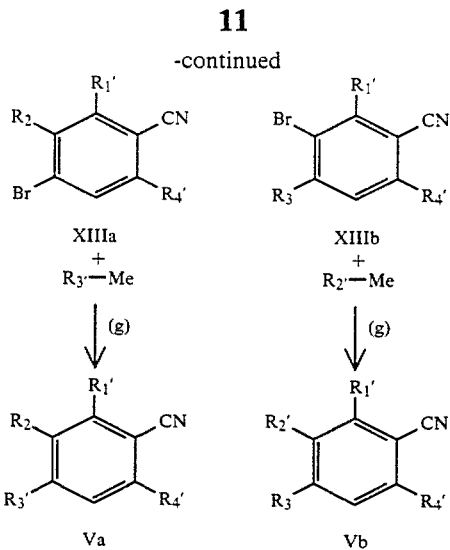

wherein $R_{1'}$, $R_2$, $R_3$, $R_{4'}$, $R_{2'}$, $R_{3'}$, Me and Aryl' are as previously described.

In Reaction Scheme VI, step (g), is carried out as described in Reaction Scheme IV, step (g). The resulting compound of formula Va or Vb can be isolated utilizing conventional methods, for example, crystallization, chromatography or the like.

REACTION SCHEME VII

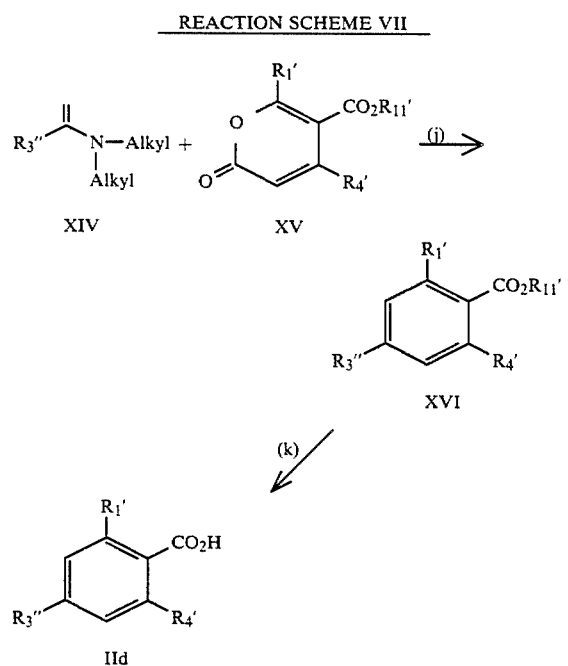

wherein $R_{1'}$, $R_{3''}$, $R_{4'}$, and $R_{11'}$ are as previously described.

In Reaction Scheme VII, step (j), an enamine of formula XIV, which are known compounds or can be prepared by known methodology, is reacted with an ester of formula XV preferably in the absence of solvent at a temperature of from 140° to 160° C. until biphenyl formation is complete according to the general procedure described (H. L. Gingrich, D. M. Roush, W. A. Van Saun, J. Org. Chem. 1983, 48, 4869). The resulting compound of formula XVI can be isolated utilizing conventional methods, for example, crystallization, chromatography or the like.

In Reaction Scheme VII, step (k), an ester or formula XVI is reacted with an alkali metal hydroxide in a lower alkanol as solvent, preferably at the reflux temperature of the solvent until ester hydrolysis is complete. The resulting compound of formula IId can be isolated utilizing conventional methods, for example, crystallization, chromatography or the like.

REACTION SCHEME VIII

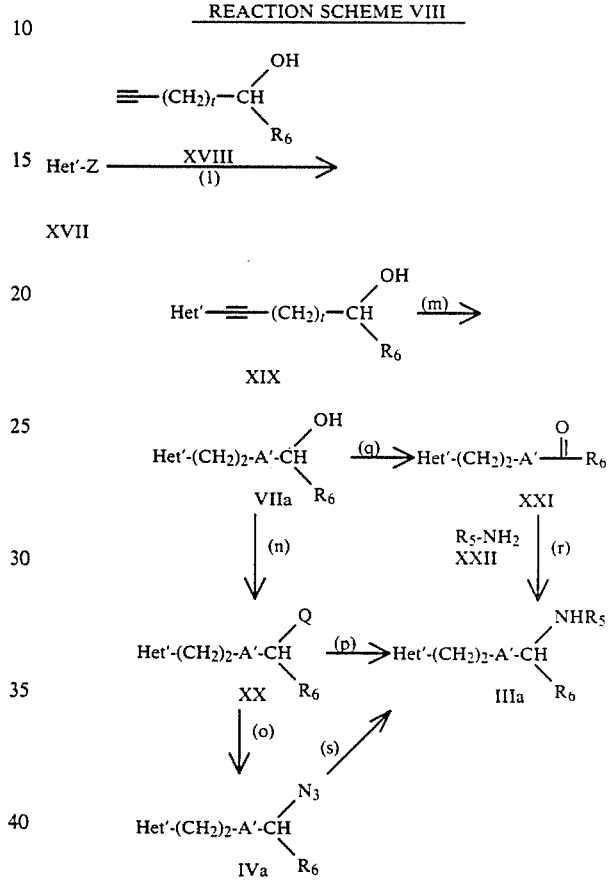

Het'—Z is a monocyclic 5- or 6-membered heteroaromatic of a bicyclic heteroaromatic compound containing one or two heteroatoms selected from nitrogen, oxygen, and sulfur, which compound maybe substituted by halogen, lower alkyl of aryl wherein Z is iodide, bromide, or perfluoroalkyl-sulfonyloxy and is substituted in a position on the heteroaromatic ring such that it is active in transition metal catalyzed aryl-alkynyl coupling reactions. The compound of formula XVIII becomes attached to Het' at the position of the leaving Z group. Examples of Het' are: 3-pyridinyl, 5-pyrimidinyl, 2-thienyl, 3-thienyl, 2-pyridinyl, 6-methyl-2-pyridinyl, 2-methyl-3-pyridinyl, 3-quinolinyl, 4-isoquinolinyl and the like. t is an integer of 0 to 4, A' is akylene of 1 to 4 carbon atoms. Q is bromo, chloro, or an alkyl- or arylsulfonyloxy radical, and $R_5$ and $R_6$ are as previously described.

In Reaction Scheme VIII, step (l), a compound of formula XVII is reacted with an acetylene of formula XVIII in the presence of an excess of a proton acceptor, for example, triethylamine, and a suitable palladium catalyst, for example, bis(triphenylphosphine)palladium dichloride, optionally in the presence of an inert solvent, for example, dichloromethane or dimethylformamide, at a temperature of from room temperature to 100° C. depending on the particular choice of Z—, solvent, and heteroaromatic ring, to give a compound of formula XIX. The resulting compound of formula XIX can be isolated utilizing conventional methods, for example, distillation, chromatography or the like, or may be used directly in the next step of the synthesis.

In Reaction Scheme VIII, step (m), an acetylene of formula XIX is dissolved in an inert solvent, for example, a lower alkanol, and hydrogenated over a suitable catalyst, for example, palladium on carbon, platinum oxide or the like, at a hydrogen pressure of from one to five atmospheres, preferably at room temperature, until reduction is complete. The resulting compound of formula VIIa can be isolated utilizing conventional methods, for example, distillation, chromatography or the like. Compounds of formula VIIa in which $R_6$ is other than hydrogen may be resolved into their enantiomers using standard methodology, for example, conversion to esters of chiral acids and chromatographic separation followed by ester hydrolysis.

In Reaction Scheme VIII, step (n), an alcohol of formula VIIa is reacted with an alkyl or aryl sulfonyl halide, for example, methane sulfonyl chloride or toluene sulfonyl chloride in the presence of a proton acceptor, for example, pyridine or triethylamine to give a compound of formula XX wherein Q is an alkyl- or arylsulfonyloxy radical of the same absolute chirality as the starting alcohol VIIa. Alternatively, a compound of formula VIIa can be reacted with a reagent useful for the conversion of alcohols into halides, for example, thionyl chloride, in the presence of a proton acceptor, for example, pyridine, until conversion to a compound of formula XX, Q=Cl, or Br is complete. The resulting compound of formula XX generally is not isolated, but utilized directly in the next step.

In Reaction Scheme VIII, step (o), a compound of formula XX, is reacted with an alkali metal azide, for example, sodium azide, in the presence of a polar inert solvent, for example, dimethylformamide, N-methylpyrrolidinone, dimethylsulfoxide or the like at a temperature of from about room temperature to 100° C. until azide formation is complete. The resulting compound of formula IVa can be isolated utilizing conventional methods, for example, chromatography or the like. This transformation generally proceeds with inversion of chirality at the carbon atom of XX bearing Q.

In Reaction Scheme VIII, step (p), a compound of formula XX is reacted with an amine anion equivalent to give an intermediate which can be deprotected to give an amine of formula IIIa. For example, a compound of formula XX can be reacted with an alkali metal phthalimide, for example, potassium phthalimide, in a polar aprotic solvent, for example dimethylformamide, dimethyl sulfoxide, N-methylpyrrolidinone, or the like at a temperature of from about 60° to 120° C. until reaction is complete to give an intermediate of formula XX, Q=phthalimido which can be converted to a compound of formula IIIa, by conventional means, for example by treatment with hydrazine in a lower alkanol solvent or with methylamine in a polar aprotic solvent such as dimethylformamide. Alternatively, a compound of formula XX can be reacted with a perfluoroalkylsulfonamide derived from a primary amine, for example an N-alkyltrifluoromethanesulfonamide, in a polar aprotic solvent, for example, acetone, dimethylformamide, dimethylsulfoxide or the like in the presence of a base, for example, an alkali metal hydroxide or as appropriate, an alkali metal hydride, for example sodium hydride at a temperature of from room temperature to 100° C. The resulting compounds of formula IIIa can be isolated utilizing conventional methods, for example, distillation, crystallization of their acid addition salts, chromatography or the like. When a compound of formula XX is chiral, this transformation will generally proceed with inversion of configuration at the carbon atom bearing Q in a compound of formula XX.

In Reaction Scheme VIII, step (q), an alcohol of formula VIIa is oxidized to a carbonyl derivative of formula XXI. Reagents which are useful for this transformation include chrominum based oxidizing reagents, for example, pyridinium chlorochromate. A preferable procedure is described in K. Omura and D. Swern, Tetrahedron 1978, 34, 1651, which involves dissolution of a slight excess of an acid halide, for example, oxalyl chloride in an inert halocarbon solvent, for example dichloromethane, cooling to a reaction temperature of from $-50°$ to $-80°$ C., addition of excess dimethyl sulfoxide, stirring for 0.25 to 0.5 hours, addition of one equivalent of an alcohol of formula VIIa, after an additional 0.25 to 0.5 hours, addition of excess triethylamine while maintaining the reaction temperature at from $-50°$ to $-80°$ C. and allowing the reaction mixture to warm for 0.5 to 1 hour before quenching with water and excess inorganic base to produce a carbonyl derivative of formula XXI.

In Reaction Scheme VIII, step (r), a carbonyl derivative of formula XXI is reacted with an amine of formula XXII to form a Schiff's base which is reduced in the presence of an appropriate reducing agent to produce an amine of formula IIIa in either a one step or two step process. For example, a compound of formula XXI is treated with a large excess of an amine of formula XXII and an equivalent amount of a weak organic acid, for example acetic acid, in the presence of a reducing agent such as sodium cyanoborohydride in a suitable solvent, preferably a lower alkanol, for example methanol, at room temperature until the starting material is consumed. Alternatively, an amine of formula XXII and a carbonyl derivative of formula XXI heated together in aromatic solvent in an apparatus fitted with a water separator until water formation is complete. The resulting Schiff's base can be hydrogenated over a suitable catalyst, preferably Raney nickel, at a hydrogen pressure of from one to five atmospheres to give a compound of formula IIIa. When $R_6$ is not hydrogen and $R_5$ is chiral, the resulting amine IIIa may be enriched in one diastereomer over the other. For example, when $R_5$ is a chiral benzyl group, for example, R-alpha-methylbenzyl, and $R_6$ is lower alkyl, for example, methyl, the compound of formula IIIa may be diastereomerically enriched, and the chiral benzyl moiety may be removed, for example by hydrogenation over palladium on carbon to give an enantiomerically enriched amine of formula IIIa, $R_5$=hydrogen and $R_6$=lower alkyl. The compounds of formula IIIa can be isolated utilizing conventional methods, for example, extraction followed by distillation, crystallization of their acid addition salts, chromatography or the like.

In Reaction Scheme VIII, step (s), an azide of formula IVa is dissolved in a solvent, preferably a lower alkanol, and hydrogenated at a hydrogen pressure of from one to five atmospheres over a nobel metal catalyst, for example, palladium on carbon or platinum oxide, until the theoretical amount of hydrogen is consumed. The resulting compounds of formula IIIa can be isolated utilizing conventional methods, for example, distillation, crystallization of their acid addition salts, chromatography or the like. This transformation proceeds without alteration of the chirality of the carbon atom of bearing the azido group in a compound of formula IVa.

REACTION SCHEME IX

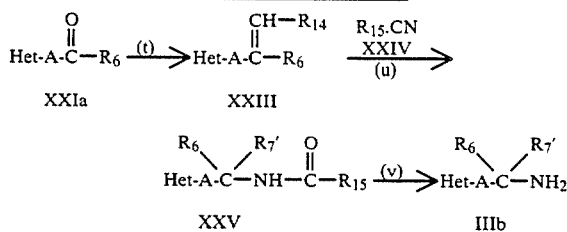

compounds of formula XXV can be isolated utilizing conventional methods, for example, distillation, crystallization, chromatography or the like.

In Scheme IX, step (v), a compound of formula XXV is hydrolyzed to an amine of formula IIIb. This process is advantageously carried out where $R_{15}$ is 2-nitrobenzyl by catalytic reduction of the nitro group for example over palladium on carbon at one atmosphere hydrogen pressure, and heating of the residue in the absence of solvent or in the presence of a solvent, for example acetic acid. The resulting compounds of formula IIIb can be isolated utilizing conventional methods, for example, distillation, crystallization of their acid addition salts, chromatography or the like.

REACTION SCHEME X

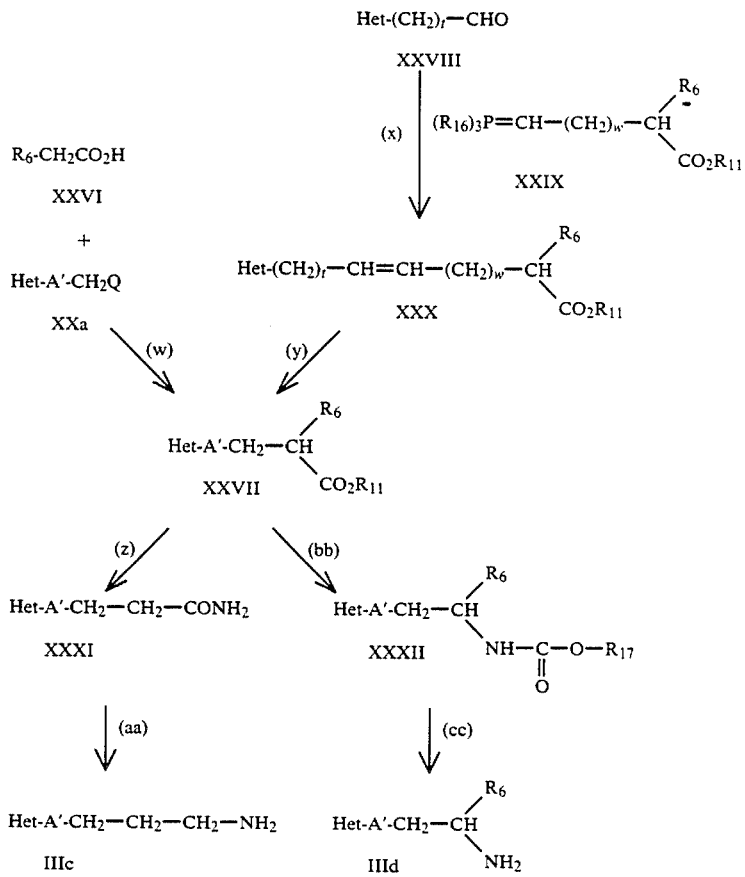

wherein Het, A and $R_6$ are as previously described, $R_{7'}$ is lower alkyl, $R_{14}$ is hydrogen or lower alkyl, and $R_{15}$ is alkyl or aryl.

In Reaction Scheme IX, step (t), a carbonyl derivative of formula XXIa is treated with an alkylidene triarylphosphorane in an inert solvent, preferably tetrahydrofuran, dimethylsulfoxide or diethyl ether, at a temperature of from $-80°$ C. to room temperature. The resulting compounds of formula XXIII can be isolated utilizing conventional methods, for example, distillation, chromatography or the like.

In Reaction Scheme IX, step (u), a nitrile of formula XXIV is reacted with a compound of formula XXIII in the presence of a strong mineral acid, preferably sulfuric acid and a small amount of water. The resulting wherein Het, $R_6$, A', Q and t are as previously described, and $R_{11}$ is hydrogen or lower alkyl, $R_{16}$ and $R_{17}$ independently, are, alkyl or aryl, and w is an integer of 0 to 3.

In Reaction Scheme X, step (w), the dilithium salt derived from a compound of formula XXVI, for example by treatment with lithium diisopropyl amide, is reacted with a compound of formula XXa in a suitable inert solvent, for example tetrahydrofuran, to give a compound of formula XXVII, $R_{11}$=hydrogen. The resulting compounds of formula XXVII can be isolated utilizing conventional methods, for example, crystallization, chromatography or the like.

Compounds of formula XXVII in which $R_6$ is non-hydrogen, and $R_{11}$ is hydrogen, may be resolved into their enantiomers by conversion to salts of chiral, enantiomertically pure amines, for example cinchonine, brucine, alpha-methylbenzylamine or the like. The pure diasteromeric salts are obtained by fractional crystallization from an appropriate solvent, for example a lower alkanol. The chiral, enantiomerically pure acids of formula XXVII, $R_{11}$=hydrogen may be recovered from their salts by conventional means, for example extraction from an aqueous, basic solution.

In Reaction Scheme X, step (x), a heteroaromatic carboxaldehyde of formula XXVIII, is reacted with a (carboxy)akylidenetriarylphosphorane of formula XXIX in a suitable solvent, for example tetrahydrofuran, dichloromethane, methanol or dimethylsulfoxide, to give a compound of formula XXX. The resulting compounds of formula XXX can be isolated utilizing conventional methods, for example, crystallization, distillation, chromatography or the like.

In Reaction Scheme X, step (y), a compound of formula XXX is hydrogenated over a suitable catalyst, for example, palladium on carbon or platinum oxide, in a suitable solvent, for example, a lower alkanol, at a hydrogen pressure of from one to five atmospheres until the theoretical amount of hydrogen is taken up to give a compound of formula XXVII.

In Reaction Scheme X, step (z), a compound of formula XXVII is converted into an amide of formula XXXI using conventional techniques for the conversion of carboxylic acids and esters into the corresponding primary amide. For example, a compound of formula XXVII, $R_{11}$=hydrogen may be converted to the corresponding acid chloride by treatment with thionyl chloride and then treated with an excess of ammonia to give a compound of formula XXXI. Alternatively, a compound of formula XXVII, $R_{11}$=lower alkyl, may be converted into a compound of formula XXXI by treatment with excess ammonia, optionally in the presence of co-solvent, for example, a lower alkanol, at a temperature of from $-33°$ C. to room temperature. The reaction may be run in a pressure vessel when appropriate.

In Reaction Scheme X, step (aa), a compound of formula XXXI is treated with a reducing agent, for example borane in tetrahydrofuran at a temperature of from room temperature to the reflux temperature of the solvent for 4 to 24 hours or until reduction is complete to give a compound of formula IIIc. The resulting compounds of formula IIIc can be isolated utilizing conventional methods, for example, by destruction of the excess reagent with a lower alkanol, followed by treatment with a mineral acid, for example, hydrochloric acid, basification, evaporation of the solvent and extraction of the product into a suitable organic solvent, for example, dichloromethane and purified by distillation, chromatography or the like.

In Reaction Scheme X, step (bb), an acid of formula XXVII, $R_{11}$=hydrogen, which may be obtained from the corresponding ester by hydrolysis, is subjected to conditions leading to a Curtius rearrangement in the presence of a lower alkanol. In a preferred procedure, an acid of formula XXVII (R=hydrogen), is treated with one equivalent of diphenylphosphorylazide in the presence of a proton acceptor, for example triethylamine or the like, and an excess of a lower alkanol or a phenol to give a compound of formula XXXII. The resulting compounds of formula XXXII can be isolated utilizing conventional methods, for example, crystallization, chromatography or the like.

In Reaction Scheme X, step (cc), a compound of formula XXXII is treated with an excess of a mineral acid in water optionally in the presence of a co-solvent, for example a lower alkanol, at a temperature of from room temperature to 100° C. or with a strong base in water, optionally in the presence of a co-solvent, for example a lower alkanol at a temperature of between 60° and 100° C. to form a compound of formula IIId. The resulting compounds of formula IIId can be isolated utilizing conventional methods, for example, crystallization of their acid addition salts, distillation, chromatography or the like.

REACTION SCHEME XI

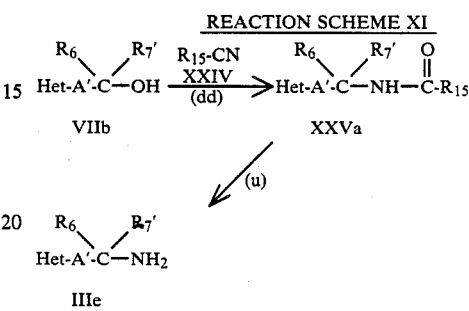

wherein Het, A', $R_6$, $R_7$, and $R_{15}$, are as previously described.

In Reaction Scheme XI, step (dd), an alcohol of formula VIIb is reacted with a nitrile of formula XXIV in the presence of a mineral acid, for example sulfuric acid, and water at a temperature of from $-20°$ C. to room temperature to give a compound of formula XXVa. The compound of formula XXVa can be isolated by conventional means, for example chromatography, crystallization or the like.

In Reaction Scheme XI, step (u), is the same as step (u) in Reaction Scheme IX to give a compound of formula IIIe. The compound of formula IIIe can be isolated by conventional means, for example, chromatography, crystallization or its acid addition salts, distillation or the like.

REACTION SCHEME XII

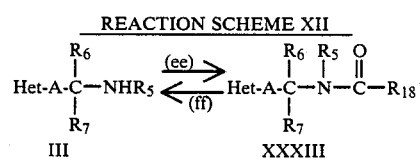

wherein Het, A, $R_5$, $R_6$ and $R_7$ are as previously described, $R_{18}$ is a chiral moiety, for example, a bonded chain lower alkyl or lower alkyl substituted with one or two groups selected from hydroxy, lower alkoxy, lower alkylcarbonyloxy, perfluoroalkyl, or aryl.

Those compounds of formula III which are chiral may be resolved into their enantiomers by conversion to salts of chiral acids, for example, dibenzoyltartaric acid and crystallization from an appropriate solvent, for example, a lower alkanol until pure diastereomers are obtained. The chiral, enantiomerically pure amines of formula III may be recovered by extraction from a basic aqueous solution and distillation or the like.

Alternatively, as shown in Reaction Scheme XII, step (ee), those compounds of formula III which are chiral may be resolved into their enantiomers by conversion to amides of chiral, enantiomerically pure acids using common techniques of peptide coupling. For example, a chiral amine of formula III may be coupled with a chiral, enantiomerically pure acid, for example (R)-mandelic acid, in the presence of a suitable coupling reagent, for example, dicyclohexylcarbodiimide optionally in the presence of a promoter, for example 1-hydroxybenzotriazole in a polar, aprotic solvent, for example dimethylformamide to give an amide of formula XXXIII. Amides of formula XXXIII may be separated into pure diastereomers by fractional crystallization, chromatography or the like.

In Reaction Scheme XII, step (ff), enantiomerically pure compounds of formula III may be recovered by hydrolysis of diastereomerically pure amides of formula XXXIII, for example with an aqueous mineral acid at a temperature of from 60° to 120° C.

The compounds of formula I can form acid addition salts with inorganic or organic acids. Thus, they form pharmaceutically acceptable acid addition salts with both pharmaceutically acceptable organic and inorganic acids, for example, with hydrohalic acids, such as, hydrochloric acid, hydrobromic acid, hydroiodic acid, other mineral acid salts, such as, sulfuric acid, nitric acid, phosphoric acid, perchloric acid or the like, alkyl and mono-aryl sulfonic acids such as, ethanesulfonic acid, toluenesulfonic acid, benzenesulfonic acid, or the like, other organic acids such as tartaric acid, maleic acid, citric acid, salicylic acid, ascorbic acid and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I, enantiomers or salts thereof have activity as platelet Activating Factor (PAF) antagonists and are, therefore, useful in amiliorating disease states characterized by excess platelet activating factor. For example they are useful in the prevention and treatment of cardiovascular diseases, pulmonary diseases, inflammatory diseases, immunological disorders, dermatological disorders, shock or transplant rejection.

The useful activity of the compounds of formula I can be demonstrated by the following procedures:

Binding Assay (a) Assay

The binding assay was performed in 400 $\mu$l polyethylene microcentrifuge tubes (Beckman) containing 50 $\mu$l of an oil mixture of 2 parts Siliconol AR200 (Serva): 1 part Silicone Fluid (Arthur H. Thomas). Buffer, standards, or analogs 150 $\mu$l total volume) were added to the tubes. Radiolabelled $^3$H-PAF (50 $\mu$l) was then added to the tubes. The reaction was started by the addition of 50 $\mu$l of dog platelets ($2 \times 10^7$ platelets). The tubes were capped, inverted several times to mix, and incubated for 10 minutes at room temperature. The platelets were separated from the incubation mixture by centrifuging 1 minute in a Beckman Microfuge B centrifuge. The tip of the microfuge tube was cut off, and the platelets were washed out of the tip with 200 $\mu$l of 50% methanol (Burdick and Jackson). Aquasol (NEN, 10 ml) was added and the radioactivity in the samples was determined using an LS 8100 Beckman liquid scintillation counter linked to a Techtran tape recorder. Data was processed through an in-house computer system. Alternatively, radioactivity was determined using a Searle Mark III liquid scintillation counter linked to a Iso-Data microprocessor. Results are set forth in Table I.

(b) Preparation of Platelets

Blood was collected from anesthesized or unanesthesized dogs into 5ml plastic centrifuge tubes containing 3.8% sodium citrate as the anticoagulant (1 volume of citrate/9 volumes of blood). The red cells were removed by centrifugation for 15 minutes at 600 rpm (100-125 g) at room temperature. An aliquot of the supernatant platelet rich Plasma (PRP) was saved for cell counting and the remainder was acidified to pH 6.5 with 0.15M citric acid. The platelet pellet was obtained after a 10 minute centrifugation at 2000 rpm (1000 g) at room temperature. Washed platelets were prepared by resuspending the platelet pellet once with PBS containing 1 mM EDTA, centrifuging as noted, and then resuspending the platelets in 0.1% BSA-PBS. An aliquot of the washed platelets was counted, platelets used for binding assays were diluted to $2 \times 10^7$ platelets/assay tube ($4 \times 10^8$ platelets/ml). Platelet counting was done using a Royco Cell-Crit 921.

PAF-Induced Bronchoconstriction Assay

The in vivo ability of compounds to inhibit PAF-induced bronchoconstriction in guinea pigs was assessed by the intravenous and oral routes of administration. The intravenous technique utilized male guinea pigs (Hartley strain, Charles River) weighing 400–600 g. Animals were anesthetized with urethane (2 g/kg) intraperitoneally and a polyethylene cannula was inserted into the jugular vein for intravenous drug administration. Tracheal pressure (cm of H$_2$) was recorded from a Statham pressure transducer (P 32 AA). Propranolol was administered 5 minutes prior to challenge with PAF. Two minutes later spontaneous breathing was arrested with succinylcholine chloride (1.2 mg/kg) administered intravenously, and the animals were ventilated with a Harvard (Model 680) small animal respirator set at 40 breaths/min and 4.0 cc stroke volume. Control vehicle or test drug was administered through the cannula into the jugular vein 1 minute before the animals were challenged with a maximum constrictory dose of PAF (1.0 $\mu$g/kg) given intravenously. The change in tracheal pressure was averaged for four control and four drug-treated animals and percent inhibition was calculated.

For determination of oral activity, animals were dosed with test compound or vehicle two hours prior to challenge with PAF (1.0 $\mu$g/kg, i.v.).

The change in tracheal pressure is determined by subtracting the steady state baseline achieved after administration of succinylcholine from the peak bronchoconstriction seen after challenge with PAF. The mean change in tracheal pressure is calculated for each test compound and compared to the mean change in tracheal pressure for the control animals to give the percent inhibition of bronchoconstriction. The standard error is calculated as the standard error of the mean.

PAF-Induced Platelet Count Decrease

Male Hartley guinea pigs weighing between 500 and 900 grams were fed standard guinea pig chow and tap water ad libitum. PAF was solubilized in ethanol and stored as a 2 mM stock solution at −70° C. The stock solution of PAF was diluted to 1 PM in Tris buffer pH 7.4 and 0.1% BSA for all experiments.

(a) Intravenous Procedure

Guinea pigs were anesthetized with urethane (1.6 g/kg, i.p.). A catheter (PE50) was introduced into the right carotid artery for withdrawing blood. A second catheter PE10) was introduced into the jugular vein for injecting drugs and for administering the PAF challenge (75 ng/kg, i.v.). A control blood sample was obtained and platelets were counted in a whole blood platelet analyzer. PAF was then given and blood samples were taken 15, 30, and 60 seconds after the challenge for platelet counts. Fifteen minutes later, selected concentrations of the test compound were solubilized in DMSO and injected intravenously into a group of 4–6 animals. Only one concentration of the test drug was used in each animal group. Fifteen minutes after drug injection, blood samples were taken before and 15, 30, and 60 sec after the PAF challenge, and analyzed for platelet number.

(b) Oral Procedure

Animals were anesthetized with sodium pentobarbital (35 mg/kg. i.p.) and the carotid artery and jugular vein were cannulated as described above. The cannulae were exteriorized at the base of the neck and the animals were allowed to recover. Conscious, unrestrained guinea pigs which were allowed to recover from surgery for at least 18 hours were used in the experiments. The animals were challenged two times with PAF (120 ng/kg, i.v.); the first to establish a consistent response to PAF and the second to serve as a control from the PAF challenge. Blood samples were taken before and 15, 30, and 45 seconds after PAF challenge and platelets were counted. Thirty minutes after the control PAF challenge, the animals were orally dosed with either gum acacia or the test compound. Animals were then challenged with PAF at 1, 3, 5, and 24 hours after the administration of the drug.

Data Analysis and Statistics

The % change, i.e., the difference in platelet number before and after PAF challenge was calculated by:

% change =

$$\frac{\# \text{ control platelets (0 Time)} - \text{lowest } \# \text{ of platelets after } PAF}{\# \text{ of control platelets (0 Time)}}$$

The % activity of drug was then determined by $$\% \text{ activity} = \frac{\% \text{ change (control)} - \% \text{ change (drug)}}{\% \text{ change (control)}}$$

Statistical significance ($p \leq 0.05$) of the difference between the mean PAF control and mean drug treated activity was determined with the pared Students's t-test.

The compounds of formula I also have Thromboxane Synthase ($TXA_2$ Syn.) Inhibitory Activity, which can be demonstrated as follows.

$TXA_2$ Synthesis Inhibition

Thromboxane synthase inhibitory activity is measured by following the conversion of $^{14}C$-thromboxane $A_2$ ($TXA_2$) using microsomal fractions from human platelets as enzyme source. In the aqueous incubation medium. The $TXA_2$ decomposes rapidly into $TXB_2$. The amount of $TXA_2$ syn. is adjusted so that under the conditions of the assay approximately 80–90% of the substrate. $PGH_2$, is converted to product in control tubes. To prepare $^{14}C$-$PGH_2$, $^{14}C$-AA(50–60mCi/mmole; Rose Chem.) is incubated with sheep seminal vesicular gland microsomes for 1.5 min. at 37° and then the $^{14}C$-$PGH_2$ is extracted with diethylether, purified on columns of Sephadex LH-20 or silicic acid, and stored in acetone at $-70°$ C. Incubations are done as follows. Sufficient $^{14}C$-$PGH_2$ to yield a final substrate concentration of 10 $\mu M$ ( 30,000 cpm) is added to the incubation tubes and then the acetone is removed under nitrogen. The tubes are placed in an ice bath and then 215 $\mu l$ of ice cold phosphate buffered saline, 10 $\mu$of ethanol (control) or of test drug in ethanol, and 25 $\mu l$ of the microsomal suspension are added with mixing in that order as rapidly as possible. The tubes are incubated at 22° for 2 minutes, the reaction is stopped and then the radioactive products and the unconverted $PGH_2$ are extracted and analyzed by thin layer chromatography. The amount of $^{14}C$-$PGH_2$ converted to products is analyzed by thin layer chromatography. The amount of $^{14}C$-$PGH_2$ converted to products was used as a measure of TXA synthase activity. Inhibitors were tested initially at a concentration of 100 $\mu M$. $IC_{50}$ values were calculated by linear regression analysis of successive 10 fold dilutions of the test compound concentration.

Test results obtained with compounds of formula I in the described tests are set forth in Table I which follows:

TABLE I

| Compound | PAF Binding $IC_{50}$ nM | $TXA_2$ Syn. Inhibition $IC_{50}$ nM | PAF-Induced Platelet Count Decrease % Inhibition | | PAF-Induced Bronchoconstriction % Inhibition | |
|---|---|---|---|---|---|---|
| | | | i.v.[a] | po | 1 mg/kg iv[d] | 50 mg/kg, po[f] |
| 3',4'-Dimethyl-N-[6-(3-pyridinyl)hexyl][1,1'-biphenyl]-4-carboxamide | 450 | 600 | 27 | | | |
| N-[4-(3-Pyridinyl)butyl]-[1,1'-biphenyl]-4-carboxamide | 630 | 100 | | | 42 ± 7 | |
| 3'-Methoxy-N-[4-(3-pyridinyl)butyl][1,1'-biphenyl]-4-carboxamide | 280 | 25 | | | 70 ± 10 | 55 ± 17 |
| (R)-3'-Methoxy-N-[1-methyl-4-(3-pyridinyl)butyl]-[1,1'-biphenyl]-4-carboxamide | 20 | | 17 | | | |
| 3'-Hydroxy-N-[4-(3-pyridinyl)-butyl][1,1'-biphenyl]-4-carboxamide | 300 | <100 | | | | |
| 3',4'-Dimethyl-N-[4-(3- | 700 | 125 | | | | |

TABLE I-continued

| Compound | PAF Binding IC$_{50}$ nM | TXA$_2$ Syn. Inhibition IC$_{50}$ nM | PAF-Induced Platelet Count Decrease % Inhibition i.v.[a] | po | PAF-Induced Bronchoconstriction % Inhibition 1 mg/kg iv[d] | 50 mg/kg, po[f] |
|---|---|---|---|---|---|---|
| pyridinyl)butyl][1,1-biphenyl]-4-carboxamide | | | | | | |
| (rac.)-3',4'-Dimethyl-N-[1-methyl-4-(3-pyridinyl)butyl][1,1'-biphenyl]-4-carboxamide | 200 | 100–1000 | 12 | | | |
| (rac.)-3',4'-Dimethoxy-N-[1-methyl-4-(3-pyridinyl)butyl][1,1'-biphenyl]-4-carboxamide | 50 | | 26 | 75 ± 21 | | |
| (R)-3',4'-Dimethoxy-N-[1-methyl-4-(3-pyridinyl)butyl][1,1'-biphenyl]-4-carboxamide | 15 | | | | 65 ± 11 | 88 ± 3 |
| (rac.)-3'-Methoxy-N-(1-methyl-4-(3-pyridinyl)butyl][1,1'-biphenyl]-4-carbothioamide | 120 | 100–1000 | 6 | | 16 ± 14 | |
| 3',4'-Dimethoxy-N-[4-(3-pyridinyl)butyl][1,1'-biphenyl]-4-carbothioamide | 140 | 225 | 15 | 53[b] | | |
| rac.-3',4'-Dimethoxy-N-[1-methyl-4-(3-pyridinyl)butyl][1,1'-biphenyl]-4-carbothioamide | 60 | 100–1000 | 24 | 48[c] | 86 ± 7 | 37 ± 9 |
| 3',4'-Dimethyl-N-[4-(3-pyridinyl)butyl][1,1-biphenyl]-4-carbothioamide | 600 | | | | potentiation | |
| rac.-3',4'-Dimethyl-N-[1-methyl-4-(3-pyridinyl)butyl][1,1'-biphenyl]-4-carbothioamide | 110 | | 28 | | 4 ± 4 | |
| 3',4'Dimethoxy-3,5-dimethyl-N-[4-(3-pyridinyl)butyl][1,1'-biphenyl]-4-carboxamide | 60 | | 14 | | 17 ± 11 | |
| 3-[4-[5-(3',4'-Dimethyl-[1,1'-biphenyl]-4-yl)-1H-tetrazol-1-yl]butyl]pyridine | 800 | >1000 | | | 57 ± 4 | |
| 3-[6-[5-(3',4'-Dimethyl-[1,1'-biphenyl]-4-yl)-1H-tetrazol-1-yl]hexyl]pyridine | 200 | 100–1000 | 0 | | 18 ± 13 | |
| 3-[3-[5-(3',4'-Dimethyl-[1,1'-biphenyl]-4-yl)-2H-tetrazol-2-yl]propyl]pyridine | >1000 | | | | 11 ± 3 | |
| 3-[4-[5-(3',4'-Dimethyl-[1,1'-biphenyl]-4-yl)-2H-tetrazol-2-yl]butyl]pyridine | >1000 | | | | 17 ± 15 | |
| 3-[6-[5-(3',4'-Dimethyl-[1,1'-biphenyl]-4-yl)-2H-tetrazol-2-yl]hexyl]pyridine | >1000 | | | | 40 ± 4 | |
| 3,4-Dibutyl-N-[4-(3-pyridinyl)butyl]benzamide | >1000 | | | | | |
| 2-Butyl-N-[4-(3-pyridinyl)butyl][1,1'-biphenyl]-4-carboxamide | 500 | | | | 27 ± 10 | |
| 2-Propyl-N-[4-(3-pyridinyl)butyl][1,1'-biphenyl]-4-carboxamide | 60 | | | | 38 ± 8 | |
| 2-Butyl-3',4'-dimethoxy-N-[4-(3-pyridinyl)butyl][1,1'-biphenyl)-4-carboxamide | 18 | | | | 6 ± 4 | |
| (R)-2-Butyl-3',4'-dimethoxy-N-[1-methyl-4-(3-pyridinyl)butyl][1,1'-biphenyl]-4-carboxamide | 4 | | | | 55 ± 12 | |
| (R)-2-Propyl-N-[1-methyl-4-(3-pyridinyl)-butyl]-[1,1'-biphenyl]-4-carboxamide | 50 | | | | 12 ±6 | |
| 3,4-Diphenyl-N-[4-(3-pyridinyl)butyl]-benzamide | 5 | | 49 | | 21 ± 4 | 33 ± 12 |

TABLE I-continued

| Compound | PAF Binding IC$_{50}$ nM | TXA$_2$ Syn. Inhibition IC$_{50}$ nM | PAF-Induced Platelet Count Decrease % Inhibition | | PAF-Induced Bronchoconstriction % Inhibition | |
|---|---|---|---|---|---|---|
| | | | i.v.[a] | po | 1 mg/kg iv[d] | 50 mg/kg, po[f] |
| (R)-3,4-diphenyl-N-[1-methyl-4-(3-pyridinyl)-butyl]benzamide | 250 | | | | 31 ± 4 | |
| 3,4-bis-(3-Methoxyphenyl)-N-[4-(3-pyridinyl)butyl]-benzamide | 200 | | 4 | | 12 ± 6 | |
| 3,4-bis-(3-Fluorophenyl)-N-[4-(3-pyridinyl)butyl]-benzamide | 400 | | | | 12 ± 2 | |
| 3,4-bis-(4,Methoxyphenyl)-N-[4-(3-pyridinyl)butyl]-benzamide | 125 | | | | 26 ± 6 | |
| 2-Bromo-3',4'-dimethoxy-N-[4-(3-pyridinyl)butyl]-[1,1'biphenyl]-4-carboxamide | 200 | | | | 81 ± 10 | 74 ± 12 |
| (R)-2-Bromo-3',4'-dimethoxy-N-[1-methyl-4-(3-pyridinyl)-butyl][1,1'-biphenyl]-4-carboxamide | 180 | | | | 98 ± 0.7 | 97 ± 1 |
| 2-Nitro-3',4'-dimethoxy-N-[4-(3-pyridinyl)-butyl][1,1'-biphenyl]-4-carboxamide | 200 | | | | 81 ± 15 | 62 ± 15 |
| (R)-2-Nitro-3',4'-dimethoxy-N-[1-methyl-4-(3-pyridinyl)-butyl][1,1'-biphenyl]-4-carboxamide | 200 | | | | 97 ± 4 | 89 ± 8 |
| (R)-2-Ethynyl-3',4'-dimethoxy-N-[1-methyl-4-(3-pyridinyl)-butyl][1,1'-biphenyl]-4-carboxamide | 5.0 | | | | | |
| 2,3',4'-trimethoxy-N-[4-(3-pyridinyl)butyl]-[1,1'-biphenyl]-4-carboxamide | 300 | | | | 58 ± 10 | |
| N-[4-(3-pyridinyl)butyl][1,1'-biphenyl]-3-carboxamide | 620 | | | | 14 ± 10 | |
| 4-Cyclohexyl-N-[4-(3-pyridinyl)butyl]-benzamide | 250 | | | | 17 ± 7 | |
| (R)-2-Ethyl-3',4'-dimethoxy-N-[1-methyl-4-(3-pyridinyl)butyl][1,1'-biphenyl]-4-carboxamide | 4.0 | | | | 93 ± 1 | 89 ± 5 |
| (R)-3',4'-Dimethoxy-N-[1-methyl-4-(3-pyridinyl)butyl]-2-propyl-[1,1'-biphenyl]-4-carboxamide | 50 | | | | 28 ± 12 | |
| (R)-3',4'-Dimethoxy-N-[1-methyl-4-(3-pyridinyl)butyl]-2-(2-propenyl)-[1,1'-biphenyl]-4-carboxamide | 80 | | | | 80 ± 11 | 93 ± 3 |

[a] 3 mg/kg, iv; 15 minutes pretreatment time
[b] 100 mg/kg, po, 3 hours, pretreatment
[c] 30 mg/kg, po, 2 hours, pretreatment
[d] 1 minute pretreatment
[e] 5 minutes pretreatment
[f] 2 hours pretreatment A compound of formula I, an enantiomer thereof or a salt thereof or a composition containing a therapeutically effective amount of a compound of formula I, an enantiomer thereof or a salt thereof can be administered by methods well known in the art. Thus a compound of formula I an enantiomer thereof or a salt thereof can be administered either singly or with other pharmaceutical agents for example antihistamines, mediator release inhibitors, methyl xanthines, beta agonists or antiasthmatic steroids such as prednisone and prednisolone, orally. Parenterally, rectally or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

Since the compounds of formula I of the invention may possess an asymmetric carbon atom, they may be obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, with an optically active resolving agent, for example, an optically active acid, such as D-(+)-benzoyltartaric acid, which can be reacted with a basic group. The formed diastereomers are separated by selective crystallization and converted to the corresponding optical isomer. Thus, the invention covers the racemates of the compounds of formula I as well as their optically active isomers (enantiomers).

The examples which follow also further describe the invention. All temperatures given are in degree centigrade unless otherwise stated.

EXAMPLE 1

N-4-(3-Pyridinyl)buty][1,1'-biphenyl]-4-carboxamide (Method A)

A suspension of 5.0 g of biphenyl-4-carboxylic acid in 20 mL of dichloromethane and 0.5 mL of DMF was treated with 2.1 mL of thionyl chloride and the resulting mixture was heated to reflux until a clear solution was obtained. The mixture was cooled to room temperature and 7.8 g of 3-pyridinebutanamine was slowly added. The reaction mixture was stirred for 10 minutes. was diluted with 150 mL of dichloromethane and was washed with 50 mL of 1N sodium hydroxide. The organic layer was dried over potassium carbonate and evaporated and the residue was crystallized from ethyl acetate-hexane with a charcoal treatment to yield 5.0 g (61%) of N-[4-(3-pyridinyl)butyl][1,1'-biphenyl]-carboxamide, mp 122.5°-126° C. The hydrochloride salt was recrystallized from isopropanol-ether, mp 158°-160° C.

EXAMPLE 2

3'-(phenylmethoxy)-N-[4-(3-pyridinyl)butyl][1,1'-biphenyl]4-carboxamide (Method B)

To a suspension of 7.9 g of 3'-benzyloxy[1,1'-biphenyl]-4-carboxylic acid in 50 mL of toluene was added a solution of 6.8 mL of oxalyl chloride in 20 mL of toluene. The mixture was heated to reflux for 18 hours, and the toluene was evaporated on a rotary evaporator using a vacuum pump. The residue was dissolved in 40 mL of dry dichloromethane and a solution of 5.08 g of 3-pyridinebutanamine in 20 mL of dry pyridine was added dropwise. The mixture was heated to reflux for 18 hours, was concentrated, and purified by preparative hplc eluting with 95:5 dichloromethane-methanol to give 7.8 g (69%) of 3'-(Phenylmethoxy)-N-[4-(3-pyridinyl) butyl][1,1'-biphenyl]-4-carboxamide as a light yellow oil.

EXAMPLE 3

Rac.-3',4'-Dimethyl-N-[1-methyl-4-(3-pyridinyl)-butyl][1,1'-biphenyl]-4-carboxamide (Method C)

A solution of 50 g of 3',4'-dimethyl[1,1'-biphenyl]-4-carboxylic acid in 200 mL of DMF was cooled in an ice bath and 5.2 mL of diphenylphosphoryl azide was added. After 20 minutes, 3.9 mL of triethylamine was added, and after a further hour, 4.0 g of rac. alpha-methyl-3-pyridinebutanamine was added and the mixture was allowed to warm to room temperature over night. The solvent was evaporated, the residue was taken up in dichloromethane and washed with water and bicarbonate, dried (MgSO4), and purified by preparative hPlc eluting with 95:5 dichloromethane-methanol to give 4.1 g (65%) of rac.-3',4'-dimethyl-N-[1-methyl-4-(3-pyridinyl)butyl][1,1'-biphenyl]4-carboxamide, mp 118°-120° C. after recrystallization from ethyl acetate-hexane. The analytical sample was obtained from ethyl acetate. mp 120°-121° C.

EXAMPLE 4

3',4'-Dimethyl-N-[6-(3-pyridinyl)hexy11[1.1'-biphenyl]-4-carboxamide

The title compound was prepared from 7.0 g of 3',4'-dimethyl[1,1'-biphenyl]-4-carboxylic acid and 6.1 g of 3-pyridinehexanamine according to Example 3 to give 6.2 g of 3,'4'-dimethyl-N-[6-(3-pyridinyl)hexyl][1,1'-biphenyl]-4-carboxamide. mp 81°-82° C.

EXAMPLE 5

3,4-Diphenyl-N-[4-(3-pyridinyl)butyl]benzamide 0.25 molar hydrate

To an ice-cooled solution of 0.508 g 1.85 mmol) of 3,4-diphenylbenzoic acid in 10 mL of anhydrous DMF was added 0.44 mL of diphenylphosphoryl azide with stirring. Triethylamine (0.28 mL) was then added and stirring at 3° C. 0 was continued for 1 hour. 3-pyridinebutanamine (0.309 g) was added and stirring was continue for 30 minutes at 3° C. and for 17 hours at room temperature. The solvent was removed under the oil pump vacuum and ethyl acetate was added to the residue. The solution was washed with aqueous 5% sodium bicarbonate. dried (MgSO4) and concentrated in vacuo. The residual oil was chromatographed on 50 g of silica gel, eluting with methylene chloride-methanol-conc.ammonium hydroxide (95:5:0.05). The pure fractions were combined and lyophilized from benzene to yield a 0.708 g of 3,4-Diphenyl-N-[4-(3-pyridinyl)butyl]benzamide 0.25 molar hydrate as a colorless foam.

EXAMPLE 6

3'Hydroxy-N-[4-(3-pyridinyl)butyl][1,1'-biphenyl]-4-carboxamide (Method D)

A solution of 7.8 g of 3'-(phenylmethoxy)-N-[4-(3-pyridinyl)butyl][1,1'-biphenyl]-4-carboxamide in 150 mL of ethanol was hydrogenated over 0.8 g of 10% palladium on carbon. The product was crystallized from acetonitrile to give 3.6 g of 3'-hydroxy-N-[4-(3-pyridinyl)butyl][1,1'-biphenyl]-4-carboxamide mp 150°-151.5° C. The analytical sample was obtained from acetonitrile, mp 151.5°-152.5° C.

EXAMPLE 7

3',4'-Dimethyl-N-[4-(3-pyridinyl)butyl][1.1'-biphenyl]-4-carbothioamide (Method E)

A solution of 4.0 g of 3',4'-dimethyl-N-[4-(3-pyridinyl)butyl][1,1'-biphenyl]-4-carboxamide in 150 mL of dry pyridine and 2.7 g of phosphorous pentasulfide was heated to reflux for 1.5 hour and was evaporated to dryness. The residue was taken up in dichloromethane. washed repeatedly with water. dried, and purified by preparative hplc eluting with 95:5 dichloromethane-methanol to give 4.0 g of a yellow oil which was crystallized from ether affording 3.3 g (79%) of 3',4'-Dimethyl-N-[4-(3-pyridinyl)butyl][1.1'-biphenyl]-4-carbothioamide. mp 85°-86.5° C.

EXAMPLE 8

3',4'-Dimethoxy-3,5-dimethyl[1,1'-biphenyl]-4-carboxylic acid

A solution of 6.4 g of 3,4-dimethoxyacetophenone and 12.3 mL of morpholine in 100 mL of distilled toluene was cooled to −15° C. and a solution of 1.95 mL (17.8 mmol) of titanium tetrachloride in 50 mL of toluene was added dropwise. maintaining the temperature at <−10° C. Upon completion of the addition, the mixture was allowed to stand overnight, was filtered through a pad of celite and was evaporated to dryness with a rotary evaporator using an oil pump to give 8.8 g of crude enamine.

A mixture of 8.8 g of the above enamine and 7.41 g of ethyl isodehydracetate was heated rapidly to 140° C. and then slowly to 160° C. After 6 hours, the mixture was cooled to rom temperature and the resulting brown oil was dissolved in 150 mL of ether and washed with 50 mL of 1 N HCl. 50 mL of water. and 50 mL of brine. Drying and evaporation gave 8.5 g (85%) of ethyl 3',4'-Dimethoxy-3,5-dimethyl[1,1'-biphenyl]-4-carboxylate, mp 91°-92° C.

A suspension of 8.5 g of the above ester in 50 mL of 2 N NaOH and 100 mL of ethanol was heated to reflux over night. After cooling, the reaction mixture was poured onto ice and the precipitated starting material was collected. The filtrate was washed with ether acidified and extracted with ether, dried and evaporated to give 2.0 g of a white solid which was recrystallized from ethanol-water to give 1.4 g (16%) of 3',4'-dimethoxy-3,5-dimethyl[1,1'-biphenyl]4-carboxylic acid. mp 175°-176° then resolidifies, 186.5°-187° C.

EXAMPLE 9

3',4'-Dimethoxy-3,5-dimethyl-N-[4-(3-pyridinyl)butyl][1,1'-biphenyl]-4-carboxamide (Method F)

A solution of 0.50 g of 3',4'-dimethoxy-3,5-dimethyl[1,1'-biphenyl]-4-carboxylic acid in 10 mL of thionyl chloride was heated to reflux for 20 minutes, evaporated diluted with 10 mL of toluene and evaporated to dryness. The residue was suspended in 5 mL of DMF. treated with 0.51 g of 3-pyridinebutanamine and allowed to stir 30 minutes at 25° C. The reaction mixture was diluted to 50 mL with ethyl acetate, was washed water, dilute sodium hydroxide and brine, dried and evaporated. Chromatography over 50 g of silica gel eluting with ethyl acetate ad recrystallization of the product form ethyl acetate-hexane afforded 0.40 g (56%) of 3',4'-dimethoxy-3,5-dimethyl-N-[4-(3-pyridinyl)butyl][1,1'-biphenyl]-4-carboxamide, mp 117°-119° C.

EXAMPLE 10

3-(6-5-(3',4'-Dimethyl[1,1'-biphenyl]-4-yl)-1H-tetrazol-1-yl]hexyl]pyridine (Method G)

A mixture of 6.0 g of 3',4'-dimethyl-N-[6-(3-pyridinyl)hexyl][1,1'-biphenyl]-4-carboxamide and 4.2 g of phosphorous pentachloride in 300 mL of dry toluene was stirred over night at room temperature giving a two phase mixture to which 31.3 mL of 1.12M hydrazoic acid in toluene was added. After 1 hour at 25° C., the reaction mixture was heated to reflux for 3.5 hours, cooled and evaporated. The residue was taken up in ethyl acetate, washed with 1M NaOH and water, was dried and evaporated to give an oil which was crystallized from ethanol to give 2.0 g (30%) of 3-[6-[5-(3',4'-dimethyl[1,1'-biphenyl]-4-yl)-1H-tetrazol-1-yl]hexyl]pyridine, mp 101°-103° C. The mother liquor afforded an additional 0.6 g (9%), mp 101°-103° C. after chromatography. The analytical sample was obtained from ethanol, mp 102.5°-104° C.

EXAMPLE 11

3',4'-Dimethyl[1,1'-biphenyl]-4-carbonitrile

3',4'-Dimethyl[1,1'-biphenyl]-4-carbonitrile was prepared according to Method I starting with the aryl zinc species formed from 24.5 mL of 3,4-dimethylbromobenzene, 165 mL of 1.5M n-butyl lithium and 22.9 g of zinc chloride. 30 g of 4-bromobenzonitrile and 4.3 g of bis (triphenylphosphine) palladium dichloride to give 16.2 g of 3',4'-dimethyl[1,1'- biphenyl]-4-carbonitrile, mp 70°-71.5° C. after crystallization from ethyl acetate-hexane.

EXAMPLE 12

5-(3',4'-Dimethyl[1,1'-biphenyl]-4-yl)-1H-tetrazole

A suspension of 10.0 g of 3',4'-dimethyl[1,1'-biphenyl]-4-carbonitrile, 3.45 g of sodium azide and 2.8 g of ammonium chloride in 300 mL of DMF was heated to a bath temperature of 125° C. for 20 hours. The reaction mixture was cooled, filtered, and evaporated and the residue was taken up in ethyl acetate and washed with water. The residue obtained after drying and evaporation was crystallized from ethyl acetate-dichloromethane to give 4.6 g of 5-(3',4'-Dimethyl[1,1'-biphenyl]-4-

EXAMPLE 13

3-6-[5-(3',4'-Dimethyl[1,1'-biphenyl]-4-yl)-2H-tetrazol-2yl]hexyl]pyridine (Method H)

A solution of 3.5 g of 5-(3',4'-dimethyl[1,1'-biphenyl]4-yl)-1H-tetrazole. 2.8 g of 3-pyridinehexanol, and 4.0 g of triphenylphosphine in 100 mL of THF was cooled in an ice-salt bath and a solution of 2.4 mL of diethyl diazodicarboxylate in 25 mL of THF was added dropwise. The reaction mixture was allowed to warm to room temperature over night, the solvent was evaporated, the residue was taken up in ethyl acetate, washed with aqueous sodium bicarbonate and extracted with 1M HCl. The acid extract was made basic with NaOH solution and extracted with ethyl acetate. The combined organic layers afforded 4.22 g of a cream colored solid which was purified by hplc eluting with 1% triethylamine in ethyl acetate to give 2.4 g of 3-[6-[5-(3',4'-dimethyl[1,1'-biphenyl]-4-yl)-2H-tetrazol-2-yl]hexyl]-pyridine, mp 63°-64° C. after recrystallization from ethyl acetate.

EXAMPLE 14

3 3',4'-trimethoxy[1.1'-biphenyl]-4-carboxylic acid ester (Method I)

A solution of 9.3 mL of 4-bromoveratrole in 200 mL of THF was cooled to -78° C. and 73 mL of 1.51M n-butyl lithium was added dropwise. The reaction mixture was stirred for 3 hours at -78° C. and a solution of freshly fused zinc chloride in 100 mL of THF was added. After 1 hour, this solution was added to a second solution formed by treatment of a suspension of 1.7 g of bis(triphenylphosphine)palladium dichloride in 300 mL of THF with 4.9 mL of a 1M solution of diisobutylaluminum hydride in hexane followed by addition of 16.2 g of methyl 4-bromo-2-methoxybenzoate using a double tipped syringe needle. The reaction mixture was allowed to stir at room temperature over night and was diluted with ethyl acetate. The organic solution was washed with 1M HCl, water, and brine, dried, and evaporated to a dark oil which was purified by preparative hplc eluting with 3:1 hexane:ethyl acetate and crystallized from ethyl acetate-hexane to give 8.4 g 3,3',4'-trimethoxy[1,1'-biphenyl]-4-carboxylic acid methyl ester. mp 96°-97.5° C.

EXAMPLE 15

3,3',4'-Trimethoxy[1,1'-biphenyl]-4-carboxylic acid (Method J)

A solution of 8.4 g of methyl 3,3',4'-Irimethoxy[1,1'-biphenyl]-4-carboxylic acid methyl ester and 1.7 g of sodium hydroxide in 200 mL of ethanol was heated to reflux for 18 hours. The mixture was diluted with water, washed with ethyl acetate acidified with dilute HCl, and extracted with ethyl acetate. The combined extracts were dried, evaporated and crystallized from ethyl acetate to give 4.2 g (52%) of 3,3',4'-trimethoxy[1,1'-biphenyl]-4-carboxylic acid, mp 134°-135° C.

EXAMPLE 16

3,4-Diphenylbenzoic acid (Method M)

A solution of 3.3 g of methyl coumalate and 3.8 g of diphenylacetylene in 30mL of toluene was heated at 250° C. in a glass lined autoclave under 50 psi nitrogen pressure for 24 hours. The reaction mixture was concentrated under reduced pressure to an oil which was purified by chromatography on 300 g of silica gel, eluting with 10% ethyl acetate-hexane. The pure fractions were combined and recrystallized twice from methanol to give 1.6 g (26%), mp 125°-127° C. (reported mp 130°-131° C.; J. A. Reed, C. L. Schilling, R. F. Tarvin, T. A. Rettig and J. K. Stille, J. Org. Chem., 34, 2188(1969) of 3,4-diphenylbenzoic acid methyl ester.

A solution of 1.6 g of 3,4-diphenylbenzoic acid methyl ester in 50 mL of methanol and 11 mL of 1N sodium hydroxide was stirred at reflux for 15 hours. The solvent was removed under reduced pressure and the residue was acidified. The product was extracted with ethyl acetate and the dried extract was concentrated. Recrystallization of the resultant solid from ethyl acetate-hexane gave 1.3 g (82%). mp 218°-220° C., of 3,4-diphenylbenzoic acid.

EXAMPLE 17

3',4'-Dimethoxy-2-trimethylsilylethynyl[1,1'-biphenyl]-4-carboxylic acid methyl ester A solution of 702 mg of 2-bromo-3',4'-dimethoxy [1,1'-biphenyl]-4-carboxylic acid methyl ester in 7 mL of dimethylformamide and 2 mL of thiethylamine was deoxygenated with argon for 20 minutes and 0.50 mL of trimethylsilylacetylene followed by 70 mg of bis(triphenylphosphine) palladium dichloride were added all at once. The bath temperature was raised to 80°-85° C. for 2 hours and the mixture was allowed to cool. The dark solution was diluted with ethyl acetate and washed with water and saturated potassium carbonate solution, dried, and concentrated. The residue was chromatographed over 100 g of silica gel eluting with 4:1 hexane-ethyl acetate and recrystallized from hexane to afford 391 mg of 3',4'-dimethoxy-2-trimethylsilylethynyl[1,1'-biphenyl]-4-carboxylic acid methyl ester, mp 93°-96° C.

EXAMPLE 18

3',4'-Dimethoxy-2-(2-propenyl)[1,1'-biphenyl]-4-carboxylic acid methyl ester

A solution of 702 mg of 2-bromo-3',4'-dimethoxy[1,1'-biphenyl]-4-carboxylic acid methyl ester and 0.65 mL of allyltributyl tin in 6 mL of dimethylformamide was deoxygenated with argon and 70 mg of bis(triphenylphosphine) palladium dichloride was added. The bath temperature was raised to 100° C. for 1 hour and the mixture was allowed to cool. It was diluted with ethyl acetate and washed with water and saturated potassium carbonate, dried, and concentrated. The residue was chromatographed over 100 g of silica gel eluting with 4:1 hexane-ethyl acetate to give 602 mg of 3',4'-Dimethoxy-2-(2-propenyl)[1.1'-biphenyl]4-carboxylic acid methyl ester which solidified on drying, mp 99°-103° C.

Structure:

$R_2$, $R_3$ on benzene ring with $R_4$; C(=X)–NH–CHR_6–(CH_2)_n–pyridyl($R_8$)

| Example | $R_2$ | $R_3$ | $R_4$ | $R_6$ | X | n | $R_8$ | Method | Yield, % | mp, °C. | Recryst. Solvent | Empirical Formula |
|---|---|---|---|---|---|---|---|---|---|---|---|---|
| 19 | H | 3-F | H | H | O | 3 | H | B | 31 | 161-162 | EtOH—Et$_2$O | C$_{22}$H$_{21}$FN$_2$O.HCl |
| 20 | H | 3-CH$_3$ | H | H | O | 3 | H | B | 44 | 137-138 | EtOH—Et$_2$O | C$_{23}$H$_{24}$N$_2$O.HCl |
| 21 | H | 3-CH$_3$O | H | H | O | 3 | H | A | 89 | 113-114 | EtOH—Et$_2$O | C$_{23}$H$_{24}$N$_2$O$_2$.HCl |
| 22 | H | 3-CH$_3$O | H | CH$_3$[a] | O | 3 | H | A | 69 | Oil | | C$_{24}$H$_{26}$N$_2$O$_2$ |
| 23 | H | 3-CH$_3$O | H | CH$_3$[b] | O | 3 | H | C | 79 | 89-90 | EtOAc—Hex | C$_{24}$H$_{26}$N$_2$O$_2$ |
| 24 | H | 3,4-(CH$_3$)$_2$ | H | H | O | 3 | H | C | 65 | 95-98 | EtOAc—Hex | C$_{24}$H$_{26}$N$_2$O |

-continued

![structure: R2,R3,R4-substituted phenyl-C(=X)-NH-CHR6-(CH2)n-pyridyl-R8]

| Example | R2 | R3 | R4 | R6 | X | n | R8 | Method | Yield, % | mp, °C. | Recryst. Solvent | Empirical Formula |
|---|---|---|---|---|---|---|---|---|---|---|---|---|
| 25 | H | 3,4-(CH3)2-phenyl | H | CH3[a] | O | 3 | H | C | 65 | 120-121 | EtOH | $C_{25}H_{28}N_2O$ |
| 26 | H | 3,4-(CH3O)2-phenyl | H | H | O | 3 | H | B | 34 | 138-139.5 | EtOH | $C_{24}H_{26}N_2O_3$ |
| 27 | H | 3,4-(CH3O)2-phenyl | H | CH3[a] | O | 3 | H | C | 81 | 145-147 | EtOAc-Hex | $C_{25}H_{28}N_2O_3$ |
| 28 | H | 3,4-(CH3O)2-phenyl | H | CH3[b] | O | 3 | H | C | 62 | 156-159 | EtOAc | $C_{25}H_{28}N_2O_3$ |
| 29 | H | 3-CH3O-phenyl | H | H | S | 3 | H | E | 66 | Oil | | $C_{23}H_{24}N_2OS$ |
| 30 | H | 3-CH3O-phenyl | H | CH3[a] | S | 3 | H | E | 74 | Oil | | $C_{24}H_{26}N_2OS$ |

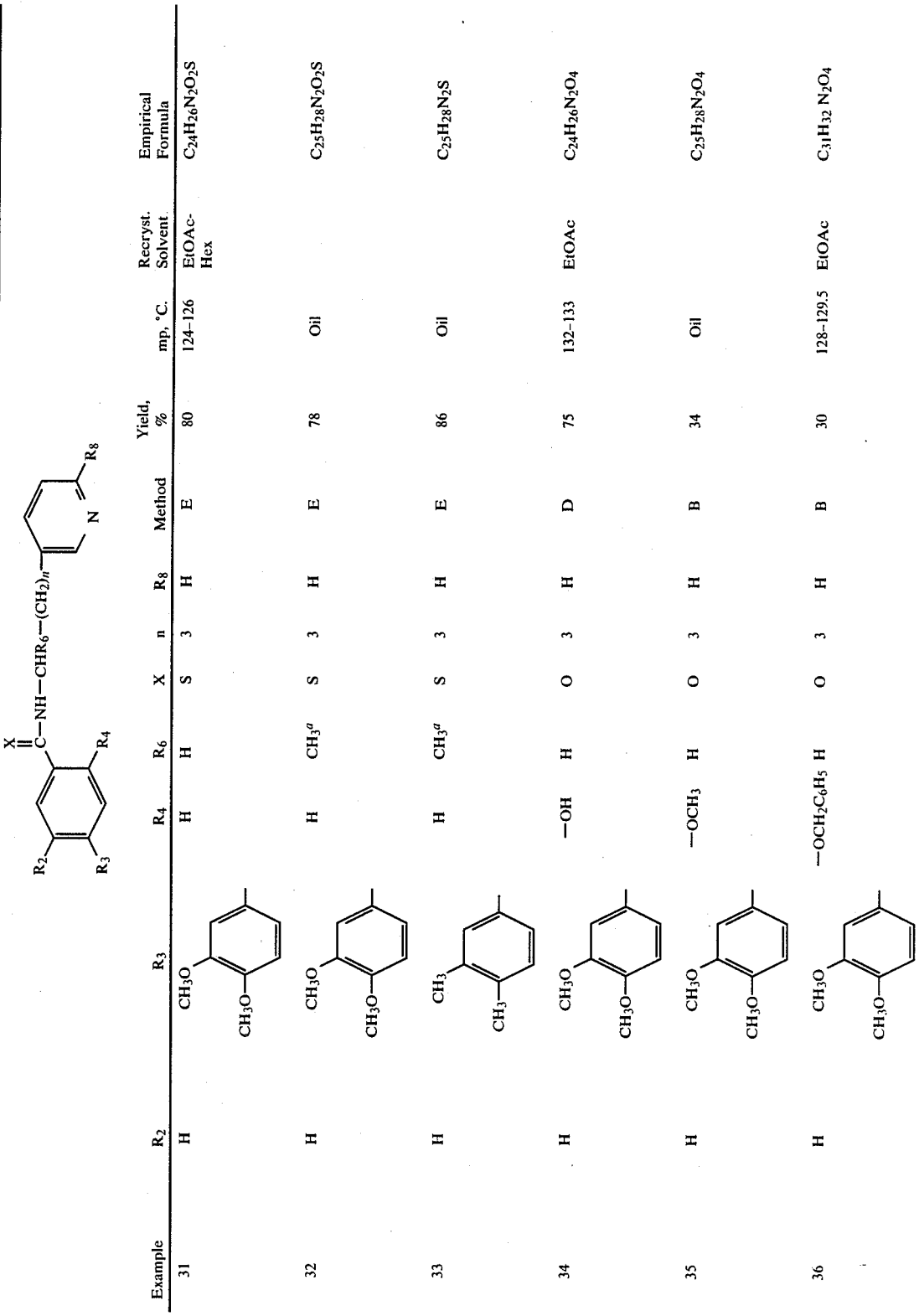
| Example | R2 | R3 | R4 | R6 | X | n | R8 | Method | Yield, % | mp, °C. | Recryst. Solvent | Empirical Formula |
|---|---|---|---|---|---|---|---|---|---|---|---|---|
| 31 | H | CH3O / CH3O | H | H | S | 3 | H | E | 80 | 124–126 | EtOAc-Hex | $C_{24}H_{26}N_2O_2S$ |
| 32 | H | CH3O / CH3O | H | CH3[a] | S | 3 | H | E | 78 | Oil | | $C_{25}H_{28}N_2O_2S$ |
| 33 | H | CH3 / CH3 | H | CH3[a] | S | 3 | H | E | 86 | Oil | | $C_{25}H_{28}N_2S$ |
| 34 | H | CH3O / CH3O | —OH | H | O | 3 | H | D | 75 | 132–133 | EtOAc | $C_{24}H_{26}N_2O_4$ |
| 35 | H | CH3O / CH3O | —OCH3 | H | O | 3 | H | B | 34 | Oil | | $C_{25}H_{28}N_2O_4$ |
| 36 | H | CH3O / CH3O | —OCH2C6H5 | H | O | 3 | H | B | 30 | 128–129.5 | EtOAc | $C_{31}H_{32}N_2O_4$ |

-continued

| Example | R$_2$ | R$_3$ | R$_4$ | R$_6$ | X | n | R$_8$ | Method | Yield, % | mp, °C. | Recryst. Solvent | Empirical Formula |
|---|---|---|---|---|---|---|---|---|---|---|---|---|
| 37 | H | CH$_3$O—, CH$_3$O— (3,4-dimethoxyphenyl) | H | CH$_3$[a] | O | 3 | CH$_3$ | C | 48 | 130–135 | EtOAc | C$_{26}$H$_{30}$N$_2$O$_3$ |
| 38 | H | CH$_3$O—, CH$_3$O— | H | CH$_3$[a] | O | 3 | C$_2$H$_5$ | C | 56 | 143–146 | EtOAc | C$_{27}$H$_{32}$N$_2$O$_3$ |
| 39 | nC$_4$H$_9$— | nC$_4$H$_9$— | H | H | O | 3 | H | C | 79 | Oil | | C$_{24}$H$_{34}$N$_2$O |
| 40 | nC$_4$H$_9$— | nC$_4$H$_9$— | H | H | O | 3 | H | C | 57 | 59–62 | EtOAc-Hex | C$_{26}$H$_{30}$N$_2$O |
| 41 | nC$_3$H$_7$— | (phenyl) | H | H | O | 3 | H | C | 83 | Oil | | C$_{25}$H$_{28}$N$_2$O |
| 42 | nC$_3$H$_7$— | (phenyl) | H | CH$_3$[b] | O | 3 | H | C | 88 | Oil | | C$_{26}$H$_{30}$N$_2$O |
| 43 | nC$_4$H$_9$— | CH$_3$O—, CH$_3$O— | H | H | O | 3 | H | C | 87 | Oil | | C$_{28}$H$_{34}$N$_2$O$_3$·0.4H$_2$O |

-continued

| Example | R2 | R3 | R4 | R6 | X | n | R8 | Method | Yield, % | mp, °C. | Recryst. Solvent | Empirical Formula |
|---|---|---|---|---|---|---|---|---|---|---|---|---|
| 44 | nC4H9— | 3-CH3O, 4-CH3O-phenyl | H | CH3[b] | O | 3 | H | C | 89 | 84–86 | Hex | $C_{29}H_{36}N_2O_3$ |
| 45 | H | 4-CH3-phenyl | H | H | O | 3 | H | C | 29 | 94–95 | CH2Cl2—Et2O—Hex | $C_{28}H_{26}N_2O$ |
| 46 | phenyl | 4-CH3-phenyl | H | H | O | 3 | H | C | 93 | foam | | $C_{28}H_{26}N_2O \cdot 0.25 HO_2$ |
| 47 | phenyl | 4-CH3-phenyl | H | CH3[a] | O | 3 | H | C | 77 | 75–78 | Et2O-Hex | $C_{29}H_{28}N_2O$ |
| 48 | 3-CH3O-phenyl | 3-CH3O-phenyl | H | H | O | 3 | H | C | 96 | Oil | | $C_{30}H_{30}N_2O_3$ |
| 49 | 4-CH3O-phenyl | 4-CH3O-phenyl | H | H | O | 3 | H | C | 91 | Oil | | $C_{30}H_{30}N_2O_3$ |

-continued

| Example | R$_2$ | R$_3$ | R$_4$ | R$_6$ | X | n | R$_8$ | Method | Yield, % | mp, °C. | Recryst. Solvent | Empirical Formula |
|---|---|---|---|---|---|---|---|---|---|---|---|---|
| 50 | 3-F-C$_6$H$_4$ | 3-F-C$_6$H$_4$ | H | H | O | 3 | H | C | 99 | Oil | — | C$_{28}$H$_{24}$F$_2$N$_2$O |
| 51 | Br | 3,4-(CH$_3$O)$_2$-C$_6$H$_3$ | H | H | O | 3 | H | C | 86 | 98–100 | EtOAc-Hex | C$_{24}$H$_{25}$BrN$_2$O$_3$ |
| 52 | Br | 3,4-(CH$_3$O)$_2$-C$_6$H$_3$ | H | CH$_3$[b] | O | 3 | H | C | 74 | 125–127 | EtOAc-Hex | C$_{25}$H$_{27}$BrN$_2$O$_3$ |
| 53 | O$_2$N | 3,4-(CH$_3$O)$_2$-C$_6$H$_3$ | H | H | O | 3 | H | C | 83 | 134–136 | EtOAc | C$_{24}$H$_{25}$N$_3$O$_5$ |
| 54 | O$_2$N— | 3,4-(CH$_3$O)$_2$-C$_6$H$_3$ | H | CH$_3$[b] | O | 3 | H | C | 87 | 144–145 | EtOAc | C$_{25}$H$_{27}$N$_3$O$_5$ |
| 55 | CH$_3$O— | 3,4-(CH$_3$O)$_2$-C$_6$H$_3$ | H | H | O | 3 | H | C | 87 | 119–121 | EtOAc | C$_{25}$H$_{28}$N$_2$O$_4$ |

-continued

| Example | R2 | R3 | R4 | R6 | X | n | R8 | Method | Yield, % | mp, °C. | Recryst. Solvent | Empirical Formula |
|---|---|---|---|---|---|---|---|---|---|---|---|---|
| 56 | phenyl | H | H | H | O | 3 | H | C | 66 | Oil | | $C_{22}H_{22}N_2O \cdot 0.15 H_2O$ |
| 57 | H | cyclohexyl | H | H | O | 3 | H | C | 71 | 105-158 | EtOAc | $C_{22}H_{28}N_2O$ |
| 58 | $nC_4H_9$ | phenyl | H | H | O | 2 | H | C | 75 | Oil | | $C_{25}H_{28}N_2O \cdot 0.25 H_2O$ | footnote:
a—racemic
b—R enantiomer

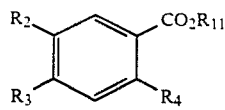

| Example | $R_2$ | $R_3$ | $R_4$ | $R_{11}$ | Yield, % | mp, bp °C./mm | Method | Solvent | Empirical Formula |
|---|---|---|---|---|---|---|---|---|---|
| 59 | $nC_4H_9$ | $nC_4H_9$ | H | H | 36 | 60–62 | J | Hexane | $C_{15}H_{24}O_2$ |
| 60 | $nC_3H_7$ | phenyl | H | H | 90 | 75–80 | J | Hexane | $C_{16}H_{16}O_2$ |
| 61 | $nC_4H_9$ | phenyl | H | H | 52 | 75–79 | J | Hexane | $C_{17}H_{18}O_2$ |
| 62 | $nC_4H_9$ | 3,4-(CH$_3$O)$_2$-phenyl | H | H | 65 | 122–127 (dec) | J | Cyclohexane | $C_{19}H_{22}O_4$ |
| 63 | 3-CH$_3$O-phenyl | 3-CH$_3$O-phenyl | H | H | 89 | 120–123 | J | EtOAc-hexane | $C_{21}H_{18}O_4$ |
| 64 | 4-CH$_3$O-phenyl | 4-CH$_3$O-phenyl | H | H | 65 | 191–193 | J | EtOAc-hexane | $C_{21}H_{18}O_4$ |
| 65 | 3-F-phenyl | 3-F-phenyl | H | H | 79 | 184–186 | J | EtOAc-hexane | $C_{19}H_{12}F_2O_2$ |
| 66 | HC≡C— | 3,4-(CH$_3$O)$_2$-phenyl | H | H | 62 | 228–229 | J | EtOH-Hexane | $C_{17}H_{14}O_4$ |
| 67 | CH$_2$=CHCH$_2$— | 3,4-(CH$_3$O)$_2$-phenyl | H | H | 82 | 160–161 | J | EtOAc-MeOH | $C_{18}H_{18}O_4$ |
| 68 | Br | 3,4-(CH$_3$O)$_2$-phenyl | H | H | 79 | 199–201 | J | CH$_2$Cl$_2$-Hexane | $C_{15}H_{13}BrO_4$ |
| 69 | NO$_2$ | 3,4-(CH$_3$O)$_2$-phenyl | H | H | 65 | 260–263 | J | HOAc-EtOAc | $C_{15}H_{13}NO_6$ |
| 70 | CH$_3$O | 3,4-(CH$_3$O)$_2$-phenyl | H | H | 90 | 193–194 | J | CH$_3$OH—H$_2$O-EtOAc | $C_{16}H_{16}O_5$ |
| 71 | $nC_4H_9$ | $nC_4H_9$ | H | CH$_3$ | 28 | 110–115/0.1 | M | — | $C_{16}H_{24}O_2$ |
| 72 | $nC_3H_7$ | phenyl | H | CH$_3$ | 57 | 112–113/0.1 | M | — | $C_{17}H_{18}O_2$ |
| 73 | $nC_4H_9$ | phenyl | H | CH$_3$ | 17 | 142–145/0.1 | M | — | $C_{18}H_{20}O_2$ |
| 74 | $nC_4H_9$ | 3,4-(CH$_3$O)$_2$-phenyl | H | CH$_3$ | 63 | Oil | M | — | $C_{20}H_{24}O_4$ |

-continued

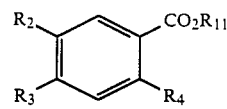

| Example | R$_2$ | R$_3$ | R$_4$ | R$_{11}$ | Yield, % | mp, bp °C./mm | Method | Solvent | Empirical Formula |
|---|---|---|---|---|---|---|---|---|---|
| 75 | 3-CH$_3$O-C$_6$H$_4$- | 3-CH$_3$O-C$_6$H$_4$- | H | CH$_3$ | 37 | 103–107 | M | MeOH—H$_2$O | C$_{22}$H$_{20}$O$_4$ |
| 76 | 4-CH$_3$O-C$_6$H$_4$- | 4-CH$_3$O-C$_6$H$_4$- | H | CH$_3$ | 33 | Oil | M | — | C$_{22}$H$_{20}$O$_4$ |
| 77 | 3-F-C$_6$H$_4$- | 3-F-C$_6$H$_4$- | H | CH$_3$ | 31 | Oil | M | — | C$_{20}$H$_{14}$F$_2$O$_2$ |
| 78 | Br | 3,4-(CH$_3$O)$_2$-C$_6$H$_3$- | H | CH$_3$ | 33 | 101.5–102.5 | I | EtOAc-Hexane | C$_{16}$H$_{15}$BrO$_4$ |
| 79 | NO$_2$ | 3,4-(CH$_3$O)$_2$-C$_6$H$_3$- | H | CH$_3$ | 70 | 127–129 | I | EtOAc-Hexane | C$_{16}$H$_{15}$NO$_6$ |
| 80 | CH$_3$O | 3,4-(CH$_3$O)$_2$-C$_6$H$_3$- | H | CH$_3$ | 47 | 88–89 | I | EtOAc-Hexane | C$_{17}$H$_{18}$O$_5$ |
| 81 | H | 3,4-(CH$_3$)$_2$-C$_6$H$_3$- | H | H | 50 | 208–209 | J | EtOAc | C$_{15}$H$_{14}$O$_2$ |
| 82 | H | 3,4-(CH$_3$O)$_2$-C$_6$H$_3$- | H | CH$_3$ | 58 | 130–131 | I | EtOH | C$_{16}$H$_{16}$O$_4$ |
| 83 | H | 3,4-(CH$_3$O)$_2$-C$_6$H$_3$- | H | H | 55 | 221–222 | J | EtOAc | C$_{15}$H$_{14}$O$_4$ |
| 84 | H | 3-C$_6$H$_5$CH$_2$O-C$_6$H$_4$- | H | CH$_3$ | 42 | 105–106 | I | EtOAc | C$_{21}$H$_{18}$O$_3$ |
| 85 | H | 3-C$_6$H$_5$CH$_2$O-C$_6$H$_4$- | H | H | 52 | 185–186 | J | EtOH | C$_{20}$H$_{16}$O$_3$ |
| 86 | H | 3,4-(CH$_3$O)$_2$-C$_6$H$_3$- | OCH$_3$ | CH$_3$ | 42 | 96–97.5 | I | EtOAc-Hex | C$_{15}$H$_{14}$O$_5$ |
| 87 | H | 3,4-(CH$_3$O)$_2$-C$_6$H$_3$- | OCH$_3$ | H | 52 | 134–135 | J | EtOAc | C$_{16}$H$_{16}$O$_5$ |
| 88 | H | 3,4-(CH$_3$O)$_2$-C$_6$H$_3$- | OCH$_2$C$_6$H$_5$ | H | 40 | 161–162 | I,J | EtOAc-Hex | C$_{22}$H$_{20}$O$_5$ |

-continued

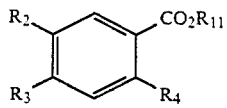

| Example | R2 | R3 | R4 | R11 | Yield, % | mp, bp °C./mm | Method | Solvent | Empirical Formula |
|---|---|---|---|---|---|---|---|---|---|
| 89 | 3-CH3-C6H4- | H | H | CH3 | 45 | 135–138/0.1 | I | — | C15H14O2 |
| 90 | 3-CH3O-C6H4- | H | H | CH3 | 34 | 115–120/0.1 | I | — | C15H14O3 |

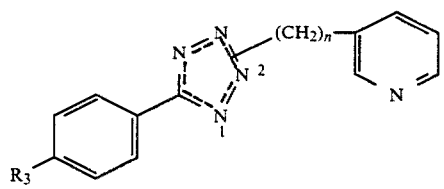

| Example | R3 | Pos. | n | Method | Yield % | mp° C. | Cryst. Solvent | Empirical Formula |
|---|---|---|---|---|---|---|---|---|
| 91 | 3,4-(CH3)2-C6H3- | 1 | 3 | G | 13 | 98–100 | EtOAc-Hex | C23H23N5 |
| 92 | 3,4-(CH3)2-C6H3- | 1 | 4 | G | 40 | 103–105 | EtOH | C24H25N5 |
| 93 | 3,4-(CH3)2-C6H3- | 2 | 3 | H | 70 | 81–82 | EtOAc-Hex | C23H23N5 |
| 94 | 3,4-(CH3)2-C6H3- | 2 | 4 | H | 53 | 112.5–114 | EtOH | C24H25N5 |

EXAMPLE 95

(R)-2-Ethynyl-3',4'-dimethoxy-N-[1-methyl-4-(3-pyridinyl) butyl]-[1,1'-biphenyl]-4-carboxamide A solution of 459 mg of 3',4'-dimethoxy-2-ethynyl[1,1'-biphenyl]-4-carboxylic acid in 8 mL of dimethylformamide was cooled in an ice bath and treated with 0.25 mL of triethylamine and 0.38 mL of diphenylphosphoryl azide. After 1 hour. 0.3 mL of (R)alpha-methyl-3-pyridinebutanamine was added and the reaction mixture was allowed to warm to room temperature over 48 hours. The reaction mixture was diluted with ethyl acetate, washed with water and brine, dried and concentrated. The residue was chromatographed over 50 g of silica gel eluting with ethyl acetate and the product was crystallized from ethyl acetate-hexane to give 576 mg of (R)-2-Ethynyl-3',4'-dimethoxy-N-[1-methyl-4-(3-pyridinyl)butyl][1.1'-biphenyl]-4-carboxamide, mp 135°–137° C.

EXAMPLE 96

(R)-2-Ethyl-3',4'-dimethoxy-N-[1-methyl-4-(3-pyridinyl)butyl]1.1'-biphenyl1-4-carboxamide A suspension of 435 mg of 2-ethynyl-3',4'-dietmhoxy-N-[1-methyl-4-(3-pyridinyl)butyl][1,1'-biphenyl]-4-carboxamide was hydrogenated over 45 mg of 10% palladium on carbon and the product was chromatographed over 50 g of silica gel eluting with ethyl acetate to give 381 mg of (R)-2-Ethyl-3',4'-dimethoxy-N-[1-methyl-4-(3-pyridinyl)butyl)-[1,1'-biphenyl]-4-carboxamide as a colorless oil.

EXAMPLE 97

(R,S)-alpha-Methyl)-4-(3-pyridinyl)-3-butyn-1-ol

In an inert atmosphere, 26 g of bis(triphenylphosphine) palladium dichloride and 2.28 g of cuprous iodide were added to a stirred solution of 311.2 g of (R,S)-4-pentyn-2-ol. 556.8 g of 3-bromopyridine and 665 mL of triethylamine in 1.8L of dichloromethane at ambient temperature. After stirring for 75 minutes the mildly exothermic reaction reached reflux temperature, and when the gentle boiling had subsided (40 minutes). exteral heat was applied to maintain reflux for 5 additional hours. The cooled reaction was stirred overnight at room temperature, then 1L of water and 500 g of ice were added, followed by 420 mL of conc. hydrochloric acid (HCl) and the stirring was continued for several minutes. After the phases were separated, the aqueous layer was extracted with dichloromethane (4×1L) and then the organic layers were backwashed with 1L of 1N HCl before being discarded. The original aqueous phase was treated with 500 mL of 10N sodium hydroxide (NaOH) and the second aqueous layer was basified with 200 mL of 10N NaOH before each was extracted in turn with dichloromethane (1×3×1L). The combined organic extracts were dried over Potassium carbonate ($K_2CO_3$) and evaporated to constant weight under reduced pressure to yield 477.3 g of crude (R,S)-alpha-methyl-4-(3-pyridinyl)-3-butyn-1-ol as an amber oil.

EXAMPLE 98

Preparation of (R,S)-alpha-methyl-4-pyridinebutanol

The crude (R,S)-alpha-methyl-4-(3-pyridinyl)-3-butyn-1-ol (477.3 g) obtained in the previous Example was hydrogenated over 20 g of platinum oxide in 3.5L of ethanol at room temperature and atmospheric pressure. After the uptake of hydrogen had stopped. The catalyst was filtered and the solvent was removed under reduced pressure. The residual oil was distilled on a Kugelrohr apparatus (115°-120° C./ 0.1 mm) to yield 420.5 g of (R,S) alpha methyl-3 pyridinebutanol.

EXAMPLE 99

Preparation of 5-(3-pyridinyl)-2-pentanone

A stirred solution of 218.6g of oxalyl chloride in 1.5L of dry dichloromethane was cooled to −75° C. under argon, then a mixture of 141g of dry dimethylsulfoxide in 200 mL of dichloromethane was added dropwise over 75 minutes such that the reaction temperature did not exceed −72° C. The mixture was stirred at −75° C. for 10 minutes. Then a solution of 271.5 g of (R,S)-alpha-methyl-3-pyridinebutanol in 125 mL of dichloromethane was added dropwise over 55 minutes, while the reaction temperature was maintained below −70° C. After the addition of substrate was completed, the mixture was stirred at −75° C. for another 30 minutes, then 520 mL of triethylamine was added over 65 minutes while the reaction temperature was maintained between −65° and −70° C. The cooling bath was removed, and after the reaction was allowed to equilibrate to room temperature over 1 hour, 1L of water was added and the phases separated. The aqueous layer was extracted with dichloromethane (2×800 mL), and then the organic phase and extracts were washed in turn with 800 mL of 1.5N NaOH and with 800 mL of 10% sodium chloride (NaCl). The combined organic layers were dried ($K_2CO_3$) and evaporated to yield 266 g of crude ketone. The product was distilled to yield 248.6 g of 5-(3pyridinyl)-2-pentanone (bp 100°-102° C./0.2 mm).

EXAMPLE 100 Preparation of (R,S)-methanesulfonic acid 5-(3-pyridinyl)-2-pentyl ester In an inert atmosphere a solution of 2.42 mL of methanesulfonyl chloride in 10 mL of dichloromethane was added over 10 minutes to a stirred mixture of 5.0 g of (R,S)-alpha-methyl-3-pyridinebutanol and 6.2 mL of triethylamine in 50 mL of dry dichloromethane maintained at −40° C. After 30 minutes the reaction was warmed to 0° C. then a small piece of ice was added and the mixture was stirred in a an ice bath for another 15 minutes. The solution was then washed in turn with water (3×15 mL), 1N NaOH (2×15 mL) and brine (10 mL). The dried ($K_2CO_3$) organic layer was evaporated to furnish 7.2 g of (R,S)-methanesulfonic acid 5-(3-pyridinyl)-2-pentyl ester.

EXAMPLE 101

Preparation of (R,S)-3-(4-azidopentyl)pyridine

A mixture of 2.5g of (R,S)-methanesulfonic acid 5-(3-pyridinyl)-2-pentyl ester, 0.832 g of sodium azide, 1.5 mL of water and 15 mL of dimethylformamide was stirred at 50° C. under argon for 150 minutes. The cooled solution was diluted with 40 mL of water and extracted with dichloromethane (3×30 mL). The extracts were washed in turn with water (2×20 mL) and then were combined, dried ($K_2CO_3$) and evaporated to furnish 1.76 g of (R,S)-3-(4-azidopentyl)pyridine as an oil.

EXAMPLE 102

Preparation of (R,S)-3-(ethoxycarbonyl)butyltriphenylphosphonium bromide.

A solution of 86.3 g of (R,S -4-bromo-2-methylbutanoic acid ethyl ester and 104.9 g of triphenylphosphine in 600 mL of toluene was stirred at reflux for 4 days. As the reaction proceeded, the phosphonium bromide separated from solution as an oil. After the reaction was cooled, the toluene supernatant was decanted and replaced with 500 mL of fresh toluene. The mixture was stirred at reflux for 30 minutes, then was cooled and the toluene layer was again decanted. After this process was repeated a second time. the residual oil was dried in vacuo to give 187 g of (R,S)-3-(ethoxycarbonyl)butyltriphenylphosphonium bromide as a viscous oil.

EXAMPLE 103

Preparation of [(R,S)-Z[-2-methyl-5-(3-pyridinyl)4-pentenoic acid ethyl ester

A stirred solution of 10.56g of sodium hydride (60% dispersion in oil) in 1000 mL of dry dimethylsulfoxide was heated at 70° C. until the evolution of hydrogen stopped (30 minutes). then the solution was cooled to 0° C. and a solution of 103.7g of (R,S)-3-(ethoxycarbonyl)-butyltriphenylphosphonium bromide in 200 mL dimethylsulfoxide was added. After the mixture had stirred at room temperature for 30 minutes, a solution of 20.8 mL of 3-pyridinecarboxaldehyde in 100 mL of tetrahydrofuran was added and the reaction was stirred at room temperature overnight. The mixture was diluted with ice-water and extracted with dichloromethane (6×150 mL). The combined organic layers were then extracted with 4×400 mL of 0.5N HCl. The acidic layers were made basic with 125 mL triethylamine and extracted with dichloromethane (5×150 mL), and the dried (K$_2$CO$_3$) extracts were evaporated to furnish 34 g of crude reaction product. An initial purification of the material by high pressure liquid chromatography (HPLC) (ether-hexane; 3:2) yielded 11.9 g of a mixture of (Z)- and (E)-isomers (4:1). A subsequent separation of the mixture by HPLC with recycle gave 6.77 g of [(R,S)-Z]-2-methyl-5- (3-pyridinyl)-4-pentenoic acid ethyl ester and 3 g of a mixture of [(R,S)-Z]-2-methyl-5-(3-pyridinyl)-4-Pentenoic acid ethyl ester and its (E)-isomer.

EXAMPLE 104

Preparation of (R,S)-alpha-methyl-3-pyridinepentanoic acid ethyl ester

A solution of 5.5 g of a mixture (1:1) of [(R,S)-E]- and [(R,S)-Z]-2-methyl-5-(3-pyridinyl)-4-pentenoic acid ethyl ester in 100 mL was ethanol was hydrogenated over 0.4 g of 10% palladium on carbon (Pd/C). After the uptake of hydrogen had stopped, the catalyst was removed by filtration and the solvent evaporated to give 5.33 g of (R,S)-alpha-methyl-3-pyridinepentanoic acid ethyl ester.

EXAMPLE 105

Preparation of (R,S)-alpha-methyl-3-pyridinepentanoic acid

A mixture of 5.3 g of (R,S)-alpha-methyl-3-pyridinepentanoic acid, 35 mL of 1N NaOH and 35 mL of methanol was stirred at reflux for 3 hours, then most of the methanol was removed under reduced pressure. The solution was diluted to 100 mL with water and extracted with dichloromethane (3×35 mL). The aqueous layer was then neutralized with 35 ml of 1N HCl and extracted with dichloromethane 3×30 mL). then dried over sodium sulfate (Na Extracts were evaporated to yield 3.47 g of (R,S)-alpha-methyl-3-pyridinepentanoic acid.

EXAMPLE 106

Preparation of (R,S)-[1-methyl-4-(3-pyridinyl)buty]carbamic acid 1,1-dimethylethyl ester.

As in Example 132, 1.93 g of (R,S)-alpha-methyl3-pyridinepentanoic acid when treated with 2.21 mL of diPhenylphosphorylazide in 10 mL of t-butanol containing 1.4 mL of triethylamine furnished 2.45 g of crude product. Purification of the material by HPLC (ethyl acetate) yielded 2.2 g of (R,S)-[1-methyl-4-(3-pyridinyl)butyl]carbamic acid 1,1dimethylethyl ester as a colorless oil.

EXAMPLE 10

Preparation of (R,S)-N-[1-methyl-4-(3-pyridinyl)butyl]acetamide

To a mixture of 10.6 g of (R,S)-alpha-methyl-3-pyridinebutanol in 30 mL of acetonitrile was added 20 mL of sulfuric acid. After the reaction was stirred at 50° C. for 2 hours, it was poured over a mixture of 500 g of ice and 400 mL of 4N NaOH and extracted with dichloromethane (2×150 mL). Evaporation of the dried (K$_2$CO$_3$) extracts gave 6 g of crude product which was purified by HPLC (methanol-ethyl acetate; 1:49) and triturated with ether to yield 2.9 g of (R,S)-N-[1-methyl-4-(3-pyridinyl)butyl]acetamide, mp 70°-71.5° C.

EXAMPLE 108

Preparation of (R,S)-alpha-methyl-3-pyridinebutanamine

From 5-(3-pyridinyl)-2-pentanone

A mixture of 248.5g of 5-(3-pyridinyl)-2-pentanone, 95.85 g of sodium cyanoborohydride and 1170 g of ammonium acetate in 5.3L of dry methanol was stirred at room temperature for 8 days, then 3 L of methanol was removed by distillation under reduced pressure (internal temp 30° C.). The reaction was cooled in an ice bath as 3.8 L of 6N HCL was added dropwise over 2 hours. After the mixture was stirred at room temperature overnight, it was made strongly basic by the addition of 2 L of 12.5N NaOH and extracted with dichloromethane (1×2 L; 2×1L). The combined extracts were dried (K$_2$CO$_3$) and evaporated to yield 244 g of a light brown oil which was distilled to give 205 g of (R,S)-alpha-methyl-3-pyridinebutanamine (bp 95°-100° C./0.15 mm)

EXAMPLE 109

Preparation of (R,S) -alpha-methyl-3-pyridinebutanamine (a) From 3-(4-azidopentyl)pyridine A solution of 0.9 g of (R,S)-3-(4-azidopentyl)pyridine in 25 mL ethanol was hydrogenated over 0.05g 10% Pd/C at 50 psi. After 105 minutes, the catalyst was removed by filtration and o the solvent was removed under reduced pressure to yield 0.69 g of a colorless oil. Evaporative distillation of the crude product furnished 0.57 g of (R,S)-alpha-methyl-3-pyridinebutanamine.

(b) From (R,S)-1-methyl-4-(3-pyridinyl)butyl]carbamic acid 1.1-dimethylethyl ester As in Example 133, hydrolysis of 2.1 g of (R,S)-[1-methyl-4-(3-pyridinyl)butyl]carbamic acid 1,1-dimethylethyl ester in 25 mL of 1N HCl yielded, after the usual work up and evaporative distillation of the product (95°-100° C./0.2mm). 1.25 g of (R,S)-alpha-methyl-3-pyridinebutanamine.

(c) From (R,S)-N-[1-methyl-4-(3-pyridinyl)butyl]acetamide

A solution of 2.06 g of (R,S)-N-[1-methyl-4-(3-pyridinyl) butyl]acetamide in 50 mL of 6N HCl was stirred at reflux for 22 hours. In an argon atmosphere the cooled mixture was made basic with the careful addition of 30 mL of 10N NaOH and was extracted with dichloromethane (2×75 mL). The extracts were washed with brine, then were combined, dried (K$_2$CO$_3$) and evaporated to give 1.43 g of (R,S)-alpha-methyl-3-pyridinebutanamine.

EXAMPLE 110

Preparation of [R-(R*,R*)]-alpha-hydroxy-N-[1-methyl-4-(3-pyridinyl)butyl]benzeneacetamide a) From (R,S)-alpha-methyl-3-pyridinebutanamine A solution of 281.5 g of 1.3-dicyclohexylcarbodiimide in 400 ml of dimethylformamide was added to a stirred solution of 204 g of (R,S)-alpha-methyl-3-pyridinebutanamine. 198.4 g of (R)-mandelic acid and 209.75 g of 1-hydroxybenzotriazole in 1400 mL of dimethylformamide, maintained at −10° C. during the addition by intermittent cooling with a dry ice-acetone bath. After stirring at −5° for 4 hours then at room temperature overnight the mixture was recooled to 0° C. for 2 hours. The precipitated solids were filtered and washed in turn with cold dimethylformamide (2×150 mL) and ethyl acetate (2×300 mL). This material, a mixture of 1,3-dicyclohexylurea (DCU) and the less soluble (R*,R)-mandelamide, was dispersed in 2 L of 1N HCl and stirred at room temperature for 3 hours. The undissolved solids (DCU) were removed by filtration and were washed with 200 mL of dilute HCl and with water. The filtrate was basified and the resulting material was collected by filtration, washed with water and dried in vacuo to give 64.4 g of [R-(R*,R*)]alpha-hydroxy-N-[1-methyl-4-(3-pyridinyl-)butyl]benzeneacetamide. the (R*,R)-mandelamide. mp 144°–146° C.; $[\alpha]_D^{25}$ −27.8° (c, 1.0, MeOH)

The original mother liquors and washings were concentrated to dryness under reduced pressure and the residue was dispersed in 2L of 1.5N NaOH and extracted with dichloromethane (1×2 2×1L). The organic extracts were washed with in turn with 1N NaOH (2×800 mL) and then in turn with 1N HCl (1×1.5L; 2×750 mL). The combined acidic aqueous layers were basified with 350 mL of 10N NaOH and extracted with dichloromethane (1×2 L; 2×1 L). The extracts were dried ($K_2CO_3$) and evaporated to give 280 g of mandelamide, rich (~3:2) in the (S*,R)-diastereomer. The residue was crystallized three times from 2-propanol to yield 74.1 g of the less soluble (R*,R)-mandelamide, mp 144°–146° C.

The mother liquors from the final two crystallizations were combined evaporated and the residue crystallized twice from 2-propanol to give an additional 7.2 g of the (R*,R)-diastereomer, mp 143°–145° C. The total yield of [R-(R*,R*)]-alpha-hydroxy-N-[1-methyl-4-(3-pyridinyl)butyl]benzeneacetamide obtained in three crops, was 145.6 g (78.5%).

All remaining mother liquors were combined, evaporated and dried to give 198 g of mandelamide rich in the (S*.R)-diastereoisomer. This material was reserved for further processing, particularly to serve as a potential source of (S)-alpha-methyl-4-pyridinebutanamine.

(b) Via an enatioselective process from 5-(3-pyridinyl)-2-pentanone

A solution of 70.5 g of 5-(3-pyridinyl)-2-pentanone and 53.5 g of (R)-(.)-alpha-methylbenzylamine in 700 mL of toluene containing 1.8 g of p-toluenesulfonic acid was heated at reflux for 17 hours. Water was removed from the reaction as it was formed using a Dean-Stark trap. The cooled solution was hydrogenated over 70 g of Raney Nickel at room temperature and 50 psi. When approximately 50% of the theoretical amount of hydrogen had been taken up, the reaction essentially stopped. The spent catalyst was removed and replaced with 70 g of fresh Raney Nickel and the hydrogenation was continued until the absorption of hydrogen ceased. After the catalyst was removed by filtration, the filtrate was washed with 250 mL of 1N sodium hydroxide solution, then was dried and evaporated to give 106 g of an oil. HPLC analysis of the product showed that the main component (~68%) was [R-(R*,R)]-N-[1-methyl-(3-pyridinyl) butyl]-alpha-methylbenzylamine along with 13% of the related S*.R)-diastereomer.

The above mixture (105g) in 1 L of ethanol was hydrogenolysed over 21 g of 20% Pd(OH)$_2$ on charcoal (50° C.; 25 psi) for a total of 51 hours. After the catalyst was removed by filtration. The solvent was evaporated and the residue distilled to provide 33.6 g of alpha-methyl-3-pyridinebutanamine enriched in the (R)-enantiomer.

To a cooled (−5° C.) solution of 32 g of the above enriched amine. 33 g of 1-hydroxybenzotriazole and 31.22 g of (R)-mandelic acid in 350 mL of dimethylformamide, was added a solution of 44.26 g of 1.3-dicyclohexylcarbodiimide in 150 mL of dimethylformamide and the mixture was stirred at −5° C. for 18 hours. After the precipitated dicyclohexylurea was removed by filtration, the filtrate was evaporated and the residue dispersed in 300 mL of cold 2N sodium hydroxide. The resulting solids were removed by filtration. Washed with dilute sodium hydroxide solution and with water and then dissolved in 500 mL of 2N hydrochloric acid. The acidic solution was extracted with dichloromethane (3×150 mL) to remove neutral impurities, then was basified with 10N sodium hydroxide and extracted with dichloromethane (6×300 mL). The dried extracts were evaporated to give 55 g of residual solid. Crystallization of the product from ethanol gave 25.6 g of [R-(R*,R)]-alpha- hydroxy-N-[1-methyl-4-(3-pyridinyl)butyl]benzeneacetamide, mp 141°–143° C. An additional 1.3 g of product, mp 141°–143° C., was obtained from the mother liquors.

EXAMPLE 111

Preparation of [S-(S*,S*)]-alpha-hydroxy-N-[1-methyl-4-(3-pyridinyl)-butyl]benzeneacetamide (a) From (R,S)-alpha-methyl-3-pyridinebutanamine To an ice cold solution of 2.0 g of (S)-(+)-mandelic acid and 1.82 mL of triethylamine in 20 mL of dry dimethylformamide was added 2.82 mL of diphenylphosphoryl azide. The mixture was stirred at 0° C. for 30 minutes before 2.15 g of (R,S)-alphamethyl-3-pyridinebutanamine was added. After the reaction was stirred at room temperature overnight, it was diluted with 130 mL of ethyl acetate. Washed with water (4×50 mL, dried ($K_2CO_3$) and evaporated. The residue was crystallized from ethyl acetate (3×) to give 0.45 g of [S-(S*,S)]-alpha-hydroxy-N-[1-methyl-4-(3-pyridinyl)butyl]benzeneacetamide, mp 142°–145° C.

The absolute configuration of [S-(S*,S*)]-alpha-hydroxy-N-[1-methyl-4-(3-pyridinyl)butyl]benzeneacetamide, was established by X-ray crystallographic analysis.

(b) From enriched (S)-alpha-methyl-pyridinebutanamine

A solution of 160 g of crude [S-(R*,R*)]-alpha-hydroxy-N-[1-methyl-4-(3-pyridinyl)butyl]benzeneacetamide in 800 mL of 6N HCl was treated with 85 mL conc. HCl and then was heated at reflux overnight as described in Example 16. The crude amine (~85 g), isolated in the normal manner was distilled to furnish 76.4 g of (S)-alpha-methyl-3-pyridinebutanamine, (60% ee; bp 89°–91°/0.15 mm).

Under the conditions outlined in Example 100a, 76.2 g of the amine was reacted with 74.2 g of (S)-mandelic acid in the presence of 105.2 g of 1,3-dicyclohexylcarbodiimide and 78.4 g of 1-hydroxybenzotriazole in 1 L of dimethylformamide. A similar work up furnished 109 g of [S-(S*,S*)]-alpha-hydroxy-N-[1-methyl-4--(3-pyridinyl)butyl]benzeneacetamide, mp 143°–145° C. $[\alpha]_D^{25}$ +27.8° (c, 1.0, MeOH).

EXAMPLE 112

Preparation of (R)-alpha-methyl-3-pyridinebutanamine

A solution of 145 g of [R-(R*,R*)]-alpha-hydroxy-N-[1-methyl-4-(3-pyridinyl)butyl]benzeneacetamide in 900 mL of 6N HCl was treated with 80 mL of conc. HCl and then was heated at reflux for 2 days. After most of the solvent was removed under reduced pressure, the residue was made decidedly basic with 10N NaOH in an argon atmosphere and extracted with dichloromethane (1×1.2L; 2×600 mL). The dried (K₂CO₃) extracts were evaporated and the crude product was distilled to give 78.5 g of (R)-alpha-methyl-3-pyridinebutanamine, (bP 95° C./0.2 mm).

EXAMPLE 113

Preparation of (S)-alpha-methyl-3-pyridinebutanamine

As in Example 112, a solution of 16.3 g of [S-(S*,S*)]alpha-hydroxy-N- 1-methyl-4-(3-pyridinyl)butyl]benzeneacetamide in 160 mL of 6N HCl was heated at reflux for 22 hours. The crude product, obtained by the usual work up was distilled to yield 8.3 g of (S)-alpha-methyl-3-pyridinebutanamine. (bp 85°–87° C./0.1 mm).

EXAMPLE 114

Preparation of (R,S)-alpha-ethyl-4-(3-pyridinyl)-3-butyn-1-ol

Under the conditions described in Example 97,395 g of 3-bromopyridine and 259.3 g of (R,S)-5-hexyne-3-ol were reacted together in 1.5 L of dichloromethane in the presence of 418 mL of triethylamine, 17.56 g of bis(triphenylphosphine)palladium dichloride and 1.7 g of cuprous iodide. The usual work-up furnished 361.5 g of crude (R,S)-alpha-ethyl-4-(3-pyridinyl)3-butyn-1-ol as a brown oil.

EXAMPLE 115

Preparation of (R,S)-alpha-ethyl-3-pyridinebutanol

As in Example 98, hydrogenation of 361.5 g of crude (R,S)-alpha-ethyl-4-(3-pyridinyl)-3-butyn-1-ol over 15 g of platinum oxide in 3L of ethanol at room temperature and atmospheric pressure and distillation of the product furnished 357 g of (R.S)-alpha-ethyl-3-pyridinebutanol (bP 120°–130°/0.1 mm) as a colorless oil.

EXAMPLE 116

Preparation of 6-(3-pyridinyl)-3-hexanone

As in Example 99. 356.6 g of (R,S)-alpha-ethyl-3-pyridinebutanol was added to a mixture prepared in the prescribed manner from 211.7 g of oxalyl chloride and 170 g of dimethylsulfoxide in 1.75L of dichloromethane. After the addition of 630 mL of triethylamine, the reaction was worked up in the usual way to yield 347.6 g of crude product which was distilled to give 327.9 g of 5-(3-pyridinyl)-3-hexanone (bp 110°–115° C./0.1 mm).

EXAMPLE 117

Preparation of (R,S)-alpha-ethyl-3-pyridinebutanamine

In the manner described in Example 108, 372.9 g of 6-(3-Pyridinyl)-3-hexanone was reacted with 116.5 g of sodium cyanoborohydride and 1426 g of ammonium acetate in 6.5L of dry methanol for 3 days at room temperature, and then 4.5L of 6N HCl was added and the mixture stirred overnight. Distillation of the crude product gave 289.4 g of (R,S)-alpha-ethyl3-pyridinebutanamine (bP 95°–100° C./0.1 mm).

EXAMPLE 118

Preparation of [R-(R*,R*)1-alpha-hydroxy-N-[1-ethyl-4-(3-pyridinyl)butyl]benzeneacetamide and [S-(R*.R=)]alpha hydroxy-N-[1-ethyl-4-(3-pyridinyl)butyl]benzeneacetamide.

As in Example 110a, a solution of 367.4 g of 1,3-dicyclohexylcarbodiimide in 500 mL of dimethylformamide was added to a stirred solution of 289 g of (R,S)-alpha-ethyl-3-pyridinebutanamine. 259 g of (R)-mandelic acid and 274 g of 1-hydroxybenzotriazole in 1.7 L of dimethylformamide maintained at −10° C. during the addition. After stirring at −5° C. for 3 hours, then at room temperature overnight, the mixture was recooled to 0° C. for 2 hours. The precipitated solids were filtered and washed in turn with cold dimethylformamide (3×150 mL) and ethyl acetate (3×200 mL). The solids, a mixture of 1,3-dicyclohexylurea (DCU) and the less soluble (R*,R)-mandelamide, was dispersed in 1N HCl (2 L) and stirred at room temperature for 4 hours. The undissolved solids (DCU) were removed by filtration and were washed with 200 mL dilute HCl and with water. The filtrate was basified and the resulting crystalline material was collected by filtration, washed with water and dried in vacuo to give 195.4 g of [R-(R*,R*)]-alpha-hydroxy-N-[-1-ethyl-4-(3-Pyridinyl)butyl]benzeneacetamide. mP 161.5°–163°; $[\alpha]_D^{25}$ −14.9° (c. 1.0 MeOH).

The original mother liquors and washings were concentrated to dryness and were worked up as in Example 110a. The crude residue was triturated with hot hexane (1 L), and the solids filtered to give 265 g of mandelamide rich (>7:1) in the more soluble (S*,R)-diastereomer. Fractional crystallization of the residue from 2-propanol furnished 147 g of [S-(R*,R*)]-alphahydroxy-N-[1-ethyl-4-(3-pyridinyl)butyl]benzeneacetamide, mP 122°–124° C; $[\alpha]_D^{25}$ −41.2° (c. 1.0 MeOH).

EXAMPLE 119

Preparation of (R)-alpha-ethyl-3-pyridinebutanamine

As in Example 112, a solution of 195 g of [R-(R..R.)]-alpha-hydroxy-N-[1-ethyl-4-(3-pyridinyl)butyl]benzeneacetamide in 1.1L of 6N HCl was treated with 104 mL of conc. HCl and then was heated at reflux for 2 days. The crude amine, obtained by the normal work up, was distilled to give 109 g of (R)-alphaethyl-3-pyridinebutanamine, (bP 105° C./0.2mm); $[\alpha]_D^{25}$ −11.9° (c. 1.0, MeOH)

EXAMPLE 120

Preparation of (S)-alpha-ethyl-pyridinebutanamine

As in Example 112, a solution of 31.2 g of [S-(R*,R*)]alpha-hydroxy-N-[1-ethyl-4-(3-pyridinyl)butyl]benzeneacetamide in 175 ml of 6N HCl was treated with 16 mL of conc. HCl and then was heated at reflux for 42 hours. The normal work up furnished 16.4 g of (S)-alpha-ethyl-3-pyridinebutanamine, (bp 95°–98° C./0.1 mm); $[\alpha]_D^{25}$ +11.75 (c, 1.0, MeOH).

EXAMPLE 121

Preparation of trifluoromethanesulfonic acid 6-methyl3-pyridinyl ester

A suspension of 7.48 g of 5-hydroxy-2-methylpyridine and 24.4 g of bis(trifluoromethanesulphonyl)-phenylimide in 25 mL of dichloromethane was cooled in an ice bath as 10 mL of dry triethylamine was added. After 1 hour at 0° C. the mixture was allowed to stir at room temperature for 18 hours, then was washed in turn with 1N NaOH (2×50 mL) and with half saturated $K_2CO_3$ solution. Concentration of the dried ($K_2CO_3$) solution gave a yellow oil which was evaporatively distilled to yield 14.48 g of trifluoromethanesulfonic acid 6-methyl-3-pyridinyl ester, bp 65°–70° C./0.1 mm.)

EXAMPLE 122

Preparation of (R,S)-5-(6-methyl-3-pyridinyl-4-pentyn-2-ol

A solution of 28 g trifluoromethanesulfonic acid 6-methyl3-pyridinyl ester and 14.4 g of (R,S)-4-pentyn-2-ol and 110 mL triethylamine in 350 mL of dry dimethylformamide was deoxygenated with argon and 2.4 g of bis(triphenylphosphine)palladium dichloride was added. After the mixture was stirred at 90° C. for 3 hours, it was cooled, then acidified with 300 mL of 6N HCl and extracted with ether. The aqueous phase was made basic with sodium hydroxide solution and extracted with ethyl acetate. The organic extract was washed with brine, then dried ($K_2CO_3$) and evaporated to furnish an oil which was evaporatively distilled to yield 10.8 g of (R,S)-5-(6-methyl-3-pyridinyl)-4-pentyn-2-ol, bP 123°–130° C./0.02 mm.

EXAMPLE 123

Preparation of (R,S)-alpha-6-dimethyl-3-pyridinebutanol

As in Example 98,10.3 g of (R,S)-5-(6-methyl-3-pyridinyl)-4-pentyn-2-ol was hydrogenated over 1.1 g of 10% Pd/C in 135 mL of ethanol at room temperature and atmospheric pressure. After the usual work up, the resulting yellow oil was purified by HPLC (ethyl acetate) to give 10.45 g of (R,S)-alpha-6-dimethyl-3-pyridinebutanol. A portion was evaporatively distilled at 105°–110° C./0.1 mm to furnish the analytical sample.

EXAMPLE 124

Preparation of 5-(6-methyl-3-pyridinyl)-2-pentanon

Under conditions similar to that describe in Example 99, 10.25 g of (R,S)-alpha-6-dimethyl-3-pyridinebutanol in 50 mL of dichloromethane was added to an mixture prepared from 8.58 g of oxalyl chloride and 9.27 g of dimethylsulfoxide in 225 mL of dichloromethane. After the addition of 36.8 mL of triethylamine, the reaction was worked up in the usual manner and the crude product was purified by HPLC (ethyl acetate-hexane; 1:1). The resulting material was distilled to give 7.4 g of 5-(6-methyl-3-pyridinyl)-2-pentanone (bP 88°–92° C./0.05 mm).

EXAMPLE 125

Preparation of (R.S)-6-alpha-dimethyl-3-pyridinebutanamine

As in Example 108. 7.27 g of 5-(6-methyl-3-pyridinyl)-2-pentanone was reacted with 2.71 g of sodium cyanoborohydride and 31.1 g of ammonium acetate in 115 mL of dry methanol for 3 days at room temperature. After the chilled reaction was quenched by the addition of 110 mL of 6N HCl, the mixture heated at reflux for 90 minutes then was cooled and worked up in the usual manner. Distillation of the crude product gave 4.31 g of (R.S)-6-alpha-dimethyl-3-pyridinebutanamine (bp 98°–101° C./0.1 mm).

EXAMPLE 126

Preparation of 5-bromo-2-[(2-trimethylsilyl)ethynvl]pyridine

A degassed solution of 15.0 g of 2,5-dibromopyridine, 9.0 mL of trimethylsilylacetylene and 0.27 g of cuprous iodide in 200 mL of triethylamine was treated with 1.0 g of bis(triphenylphosphine)palladium dichloride. After an ice bath was used to control the initial exotherm, the reaction was stirred at room temperature overnight, then was diluted with 400 mL ether. The mixture was washed in turn with water (4×75 mL) and with brine (75 mL), then was dried ($K_2CO_3$) and evaporated. The residual dark oil was passed through a plug of silica gel (ether) and then was purified by HPLC (ether-hexane; 1:49). Crystallization of the resulting material from hexane gave 11.86 g of 5-bromo-2-[(2-trimethylsilyl)ethynyl]pyridine, mp 56°–59° C.

EXAMPLE 127

Preparation of (R,S)-5-[6-2-trimethylsilyl)ethynyl]3-pyridinyl]-pentyne-2-ol

A solution of 9.78 g of 5-bromo-2-[(2-trimethylsilyl) ethynyl]Pyridine and 0.19 g of cuprous iodide in 150 mL of triethylamine and 50 mL dichloromethane were deoxygenated with argon and 3.4 g of (R,S)-4-pentyn-2-ol and 0.7 g of bis(triphenylphosphine)palladium dichloride were added. After the dark mixture was stirred overnight at room temperature, the solvents were removed under reduced pressure and the residue was dissolved in ether. The solution was washed with water and brine, then was dried ($K_2CO_3$) and evaporated. The crude product was filtered through a plug of silica gel (ethyl acetate-hexane; 1:10) and then was purified by HPLC (ethyl acetate) to give (R,S)-5-[6-[2-trimethylsilyl)ethynyl]-3-pyridinyl]-4-pentyne-2-ol, mp 79°–80° C.

EXAMPLE 128

Preparation of (R,S 6-ethyl-3-pyridine-alpha-methylbutanol

A solution of 8.51 g of (R,S)-5-[6-[2-(trimethylsilyl) ethynyl]-3-pyridinyl]-4-pentyn-2-ol in 60 mL of methanol and 15 mL of 2.5N NaOH was stirred for 1 hour and diluted to 300 mL with ethyl acetate. The separated organic layer was washed in turn with water and brine, then was dried ($K_2CO_3$) and evaporated. The residue was hydrogenated over 0.7 g of 10% Pd/C in 150 mL of ethanol at atmospheric pressure and room temperature. After the normal work up the crude hydrogenation product was evaporatively distilled to afford 5.61 g of (R,S)-6-ethyl-3-pyridine-alpha-methylbutanol (bp 110°–115° C./0.1 mm).

EXAMPLE 129

Preparation of 5-(6-ethyl-3-pyridinyl)-2-pentanone.

5-(6-Ethyl-3-pyridinyl)-2-pentanone was prepared by the method described in Example 99. Starting with 4.4 g of (R,S)-6-ethyl-3-pyridine-alpha-methylbutanol, there was obtained 4.9 g of 5-(6-ethyl-3-pyridinyl)-2-pentanone (bp 107°-110° C./0.1 mm).

EXAMPLE 130

Preparation of (R,S)-6-ethyl-alpha-methyl-3-pyridinebutanamine.

(R,S)-6-ethyl-alpha-methyl-3-pyridinebutanamine was made by the method outlined in Example 108. Starting from 4.75 g of -(6-ethyl-3-pyridinyl)-2-pentanone there was obtained 2.44 g of (R,S)-6-ethyl-alpha-methyl-3-pyridinebutanamine, bp 101°-104° C./0.15 mm.

EXAMPLE 131

Preparation of (R,S)-alpha-cyclopropyl-3-pyridinepentanoic acid

In an inert atmosphere. 33 mL of 1.6M butyl lithium in hexane was added to a stirred solution of 7.4 mL diisopropylamine in 20 mL dry tetrahydrofuran previously cooled to −78° C. for 30 minutes. then a solution of 2.5 g cyclopropaneacetic acid in 10 mL dry tetrahydrofuran was added over 3 minutes. The reaction was allowed to equilibrate to ambient temperature and then was heated at 50° C. for 1 hour to complete the formation of the dianion. The mixture was recooled to −78° C. and a solution of 7.67 g 3-(3-bromopropyl) pyridine (freshly liberated from its HBr salt) in 20 mL tetrahydrofuran was added. The reaction was allowed to warm to room temperature and then was heated at 50° C. for 7 hours. The solvents were removed in vacuo and the residue was dissolved in 100 mL 1N HCl and extracted with dichloromethane (3×50 ml). The organic layers were backwashed in turn with 2×25 mL portions of 1N HCl, then the aqueous layers were basified with 17 mL 10N NaOH solution and extracted with dichloromethane (3×100 mL) to remove the starting bromide. The aqueous phase was then acidified by the addition of 3 mL acetic acid and extracted with dichloromethane (1×150 mL; 2×100 mL). The extracts were washed with brine, then were combined, dried (Na2SO4) and evaporated to give 4.6 g of (R,S)-alpha-cyclopropyl-3-pyridinepentanoic acid as a colorless solid. A portion was crystallized from ether-hexane to yield the analytical sample, mp 82°-84° C.

EXAMPLE 132

Preparation of (R,S)-[1-cyclopropyl-4-(3-pyridinyl)butyl]carbamic acid 1,1-dimethylethyl ester A solution of 4.2 g of (R,S)-alpha-cycloPropyl-3-pyridinepentanoic acid 5.8 g of diphenylphosphorylazide and 3 mL of triethylamine in 40 mL of t-butanol was stirred at reflux under argon overnight. After the solvents were removed under reduce pressure, the residue was dissolved in 100 mL of dichloromethane and washed with 2×50 mL portions of 1N NaOH. The aqueous layers were washed in turn with 50 mL of dichloromethane. Then the combined organic extracts were dried (K2CO3) and evaporated to yield 5.6 g of an oil. The crude carbamate was purified by HPLC (ethyl acetate) to furnish 4.8 g of (R,S)-[1-cycopropyl-4-(3-pyridinyl)butyl]carbamic acid 1,1-dimethylethyl ester as a colorless oil.

EXAMPLE 133

Preparation of (R,S)-alpha-cyclopropyl-3-pyridinebutanamine

A solution of 4.4 g of (R.S)-[1-cyclopropyl-4-(3-pyridinyl) butyl]-carbamic acid 1,1-dimethylethyl ester in 50 mL of 1N HCl was heated on a steam bath for 75 minutes then was cooled and extracted with 50 mL of ether. In an atmosphere of argon, the aqueous layer was treated with 6 mL of 10N NaOH and extracted with 2×50 mL portions of dichloromethane. Evaporation of the dried (K2CO3) extracts gave 2.8 g of (R,S)-alphacyclopropyl-3-pyridinebutanamine as a colorless oil.

EXAMPLE 134

Preparation of (R,S)-alpha-propyl-3-pvridinepentanoic acid

As in Example 131,2.04 g of pentanoic acid was treated with two equivalents of lithium diisopropylamide (LDA) and then reacted with 4.0 g of 3-(3-bromopropyl)pyridine. After workup, the crude product (3.5 g) was crystallized from ether-hexane to afford 2.7 g of (R,S)-alpha-propyl-3-pyridinepentanoic acid, mp 55°-57° C.

EXAMPLE 135

Preparation of (R,S)-1-propyl-4-(3-pyridinyl)butyllcarbamic acid 1,1-dimethylethyl ester As in Example 132, 2.5 g of (R,S)-alpha-propyl-3-pyridinepentanoic acid when reacted with 2.45 mL of diphenylphosphorylazide in 25 mL of t-butanol containing 1.6 mL of triethylamine furnished 3.1 g of crude carbamate. Purification of the material by HPLC (ethyl acetate) yielded 2.75 g (R,S)-[1-propyl-4-(3-pyridinyl)-butyl]carbamic acid 1,1-dimethylethyl ester as an oil.

EXAMPLE 136

Preparation of (R,S)-alpha-propyl-3-pyridinebutanamine As in Example 133, hydrolysis of 1.8 g of (R,S)-[1-propyl-4-(3-pyridinyl)butyl]carbamic acid 1,1-dimethylethyl ester in 5 mL of 1N HCl. after the usual work up, gave 1.15 g of (R,S)-alpha-propyl-3-pyridinebutanamine. A portion was distilled on a Kugelrohr apparatus (110° C./0.1 mm) to yield the analytical sample.

EXAMPLE 137

Preparation of (R,S)-alpha-(1-methylethyl)-3-pyridinepentanoic acid

As in Example 131, 2.04 g of isovaleric acid was treated with two equivalents of LDA and then reacted with 4.0 g of 3-(3-bromopropyl)pyridine. The crude product was crystallized from ether-hexane to yield 2.8 g of (R,S)-alpha-(1-methylethyl)3-pyridinepentanoic acid. mp 52-55° C. Recrystallization of a sample from the same solvents gave the analytical specimen, mp 54°-56° C.

EXAMPLE 138

Preparation of (R,S)-[1-(1-methylethyl)-4-(3-Dyridinyl) buty]carbamic acid 1,1-dimethylethyl ester.

As in Example 132,2.3 g of (R,S)-alpha-(1-methylethyl)3-pyridine-pentanoic acid. when reacted with 2.3 mL of diphenylphosphorylazide in 25 mL of t-butanol containing 1.5 mL of triethylamine gave 2.8 g of product. Purification of the crude ester by HPLC (ethyl acetate) gave 2.5 g of (R.S)-[1-(1-methylethyl)-4-(3-pyridinyl)butyl]carbamic acid 1,1-dimethylethyl ester as an oil.

EXAMPLE 139

Preparation of (R,S)-alpha-(1-methylethyl)-3-pyridinebutanamine

As in Example 133, hydrolysis of 1.7 g of (R,S)-[1-(1-methylethyl)-4-(3-pyridinyl)butyl]carbamic acid 1,1-dimethylethyl ester in 25 mL of 1N HCl yielded 1.1 g of (R,S)-alpha-(1-methylethyl)-3-pyridinebutanamine. A small sample was distilled on a Kugelrohr (110°–115° C./0.1 mm) to furnish the analytical specimen.

EXAMPLE 140

Preparation of (R.S)-alpha-butyl-3-pyridinepentanoic acid

As in Example 131, 2.32 g of hexanoic acid was treated with two equivalents of LDA and then reacted with 4.0 g of 3-(3-bromopropyl)pyridine. The usual work up yielded 4 g of (R,S)-alpha-butyl-3-pyridinepentanoic acid, as an oil.

EXAMPLE 141

Preparation of (R,S)-1-1-butyl-4-(3-pyridinyl)butyl]carbamic acid 1,1-dimethylethyl ester As in Example 132, 3.7 g of (R,S)-alpha-butyl-3pyridinepentanoic acid, when reacted with 3.4 mL of diphenylphosphorylazide in 25 mL of t-butanol containing 2.2 mL of triethylamine yielded 4.4 g of crude carbamate. Purification of the product by HPLC (ethyl acetate) gave 3.6 g of (R,S)-1-butyl-4-(3-pyridinyl)-butyl]carbamic acid 1,1-dimethylethyl ester as an oil.

EXAMPLE 142

Preparation of (R,S)-alpha-butyl-3-pyridinebutanamine

As in Example 133, hydrolysis of 2.2 g of (R,S)-[1-butyl-4-(3-pyridinyl)butyl carbamic acid 1,1-dimethylethyl ester in 25 mL 1N HCl, after the usual work-up. yielded 1.35 g of (R,S)-alpha-butyl-3-pyridinebutanamine. A portion was distilled on a Kugelrohr (115° C/0.1 mm) to yield the analytical sample.

EXAMPLE 143

Preparation of (R,S)-alpha-cyclopentyl-3-pyridineoentanoic acid

As in Example 131, 2.56 g of cyclopentaneacetic acid was treated with two equivalents of LDA and then reacted with 4.0 g of 3-(3-bromopropyl)pyridine. The crude product (4 g) was crystallized from ether-hexane to yield 3.1 g of (R,S)-alpha-cyclopentyl-3-pyridinepentanoic acid, mp 95°–97° C.

EXAMPLE 144

Preparation of (R,S)-1-cyclopentyl-4-(3-pyridinyl)butyl]carbamic acid 1,1-dimethylethyl ester As in Example 132, 2.8 g of (R,S)-alpha-cyclopentyl-3-pyridinepentanoic acid, when treated with 2.5 mL of diphenylphosphorylazide in 25 mL of t-butanol containing 1.58 mL of triethylamine yielded 3.4 g of product. Purification of the crude by HPLC (ethyl acetate) yielded 2.5 g of (R,S)-[1-cyclopentyl-4-(3-pyridinyl)-butyl]carbamic acid 1,1-dimethylethyl ester as an oil.

EXAMPLE 145

Preparation of (R,S)-alpha-(1-cyclopentyl)-3-pyridinebutanamine

As in Example 133, hydrolysis of 1.6 g of (R,S)-[1-cyclopentyl)-4-(3-pyridinyl)butyl]carbamic acid 1,1-dimethylethyl ester in 25 mL of 1N HCl yielded 1.05 g of (R,S)-alpha-(1-cyclopentyl)-3-pyridinebutanamine. A sample was distilled (125°–130° C./0.1 mm) to yield the analytical specimen.

EXAMPLE 146

Preparation of (R,S)-alpha-cyclohexyl-3-pyridinepentanoic acid

As in Example 131, 2.84 g of cyclohexaneacetic acid was treated with two equivalents of LDA and then reacted with 4.0 g of 3- 3-bromopropyl)pyridine. The crude product (3.8 g) was crystallized from ether-hexane to give 2.7 g of (R,S)-alphacyclohexyl-3-pyridinepentanoic acid, mp 92°–93° C.

EXAMPLE 147

Preparation of (R,S)-1-cyclohexyl-4-(3-pyridinyl)buty]carbamic acid 1,1-dimethYlethyl ester As in Example 132, 2.5 g of (R,S)-alpha-cyclohexyl-3pyridinepentanoic acid, when reacted With 2.68 g of diphenylphosphorylazide in 25 mL of t-butanol containing 0.97 g of triethylamine yielded 3.1 g of crude product. Purification by HPLC (ethyl acetate) furnished 2.8 g of (R,S)-[1-cyclohexyl-4-(3-pyridinyl)butyl]carbamic acid 1,1-dimethylethyl ester. The material was crystallized from ether-hexane to yield the analytical sample, mp 64°–66° C.

EXAMPLE 148

Preparation of (R,S)-alpha-(1-cyclohexyl)-3-pyridinebutanamine

As in Example 133, hydrolysis of 1.9 g of (R,S)-1-[1-cyclohexyl-4-(3-pyridinyl)butyl]carbamic acid 1,1-dimethylethyl ester in 25 mL of 1N HCl yielded 1.25 g of (R,S)-alpha-(1-cyclohexyl)-3-pyridinebutanamine. Distillation of a portion of the material on a Kugelrohr apparatus (140°–145° C./0.1 mm) yielded the analytical sample.

EXAMPLE 149

Preparation of alpha-[3-(3-pyridinyl)propyl]-3-pyridinepentanoic acid

As in Example 131. 7.16 g of 3-pyridinepentanoic acid was treated with two equivalents of LDA and then reacted with 8.8 g of 3-(3-bromopropyl)pyridine. The usual work-up yielded 8.9 g of an orange colored oil, consisting mainly of alpha-[3-(3-pyridinyl)propyl]-3-pyridinepentanoic acid contaminated by a small amount of starting 3-pyridinepentanoic acid.

EXAMPLE 150

Preparation of [1-[3-(3-pyridinyl)propyl]-4-(3-pyridinyl) butyl]carbamic acid 1,1-dimethylethyl ester As in Example 132, 8.8 g of alpha-[3-(3-pyridinyl)-propyl]-3-pyridinepentanoic acid, when reacted with 9.1 g of diphenylphosphorylazide in 75 mL of t-butanol containing 4.1 mL of triethylamine furnished 11.1 g of product. Purification of the crude by HPLC (ethyl acetate-methanol; 13:1) yielded 5.5 g of [1-[3-(3-pyridinyl)propyl]-4-(3-pyridinyl)butyl]carbamic acid 1,1-dimethylethyl ester as an oil.

EXAMPLE 151

Preparation of alpha-[3 (3-pyridinyl)propyl]-3-pyridinebutanamine.

As in Example 133 hydrolysis of 5.4 g of [1-[3-(3-pyridinyl)-propyl]-4-(3-pyridinyl)butyl]carbamic acid 1,1-dimethylethyl ester in 55 mL of 1N HCl yielded 3.15 g of alpha-[3-(3-pyridinyl)propyl]-3-pyridinebutanamine.

EXAMPLE 152

Preparation of (R,S)-alpha-(4-bromophenyl)-3-pyridinepentanoic acid

As in Example 131, 2.15 g of p-bromophenylacetic acid was treated with two equivalents of LDA and then reacted with 2.0 g of 3-(3-bromopropyl)pyridine. The crude product was crystallized from ether-hexane to yield 1.46 g of (R,S)-alpha(4-bromophenyl)-3-pyridinepentanoic acid, mp 123°–126° C.

EXAMPLE 153

Preparation of (R,S)-[1-(4-bromophenyl)-4-(3-pyridinyl)butyl]carbamic acid 1,1-dimethylethyl ester As in Example 132, 1.45 g of (R,S)-alpha-(4-bromophenyl)-3-pyridinepentanoic acid, when treated with 0.94 mL of diphenylphosphorylazide in 10 mL of t-butanol containing 0.44 g of triethylamine yielded 1.7 g of crude (R,S)-[1-(4-bromophenyl)-4-(3-pyridinyl)-butyl]carbamic acid 1,1-dimethylethyl ester as an oil.

EXAMPLE 154

Preparation of (R,S)-alpha-(4-bromophenyl)-3-pyridinebutanamine

As in Example 133, hydrolysis of 1.7 g of (R,S)-[1-(4-bromophenyl)-4-(3-pyridinyl)butyl]carbamic acid 1,1-dimethylethyl ester in 15 mL of 1N HCl yielded 1.1 g of (R,S)-alpha-(4-bromophenyl)-3-pyridinebutanamine.

EXAMPLE 155

Preparation of (R,S)-Z -2-methyl-5-(3-pyridinyl)-4-pentenoic acid

A solution of 9.95 g of [(R,S)-Z]-2-methyl-5-(3-pyridinyl)-4-pentenoic acid ethyl ester in 75 mL of 1N NaOH and 75 mL of methanol were stirred at reflux for 3 hours, then most of the methanol was removed under reduced pressure. After the solution was extracted with dichloromethane (3×50 mL), the aqueous layer was neutralized with 75 ml of 1N HCl and extracted with dichloromethane (4×40 mL). The dried (Na₂SO₄) extracts were evaporated to give 7.28 g of a solid which was crystallized from ether-hexane to yield 6.12 g of [(R,S)-Z]-2-methyl-5-(3-pyridinyl)-4-pentenoic acid, mP 79°–82° C.

EXAMPLE 156

[(R,S)-Z]-[1-methyl-4-(3-pyridinyl)-S-butenyl]carbamic acid 1,1-dimethylethyl ester As in Example 132, 2.87 g of [(R,S)-Z]-2-methyl-5-(3-pyridinyl)-4-pentenoic acid was reacted with 3.31 mL of diphenylphosphoryl azide in 30 mL of t-butanol containing 2.1 mL of triethylamine. The product was isolated in the usual manner to yield 3.88 g of [(R,S)-Z]-1-[1-methyl-4-(3-pyridinyl)-3-butenyl]carbamic acid 1,1-dimethylethyl ester as an oil.

EXAMPLE 157

(R,S)-Z]-1-methyl-4-(3-pyridinyl)-3-butenamine

As in Example 133, hydrolysis of 3.88 g of (R,S)-Z]-[1-methyl-4-(3-Pyridinyl)-3-butenyl]carbamic acid 1,1-dimethylethyl ester in 50 mL of 1N HCl yielded, after the usual work-up and evaporative distillation of the product (100–120° C./0.1 mm), 1.7 g of [(R,S)-Z]-1-methyl-4-(3-pyridinyl)-3-butenamine as an oil.

EXAMPLE 158

Preparation of 3-(4-methyl-4-pentenyl)pyridine

A suspension of 7.0 g of sodium hydride (60% dispersion in oil) in 75 mL of dry dimethylsulfoxide was stirred at 75° C. under argon for 45 minutes at which time the evolution of hydrogen had ceased. After the solution was cooled, 61 g of methyltriphenylphosphonium bromide was added and the mixture was stirred at room temperature for 30 minutes before the addition of 25 g of 5-(3-pyridinyl)-2-pentanone in 125 mL of dimethylsulfoxide. The reaction was then stirred at room temperature overnight. After the addition of 1 L of 1N hydrochloric acid solution, the precipitated triphenylphosphine oxide was removed by filtration, and the filtrate was basified with 110 mL of 10N sodium hydroxide. The product was extracted with dichloromethane (4×300 ml) and the extracts were washed with brine, then were combined. dried (K₂CO₃) and evaporated to give 25 g of crude product. The material was purified by HPLC (ethyl acetate:hexane: 1:1) to yield 17.5 g of 3-(4-methyl-4-pentenyl)pyridine as a colorless oil.

EXAMPLE 159

Preparation of N-[1,1-dimethyl-4-(3-pyridyl)butyl]-2-nitrobenzeneacetamide

A mixture of 22.7 g of 3-(4-methyl-pentenyl)pyridine and 22.8 g of 2-nitrobenzeneacetonitrile in 80 mL of acetic acid was cooled to 12°–13° C. and then 16 mL of sulfuric acid was added dropwise over 6 minutes. The reaction was stirred for 2 hours at ambient temperature, then after the acetic acid was removed in vacuo, 1 L of water was added and the mixture was extracted with dichloromethane to remove neutral impurities. The aqueous layer was basified with 10N sodium hydroxide, and extracted with dichloromethane (4×200 mL). The dried (K₂CO₃) extracts were evaporated to give 35.6 g of N-[1,1-dimethyl(3-pyridyl)butyl]-2-nitrobenzeneacetamide. A portion was crystallized from ethyl acetate-hexane to yield the analytical sample, mp 117°–118.5° C.

EXAMPLE 160

Preparation of alpha,alpha-dimethyl-3-pyridinebutanamine

A solution of 35.2 g of N-[1.1-dimethyl-4-(3-pyridyl) butyl]-2-nitrobenzeneacetamide in 250 mL of acetic acid was hydrogenated over 3.5 g of 10% Pd/C at atmospheric Pressure and ambient temperature. The reaction was exothermic and stopped abruptly after the uptake of the theoretical amount of hydrogen (7.5 L). The catalyst was removed by filtration and the filtrate was heated at reflux for 90 minutes. After the solution was cooled. 10 mL of conc. HCl was added and the solvent was removed under reduced pressure. The residue was taken up in IL of water and extracted with ethyl acetate (4×200 mL) to remove the by product, oxindole. The aqueous layer was basified with 10N NaOH and extracted with dichloromethane to give. after evaporation of the dried ($K_2CO_3$) extracts 15 g of product. The material was distilled on a Kugelrohr apparatus (95° C; 0.1 mm) to yield 14.3 g of alpha,alphadimethyl-3-pyridinebutanamine.

EXAMPLE 161

Preparation of 4-pyridinepropanamide

In an inert atmosphere 10.7 g of 4-pyridinecarboxaldehyde was added to a stirred solution of 35.1 g of (carbomethoxy)methylenetriphenylphosphorane in 250 mL of methanol. After 90 minutes. the solvent was removed under reduced Pressure and the residue was triturated with etherhexane. The resulting solid (triPhenylPhosPhine oxide) was removed by filtration. and the filtrate was evaporated to yield 18 g of a mixture of (E)- and (Z)-3-(4-pyridinyl)-2-propenoic acid methyl ester contaminated with a small amount of residual triphenylphosphine oxide.

The crude mixture (18 g) was hydrogenated over 1.6 g of 10% Pd/C in 200 mL of methanol at atmospheric pressure and room temperature. After the uptake of hydrogen had stopped, the catalyst was removed by filtration and the solvent was removed in vacuo to furnish 16 g of crude 4-pyridinepropanoic acid methyl ester.

The crude ester was dissolved in 250 mL of 7.1M methanolic ammonia solution and was stirred at room temperature for 65 hours. After the solvent and excess ammonia were removed by distillation under reduced pressure. The residue was dissolved in 150 mL of 1N HCl and extracted with dichloromethane to remove residual triphenylphosphine oxide. The aqueous phase was basified with 40 mL of 4N NaOH and then was extracted with ethyl acetate (5×300 mL). The dried ($Na_2SO_4$) extracts were evaporated to furnish 6 g of the amide. The aqueous layer was concentrated to dryness and triturated with tetrahydrofuran (4×100 mL) and evaporation of the tetrahydrofuran extracts yielded an additional 5 g of amide. The combined crude products were dried, triturated with ether and the solids were filtered to yield 10.7 g of 4-pyridinpPropanamide, mp 164°–166° C.

EXAMPLE 162

Preparation of 4-pyridinepropanamine

A 1M solution of $BH_3$ in tetrahydrofuran (192 mL) was added over 10 minutes to a stirred suspension of 7.2 g of 4-PyridineProPanamide in 50 mL of tetrahydrofuran at 05°–° C. After the cooling bath was removed, the reaction was stirred at reflux for 17 hours and then the solvent was removed in vacuo. The residue was dissolved in 160 mL of 3.5N HCl and after the solution was heated on a steam bath overnight it was cooled. basified with excess 10N NaOH and then extracted with dichloromethane. The dried ($K_2CO_3$) extract was evaporated to furnish 6.98 g of an amber oil, which was distilled in vacuo to give 4.3 g of 4-pyridinepropanamine (bp 100°–110° C./0.2mm).

EXAMPLE 163

Preparation of 5-(2-pyridinyl)-4-pentyn-1-ol

As in Example 97, 15.8 g of 2-bromoPyridine and 8.4 g of 4-pentyn-1-ol were reacted together in 125 mL of dichloromethane in the presence of 4.2 mL of triethylamine. 2.1 g of bis(triphenylphosphine)palladium dichloride and 0.135 g of cuprous iodide. After 48 hours at reflux, the reaction was worked up in the usual manner. Distillation of the crude product yielded 8.8 g of 5-(2-pyridinyl)-4-pentyn-1-ol (bp 115°–120° C./0.25 mm).

EXAMPLE 164

Preparation of 2-pyridinepentanol 5-(2-Pyridinyl)-4-pentyn-1-ol (8.8g) was hydrogenated over 1.0 g of 10% Pd/C in 125 mL of ethanol at room temperature and atmospheric pressure. After the uptake of hydrogen had stopped, the catalyst was removed by filtration and the solvent was removed under reduced pressure. The residual oil was distilled on a Kugelrohr apparatus (115°–120° C./0.1 mm) to yield 8.4 g of 2-pyridinepentanol.

EXAMPLE 165

Preparation of 2-(5-chloropentyl)pyridine

A solution of 4 1 mL of thionyl chloride in 30 mL of dichloromethane was added over 10 minutes to a stirred solution of 6.65 g of 2-pyridinepentanol in 60 mL of dichloromethane maintained at −5° C. After the addition was complete. the mixture was stirred at room temperature for 17 hours, then was rechilled to 5° C. as 150 ml of 1N NaOH was added droPwise over 10 mintues. The layers were separated and the aqueous layer was extracted with 75 mL of dichloromethane. The organic layers were washed with brine, then were combined. dried ($K_2CO_3$) and evaporated to yield 7.4 g of 2-(5-chloropentyl)pyridine as an oil.

EXAMPLE 166

Preparation of 1-[5-(2-pyridinyl)pentyl]-1H-isoindole-1.3-(2H)-dione

A mixture of 6.35 g of 2-(5-chloropentyl)pyridine, 7.7 g potassium phthalimide, 5.2 g of sodium iodide and 3.7 g of sodium carbonate in 50 mL of dimethylformamide was stirred at 50° C. for 20 hours. After the solvent was removed under reduced pressure, the residue was taken up in 100 mL of water and extracted with dichloromethane (1×250 mL). The organic extracts were washed with brine, then were combined, dried ($K_2CO_3$) and concentrated in vacuo to give 10.1 g of an organe colored oil. Purification of the crude material by HPLC (ethyl acetate-hexane) yielded 6.7 g of 1-[5-(2-pyridinyl) pentyl]-1H-isoindole-1,3-(2H)-dione.

EXAMPLE 167

Preparation of 2-pyridienpentanamine

A solution of 6.5 g of 1-[5-(2-pyridinyl)pentyl]-1H-isoindole-1,3-(2H)-dione and 1.15 mL of hydrazine hydrate in 35 mL of ethanol was heated at reflux for 90 minutes. The cooled reaction mixture was treated with 10 ml of 6N HCl, and the solids were removed by filtration and washed with 20 mL of 0.5N HCl. After the filtrate was concentrated to remove ethanol. it was basified with 10N NaOH and extracted with dichloromethane. The organic extract was washed with brine, then was dried (K₂CO₃) and evaporated to give 3.4 g of a yellow oil. The crude reaction product was evaporatively distilled (105°–110° C./0.01 mm) to yield 2.4 g of 2-pyridinepentanamine.

EXAMPLE 168

Preparation of 3-(8-isoquinolinyl)-2-propyn-1-ol

In an inert atmosphere. 0.068 g of bis(triphenylphosphine)palladium dichloride and 0.013 g of cuprous iodide was added with stirring to a deoxygenated solution of 1 g of 8-bromoisoquinoline, 0.56 mL of propargyl alcohol and 2 mL of triethylamine in 25 mL of dichloromethane. The mixture was stirred at room temperature for 2 hours and then at reflux for 20 hours. The cooled reaction was filtered and the filtrate was concentrated in vacuo. The residual oil was purified by HPLC (ethyl acetate-toluene; 2:3) to yield 0.4 g of -(8-isoquinolinyl)-2-propyne-1-ol, mp 138°–139° C.

EXAMPLE 169

Preparation of 8-isoquinolinepropanol

A solution of 0.4 g of 3-(8-isoquinolinyl)-2-propyn-1-ol in a mixture of 10 mL of ethanol and 5 mL of methanol was hydrogenated over 0.06 g 10% Pd/C at room temperature and atmospheric pressure for 22 hours and then at 50 psi for 20 hours. After the catalyst was removed by filtration and the filtrate was concentrated, the residual oil was purified by HPLC (methanol-chloroform; 1:19) and crystallized from ethyl acetate-hexane to yield 0.136 g of 8-isoquinolinepropanol, mp 66°–69° C.

EXAMPLE 170

Preparation of 3-(8-isoquinolinyl)propyl]-1H-isoindole1,3-(2H)-dione

A solution of 0.142 g of 8-isoquinolinepropanol in 3 mL of chloroform was added to a solution of 0.085 mL of thionyl chloride in 1 mL of chloroform and the reaction was stirred at reflux for 3 hours. The cooled mixture was washed with NaHCO₃ solution and with brine, then was dried (Na₂SO₄) and evaporated. The residual oil was stirred with 0.281 g of potassium phthalimide and 0.126 potassium iodide in 3 mL of dry dimethylformamide at 130° C. for 90 minutes. After evaporation of the solvent, the residue was partitioned between dichloromethane and water. The dried (Na₂SO₄) organic layer was concentrated and the crude product was purified by HPLC (ethyl acetate-toluene; 1:4 and then crystallized from ether to give 0.177 g of [3-(8-isoquinolinyl)Propyl]-1H-isoindole-1,3-(2H)-dione, mp 135°–140° C.

EXAMPLE 171

Preparation of 8-isoquinolinepropanamine

To a refluxing solution of 0.174 g of [3-(8-isoquinolinyl) propyl]-1H-isoindole-1,3-(2H)-dione in 8 mL of ethanol was added 0.12 mL of hydrazine hydrate and the reaction was stirred at reflux for 5.5 hours. The solvent was removed under reduced pressure and the residue was triturated with chloroform. The chloroform extract was concentrated to an oil which was passed through a short column of silica gel (chloroform-methanoltriethylamine; 1:4:15) to yield 0.103 g of 8-isoquinolinepropanamine as an oil.

EXAMPLE 172

Preparation of 4-(4-isoquinolinyl)-3-butyl-1-ol

In an inert atmosphere. 0.268 g of bis(triphenylphosphine) palladium dichloride and 0.072 g of cuprous iodide was added with stirring to a deoxygenated solution of 5 g of 4-bromoisoquinoline, 3.02 g of 3-butyn-1-ol and 10 mL of triethylamine in 20 mL of dichloromethane. The reaction was stirred at room temperature for 1 hour and then at reflux for 18 hours. The cooled mixture was filtered and the filtrate was washed with water. The dried (Na₂SO₄) organic phase was concentrated in vacuo and the residual oil was purified by HPLC (ethyl acetate-toluene; 2:3) to yield 3.4 g of 4-(4-isoquinolinyl)3-butyl-1-ol as an oil.

EXAMPLE 173

Preparation of (E)-4-(4-isoouinolinyl)-3-buten-1-ol

A solution of 3.4 g of 4-(4-isoquinolinyl)-3-butyn-1-ol in 35 mL of ethanol was hydrogenated over 0 35 g of 10% Pd/C at room temperature and atmospheric pressure for 5 hours. The catalyst was removed by filtration and the filtrate was evaporated to yield 3.3 g of (E)-4-(4-isoquinolinyl)-3-buten-1-ol as an oil.

EXAMPLE 174

Preparation of (E)-4-(4-chloro-1-butenyl)isoquinoline

A solution of 3.3 g of (E)-4-(4-isoquinolinyl)-3-buten-1-ol in 15 mL of dry chloroform was added to a cold solution of 1.8 mL of thionyl chloride in 5 mL of dry chloroform. After 15 minutes, the cooling bath was removed and the reaction was stirred at room temperature for 1 hour and then at reflux for 3 hours. The cooled mixture was washed with NaHCO₃ solution and with brine then was dried (Na₂SO₄) and evaporated. The residue was purified by chromatography over silica gel (ethyl acetate-toluene; 3:17) to yield 2.2 g of (E)-4-(4-chloro-1-butenyl)isoquinoline as an oil.

EXAMPLE 175

Preparation of (E)-1-[4-(4-isoquinolinyl)-3-butenyl]-1H-isoindole-1,3-(2H)-dione A mixture of 2.2 g of (E)-4-(4-chloro-1-butenyl) isoqunioline, 3.8 g of potassium phthalimide and 1.7 g of potassium iodide in 20 mL of dry dimethylformamide was maintained at 130° C. for 5 hours. After evaporation of the solvent, the residue was partioned between dichloromethane and water. The dried (Na₂SO₄) organic layer was concentrated and the crude product was purified by chromatography over silica gel (ethyl acetate-toluene; 3:7) to yield 1.75 g of (E)-1-[4-(4-isoquinolinyl)-3-butenyl]-1H-isoindole-1,3-(2H)-dione, mp 135°–140°.

EXAMPLE 176

Preparation of (E)-4-(4-isoquinolinyl)-3-buten-1-amine.

To a refluxing solution of 1.75 g of (E)-1-[4-(4-isoquinolinyl)-3-butenyl]-1H-isoindole-1,3-(2H-dione in 80 mL of ethanol was added 1.1 mL of hydrazine hydrate and the reaction was stirred at reflux for 17 hours. The solvent was removed in vacuo and the residue was triturated with chloroform. The extract was concentrated to yield 1 g of (E)-4-(4-isoquinolinyl)-3-buten-1-amine as an oil.

EXAMPLE 177

Preparation of 4-isoquinolinebutanamine

A solution of 1 g of (E)-4-(4-isoquinolinyl)-3-buten-1-amine in 20 mL of ethanol was hydrogenated over 0.12 g of 10% Pd/C at room temperature and atmospheric pressure. After 8 hours. the catalyst was removed by filtration and the filtrate was concentrated to yield 0.893 g of 4-isoquinolinebutanamine.

EXAMPLE 178

(R)-3',4'-Dimethoxy-2-(2-propenyl)-N-[1-methyl-4-(3-pyridinyl) butyl[]1,1'-biphenyl]-4-carboxamide A solution of 379 mg of 3',4'-dimethoxy-2-(2-propenyl)[1,1'-biphenyl]-4-carboxylic acid in 8 mL of dimethylformamide was cooled in an ice bath and 0.19 mL of triethylamine and 0.30 mL of diphenylphosphorylazide were added. After 1 hour. 0.223 g of (R)-alpha-methyl-3-pyridinebutanamine was added and the reaction mixture was allowed to warm to room temperature over 48 hours. The mixture was diluted with ethyl acetate and washed with water and saturated potassium carbonate, dried. and concentrated. The residue was chromatographed over 50 g of silica gel, eluting with ethyl acetate to afford 527 mg of (R)-3',4'-dimethoxy-2-(2-propenyl)-N-[1-methyl-4-(3-pyridinyl)butyl][1,1'-biphenyl]-4-carboxamide as a water white oil.

EXAMPLE 179

(R)-3',4'-Dimethoxy-2-propyl-N-[1-methyl-4-(3-pyridinyl)butyl][1,1'-bipheny]-4-carboxamide A solution of 282 mg of 3',4'-Dimethoxy-2-(2-propenyl)-N-[1-methyl-4-(3-pyridinyl)butyl][1,1'-biphenyl]-4-carb oxamide was hydrogenated over 40 mg of 10% palladium on carbon to give 268 mg of (R)-3',4'-Dimethoxy-2-propyl-N-[1-methyl-4-(3-Pyridinyl)butyl][1,1'-biphenyl]-4-carboxamide as a foam.

EXAMPLE 180

N-1,1-Dimethyl-4-(3-pyridinyl)butyl]-3'-methoxy[1,1'-biphenyl]4-carboxamide

A solution of 0.50 g of 3'-methoxy[1,1'-biphenyl]-4-carboxylic acid in 5 mL of dimethylformamide was cooled in an ice bath and 0.30 mL of triethylamine and 0.47 mL of diphenylphosphoryl azide were added. After 1.5 hour, 0.5 mL of alpha, alpha-dimethylpyridinebutanamine were added and the reaction mixture was allowed to warm to room temperature over 48 hours. The mixture was diluted with ethyl acetate and washed with water and brine. dried. and concentrated. The residue was chromatogrpahed over 50 g of silica gel, eluting with 1:1 ethyl acetate-hexane to give 0.35 g of N-[1 1-dimethyl-4-(3-pyridinyl)butyl]-3'-methoxy[1,1'-bipehnyl]-4-carboxamide.

EXAMPLE 181

3',4'-Dimethoxy-N-1.1-dimethyl-4-(3-pyridinyl)-butyl][1,1biphenyl]-4-carboxamide An ice cold solution of 3',4'-dimethoxy-[1,1'-biphenyl]-4-carboxylic acid in 6 mL of dimethylformamide was treated with 0.3 mL of triethylamine and 0.47 mL of diphenylphosphoryl azide. After 2 hours. 0.50 mL of alpha, alpha-dimethyl3-pyridinebutanamine was added and the mixture was allowed to warm to room temperature for 4 days. The reaction mixture was diluted with ethyl acetate and washed with water and saturated potassium carbonate. dried, and concentrated. The residue was chromatographed over 70 g of silica gel, eluting with 3:1 ethyl acetate-hexane to give 0.58 g of 3', 4'-Dimethoxy-N-[1,1-dimethyl-4-(3-pyridinyl) butyl][1,1-biphenyl]-4-carboxamide as a colorless oil.

EXAMPLE 182

| Tablet Formulation | | | | |
|---|---|---|---|---|
| Item Ingredients | mg/tablet | | | |
| 1. (R)-3',4'-dimethoxy-N-[1-methyl-4-(3-pyridinyl)butyl][1,1'-biphenyl]-4-carboxamide | 25.0 | 50.0 | 100.0 | 250.0 |
| 2. Pregelatinized Starch | 7.0 | 10.0 | 15.0 | 25.0 |
| 3. Lactose and DTG | 87.0 | 98.5 | 123.0 | 122.0 |
| 4. Avicel PH 102 | 30.0 | 40.0 | 60.0 | 100.0 |
| 5. Magnesium Stearate | 1.0 | 1.5 | 2.0 | 3.0 |
| | 150.0 | 200.0 | 300.0 | 500.0 |

Procedure
1. Mix Items 1, 2, 3, and 4 and granulate with water.
2. Dry the wet granulation at 45° C.
3. Screen the dried granulation through a suitable screen.
4. Add Item 5 and mix for 3 minutes. Compress on a suitable tablet press.

EXAMPLE 183

| Capsule Formulation | | | | |
|---|---|---|---|---|
| Item Ingredients | mg/tablet | | | |
| 1. (R)-3',4'-dimethoxy-N-[1-methyl-4-(3-pyridinyl)butyl][1,1'-biphenyl]-4-carboxamide | 25.0 | 50.0 | 100.0 | 250.0 |
| 2. Lactose Hydrous | 123.0 | 172.5 | 147.0 | 116.0 |
| 3. Corn Starch | 40.0 | 60.0 | 80.0 | 100.0 |
| 4. Talc | 10.0 | 15.0 | 20.0 | 30.0 |
| 5. Magnesium Stearate | 2.0 | 2.5 | 3.0 | 4.0 |
| | 200.0 | 300.0 | 350.0 | 500.0 |

Procedure
1. Mix Items 1, 2, 3, 4, and 5 in a suitable mixer.
2. Screen the powder mixture through a suitable screen.
3. Remix for 5 minutes and fill in capsule.

EXAMPLE 184

| Soft Gelatin Capsule | | | | |
|---|---|---|---|---|
| Item Ingredients | mg/capsule | | | |
| 1. (R)-3',4'-dimethoxy-N-[1-methyl-4-(3-pyridinyl)butyl][1,1'-biphenyl]-4-carboxamide | 25.0 | 50.0 | 100.0 | 250.0 |
| 2. Neobee M5 | 100.0 | 150.0 | 200.0 | 250.0 |
| 3. MCM 90 | 100.0 | 150.0 | 200.0 | 250.0 |
| | 225.0 | 350.0 | 500.0 | 750.0 |

Procedure
1. Mix Items 2, and 3.
2. Disperse/dissolve Item 1 in the solution in Step 1.
3. Fill in Soft Gelatin Capsule.

EXAMPLE 185

| Liquid Preparation | | |
|---|---|---|
| | 50 mg/ml % w/v | 100 mg/ml % w/v |
| 1. (R)-3',4'-dimethoxy-N-[1-methyl-4-(3-pyridinyl)butyl][1,1'-biphenyl]-4-carboxamide | 1.00 | 2.0 |
| 2. Citric Acid | 1.0 | 1.0 |
| 3. Glycerin | 12.5 | 12.5 |

-continued

| Liquid Preparation | | |
|---|---|---|
| | 50 mg/ml % w/v | 100 mg/ml % w/v |
| 4. Methyl Paraben | 0.09 | 0.09 |
| 5. Propyl Paraben | 0.01 | 0.01 |
| 6. Propylene Glycol v/v | 25 ml | 30 ml |
| 7. Alcohol USP v/v | 15 ml | 20 ml |
| 8. EDTA Sodium | 0.01 | 0.01 |
| 9. Sodium Saccharin | 1.0 | 1.5 |
| 10. Menthol USP | 0.5 | 0.5 |
| 11. Imit Cherry Flavor | 1.0 ml | 1.0 ml |
| 12. Water Distilled q.s. to | 100 ml | 100 ml |

Procedure
1. Dissolve Items 4, 5, 10 and 11 in Item 7 (USP Alcohol).
2. Dissolve Items 1, 2, 3, 6, 8, 9, in Part of Item 12 (water).
3. Mix solution in Step 1 and Step 2 until homogeneous solution is obtained.
4. Filter the solution through filter press using Hyflo-Super Cel.
5. Fill in suitable container.

We claim:
1. A compound of the formula

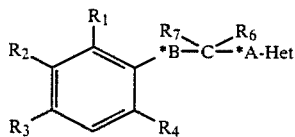

I wherein *B is

y is O or S, *A is —*(CH$_2$)$_n$—(X)$_m$—(CH$_2$)$_r$—, n or r, independently, are integers from 0 to 3, m is an integer from 0 to 1, provided that when m is 1, then n must be at least 1, X is O or S, R$_1$ and R$_4$, independently, are hydrogen, halogen, lower alkyl, hydroxy or lower alkoxy,
R$_2$ and R$_3$ are independently hydrogen, lower alkyl, cycloalkyl, halogen, nitro, lower alkoxy, lower alkenyl, lower alkynyl, phenyl, naphthalenyl, or phenyl or naphthalenyl mono-, di- or trisubstituted by halogen, trifluoromethyl, lower alkyl, lower alkoxy or nitro, R$_5$ and R$_6$, independently are hydrogen or lower alkyl, R$_7$ is hydrogen, lower alkyl, cycloalkyl, phenyl, naphthalenyl, or phenyl or naphthalenyl mono-, di- or trisubstituted by halogen, trifluoromethyl, lower alkyl, lower alkoxy or nitro, Het is pyridyl unsubstituted or substituted by lower alkyl, halogen, phenyl, naphthalenyl, or phenyl or naphthalenyl mono-, di- or trisubstituted hy halogen, trifluoromethyl, lower alkyl, lower alkoxy or nitro, and the asterisk denotes the point of attachment, and, provided that at least one of R$_2$ and R$_3$ is phenyl, naphthalenyl, or phenyl or naphthalenyl mono-, di- or trisubstituted by halogen, trifluoromethyl, lower alkyl, lower alkoxy or nitro, or when R$_6$ and R$_7$ are different, an enantiomer or racemic mixture thereof, or a pharmaceutically acceptable acid addition salt thereof.

2. A compound in accordance with claim 1, wherein R$_1$ is hydrogen, or lower alkyl, R$_2$ is hydrogen, halogen, nitro, lower alkyl, lower alkenyl, lower alkynyl, lower alkoxy, phenyl optionally substituted with up to three subsitutents selected from halogen, lower alkyl or lower alkoxy, R$_3$ is phenyl optionally substituted with up to three substituents selected from lower alkyl, lower alkoxy, nitro, or halogen, R$_4$ is hydrogen, lower alkyl or lower alkoxy, R$_5$ is hydrogen or lower alkyl, B* is a carboxamide or thiocarboxamide, *A is —(CH$_2$)$_n$—(X)$_m$—(CH$_2$)$_r$— wherein n+r=2 to 6, m=0, R$_6$ is hydrogen or lower alkyl, R$_7$ is hydrogen or lower alkyl, Het is pyridyl.

3. A compound in accordance with claim 1, wherein R$_1$ and R$_4$ independently are hydrogen or lower alkyl, R$_2$ is hydrogen, lower alkyl, nitro, halogen, lower alkenyl or phenyl substituted with up to three substituents selected from halogen, lower alkyl and lower alkoxy, R$_3$ is phenyl optionally substituted with up to three substituents selected from halogen, lower alkyl and lower alkoxy, R$_3$ is phenyl optionally substituted with up to three substituents selected from halogen, lower alkyl or lower alkoxy, R$_5$ is hydrogen, *B is a carboxamide or thiocarboxamide, *A is —(CH$_2$)$_n$—(X)$_m$—(CH$_2$)$_r$— wherein $n+r=4$, m=0, and Het is pyridnyl.

4. A compound in accordance with claim 1, wherein R$_1$ and R$_4$ are hydrogen, R$_2$ is hydrogen, phenyl, lower alkenyl or lower alkyl, Het is pyridinyl, R$_3$ is phenyl optionally substituted with one or two lower alkoxy groups, R$_5$ is hydrogen and one of R$_6$ and R$_7$ is lower alkyl and the other is hydrogen.

5. A compound in accordance with claim 1, rac.-3',4,'-dimethoxy-N-[1-methyl-4-(3-pyridinyl)butyl][1,1'-biphenyl]-4-carbothioamide.

6. A compound in accordance with claim 1, (R)-3',4'-dimethoxy-N-[1-methyl-4-(3-pyridinyl)butyl][1,1'-biphenyl]-4-carboxamide.

7. A compound in accordance with claim 1, (R)-2-butyl-3',4'-dimethoxy-N-[1-methyl-4-(3-pyridinyl)-butyl][1,1'-biphenyl]-4-carboxamide.

8. A compound in accordance with claim 1, (R)-3+,4'-dimethoxy-2-ethyl-N-[1-methyl-4-(3-pyridinyl)-butyl][1,1'-biphenyl]-4-carboxamide.

9. A compound in accordance with claim 1. (R)-3+,4'-dimethoxy-2-(2-propenyl)-N-[1-methyl-4-(3-pyridinyl) butyl][1,1'-biphenyl]-4-carboxamide.

10. A compound in accordance with claim 1, (R)-2-bromo-3',4'-dimethoxy-N-[1-methyl-4-(3-pyridinyl)-butyl][1,1'-biphenyl]-4-carboxamide.

11. A compound in accordance with claim 1, (R) 3,,4,-dimethoxy-2-nitro-N-[1-methyl-4-(3-pyridinyl)-butyl][1,1'-biphenyl]-4-carboxamide.

12. A pharmaceutical composition comprising a compound of the formula

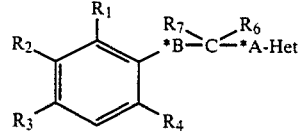

I wherein *B is

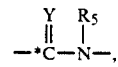

Y is O or S, *A is —*(CH$_2$)$_n$—(X)$_m$—(CH$_2$)$_r$—, n or r, independently, are integers from 0 to 3, m is an integer, from 0 to 1, provided that when m is 1, then n must be at least 1, X is O or S, R$_1$ and R$_4$, independently, are hydrogen, halogen, lower alkyl, hydroxy or lower alkoxy,
R$_2$ and R$_3$ are independently hydrogen, lower alkyl, cycloalkyl, halogen, nitro, lower alkoxy, lower alkenyl, lower alkynyl phenyl, naphthalenyl, or phenyl or naphthalenyl mono-, di- or trisubstituted by halogen, trifluoromethyl, lower alkyl, lower alkoxy or nitro, $R_5$ and $R_6$, independently are hydrogen or lower alkyl, $R_7$ is hydrogen, lower alkyl, cycloalkyl, phenyl, naphthalenyl, or phenyl or naphthalenyl mono-, di- or trisubstituted by halogen, trifluoromethyl, lower alkyl, lower alkoxy, or nitro, Het is pyridyl unsubstituted or substituted by lower alkyl, halogen, phenyl, naphthalenyl, or phenyl or naphthalenyl mono-, di- or trisubstituted by halogen, trifluoromethyl, lower alkyl, lower alkoxy, or nitro, and the asterisk denotes the point of attachment, and, provided that at least one of $R_2$ and $R_3$ is phenyl, naphthalenyl, or phenyl or naphthalenyl mono-, di- or trisubstituted by halogen, trifluoromethyl, lower alkyl, lower alkoxy or nitro, or when $R_6$ and $R_7$ are different, an enantiomer or racemic mixture thereof, or a pharmaceutically acceptable acid addition salt thereof, and an inert carrier material.

13. A pharmaceutical composition in accordance with claim ,13, wherein the compound of the formula I is rac.-3',4'-dimethoxy-N-[1-methyl-4-(3-pyridinyl)-butyl][1,1'-biphenyl]-4-carbothioamide.

14. A pharmaceutical composition in accordance with claim 13, wherein the compound of formula I is (R)-3',4'-dimethoxy-N-[1-methyl-4-pyridinyl)-butyl][1,1'-biphenyl]-4-carboxamide.

15. A pharmaceutical composition in accordance with claim 13, wherein the compound of formula I is (R)-2-butyl-3',4'-dimethoxy-N-[1-methyl-4-(3-pyridinyl)butyl][1,1'-biphenyl]-4-carboxamide.

16. A method of treating a disease state due to an excess of platelet activating factor which comprises administering to a host in need of such treatment an effective amount of a compound of the formula

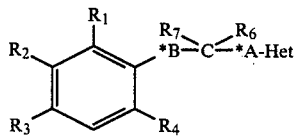

where *B is

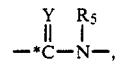

Y is O or S, *A is —*(CH$_2$)$_n$—(X)$_m$—(CH$_2$)$_r$—, n or r, independently, are integers from 0 to 3, m is an integer from 0 to 1, provided that when m is 1, then n must be at least 1, X is O or S, $R_1$ and $R_4$, independently, are hydrogen, halogen, lower alkyl, hydroxy or lower alkoxy, $R_2$ and $R_3$ are independently hydrogen, lower alkyl, cycloalkyl, hydrogen, nitro, lower alkoxy, lower alkenyl, lower alkynyl, phenyl, naphthalenyl, or phenyl or naphthalenyl mono-, di- or trisubstituted by halogen, trifluoromethyl, lower alkyl, lower alkoxy or nitro, $R_5$ and $R_6$, independently are hydrogen or lower alkyl, $R_7$ is hydrogen, lower alkyl, cycloalkyl, phenyl, naphthalenyl, or phenyl or naphthalenyl mono-, di- or trisubstituted by halogen, trifluoromethyl, lower alkyl, lower alkoxy or nitro, Het is pyridyl unsubstituted or substituted by lower alkyl, halogen, phenyl, naphthalenyl, or phenyl or naphthalenyl mono-, di- or trisubstituted by halogen, trifluoromethyl, lower alkyl, lower alkoxy or nitro, and the asterisk denotes the point of attachment, and, provided that at least one of $R_2$ and $R_3$ is phenyl, naphthalenyl, or phenyl or naphthalenyl mono-, di-or trisubstituted by halogen, trifluoromethyl, lower alkyl, lower alkoxy or nitro, or, when $R_6$ and $R_7$ are different, an enantiomer or racemic mixture thereof, or a pharmaceutically acceptable acid addition salt thereof.

17. A method in accordance ,with claim 16, wherein the compound of formula I is rac.-3',4'-dimethoxy-N-[1-methyl-4-(3-pyridinyl)butyl][1,1'-biphenyl]-4-carbothioamide.

18. A method in accordance with claim 16, wherein the compound of formula I is (R)-3', 4'-dimethoxy-N-[1-methyl-4-(3-pyridinyl)butyl][1,1'-biphenyl]-4-carboxamide.

19. A method in accordance with claim 16, wherein the compound of formula I is (R)-2-butyl-3',4'-dimethoxy-N-[1-methyl-4-(3-pyridinyl)butyl][1,1'-piphenyl]-4-carboxamide.

* * * * *

UNITED STATES PATENT AND TRADEMARK OFFICE
CERTIFICATE OF CORRECTION

PATENT NO.   : 4,916,145
DATED        : April 10, 1990
INVENTOR(S)  : Tilley et al.

It is certified that error appears in the above-identified patent and that said Letters Patent is hereby corrected as shown below:

Claim 8, Column 76, line 34,

" 3 +, 4' "     should be     --- 3', 4' --- .

Claim 9, Column 76, line 37,

" 3 +, 4' "     should be     --- 3', 4' ---.

Claim 16, Column 78, line 12,

" hydrogen "    should be     --- halogen ---.

Signed and Sealed this

Twenty-seventh Day of August, 1991

Attest:

HARRY F. MANBECK, JR.

*Attesting Officer*

*Commissioner of Patents and Trademarks*